(12) United States Patent
Chinnaiyan et al.

(10) Patent No.: US 9,476,096 B2
(45) Date of Patent: Oct. 25, 2016

(54) RECURRENT GENE FUSIONS IN HEMANGIOPERICYTOMA

(71) Applicant: The Regents of The University of Michigan, Ann Arbor, MI (US)

(72) Inventors: Arul Chinnaiyan, Plymouth, MI (US); Dan Robinson, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 463 days.

(21) Appl. No.: 13/962,590

(22) Filed: Aug. 8, 2013

(65) Prior Publication Data

US 2014/0178871 A1 Jun. 26, 2014

Related U.S. Application Data

(60) Provisional application No. 61/680,891, filed on Aug. 8, 2012.

(51) Int. Cl.
*C12Q 1/68* (2006.01)
*G01N 33/574* (2006.01)
*G01N 33/569* (2006.01)

(52) U.S. Cl.
CPC ........... *C12Q 1/6883* (2013.01); *C12Q 1/6886* (2013.01); *G01N 33/56966* (2013.01); *G01N 33/57407* (2013.01); *C12Q 2600/156* (2013.01)

(58) Field of Classification Search
None
See application file for complete search history.

(56) References Cited

PUBLICATIONS

Mohajeri et al. (Genes Chromosoems & cancer 52:873-886 (2013).*
Chmielecki et al. (Nature Genetics, vol. 45, No. 2, published Jan. 13, 2013, pp. 131-132).*
Amary et al., "Detection of SS18-SSX fusion transcripts in formalin-fixed paraffin-embedded neoplasms: analysis of conventional RT-PCR, qRT-PCR and dual color FISH as diagnostic tools for synovial sarcoma." Mod Pathol. Apr. 2007; 20(4):482-96.
Bouvier et al., "Solitary fibrous tumors and hemangiopericytomas of the meninges: overlapping pathological features and common prognostic factors suggest the same spectrum of tumors." Brain Pathol. Jul. 2012; 22(4):511-21.
de Klein et al., "A cellular oncogene is translocated to the Philadelphia chromosome in chronic myelocytic leukaemia." Nature. Dec. 23, 1982;300(5894):765-7.
Debiec-Rychter et al., "Is 4q13 a recurring breakpoint in solitary fibrous tumors?" Cancer Genet Cytogenet. Nov. 2001;131(1):69-73.
Deininger, "The development of imatinib as a therapeutic agent for chronic myeloid leukemia." Blood. Apr. 1, 2015; 105 (7):2640-53.
Gold et al., "Clinicopathologic correlates of solitary fibrous tumors." Cancer. Feb. 15, 2002; 94(4):1057-68.
Hajdu et al., "IGF2 over-expression in solitary fibrous tumours is independent of anatomical location and is related to loss of imprinting." J Pathol. Jul. 2010; 221(3):300-7.
Kumbrink et al., "Egr-1 induces the expression of its corepressor nab2 by activation of the nab2 promoter thereby establishing a negative feedback loop." J Biol Chem. Dec. 30, 2005;280(52):42785-93.
Li et al., "Insulin receptor activation in solitary fibrous tumours." J Pathol. Apr. 2007; 211(5):550-4.
Mandahl et al., "Aberrations of chromosome segment 12q13-15 characterize a subgroup of hemangiopericytomas." Cancer. May 15, 1993; 71(10):3009-13.
Welch et al., "Use of whole-genome sequencing to diagnose a cryptic fusion oncogene." JAMA. Apr. 20, 2011; 305 (15):1577-84.
Mitelman, "Rent chromosome aberrations in Cancer." Mutat Res. Apr. 2000;462(2-3):247-53.
Mosquera & Fletcher, "Expanding the spectrum of malignant progression in solitary fibrous tumors: a study of 8 cases with a discrete anaplastic component—is this dedifferentiated SFT?" Am J Surg Pathol. Sep. 2009; 33(9):1314-21.
Panagopoulos et al., "The chimeric FUS/CREB3l2 gene is specific for low-grade fibromyxoid sarcoma." Genes Chromosomes Cancer. Jul. 2004; 40(3):218-28.
Park & Araujo, "New insights into the hemangiopericytoma/solitary fibrous tumor spectrum of tumors." Curr Opin Oncol. Jul. 2009; 21(4):327-31.
Rabbitts, "Chromosomal translocations in human cancer." Nature. Nov. 10, 1994; 372(6502):143-9.
Robinson et al., "Identification of recurrent NAB2-STAT6 gene fusions in solitary fibrous tumor by integrative sequencing." Nat Genet. Feb. 2013; 45(2):180-5.
Rowley JD, "Chromosome translocations: dangerous liaisons revisited." Nat Rev Cancer. Dec. 2001;1(3):245-50.
Rowley, "Letter: A new consistent chromosomal abnormality in chronic myelogenous leukaemia identified by quinacrine fluorescence and Giemsa staining." Nature. Jun. 1, 1973; 243(5405):290-3.
Roychowdhury et al., "Personalized oncology through integrative high-throughput sequencing: a pilot study." Sci Transl Med. Nov. 30, 2011;3(111):111ra121.
Ruiz et al., "Advancing a clinically relevant perspective of the clonal nature of cancer." Proc Natl Acad Sci U S A. Jul. 19, 2011; 108(29):12054-9.
Srinivasan et al., "NAB2 represses transcription by interacting with the CHD4 subunit of the nucleosome remodeling and deacetylase (NuRD) complex." J Biol Chem. Jun. 2, 2006; 281(22):15129-37.

(Continued)

Primary Examiner — Juliet Switzer
(74) Attorney, Agent, or Firm — Casimir Jones, S.C.; Tanya Arenson; David Casimir

(57) ABSTRACT

Provided herein are kits, compositions and methods for cancer diagnosis, research and therapy, including but not limited to, cancer markers. In particular, the present invention relates to recurrent gene fusions as diagnostic markers and clinical targets for hemangiopericytoma.

8 Claims, 15 Drawing Sheets

(56) References Cited

PUBLICATIONS

Svaren et al., "EGR1 target genes in prostate carcinoma cells identified by microarray analysis." J Biol Chem. Dec. 8, 2000; 275(49):38524-31.

Svaren et al., "Novel mutants of NAB corepressors enhance activation by Egr transactivators." EMBO J. Oct. 15, 1998; 17(20):6010-9.

Svaren et al., "The Nab2 and Stat6 genes share a common transcription termination region." Genomics. Apr. 1, 1997; 41(1):33-9.

Svaren et al., "NAB2, a corepressor of NGFI-A (Egr-1) and Krox20, is induced by proliferative and differentiative stimuli." Mol Cell Biol. Jul. 1996;16(7):3545-53.

Thiel & Cibelli, "Regulation of life and death by the zinc finger transcription factor Egr-1." J Cell Physiol. Dec. 2002; 193(3):287-92.

* cited by examiner

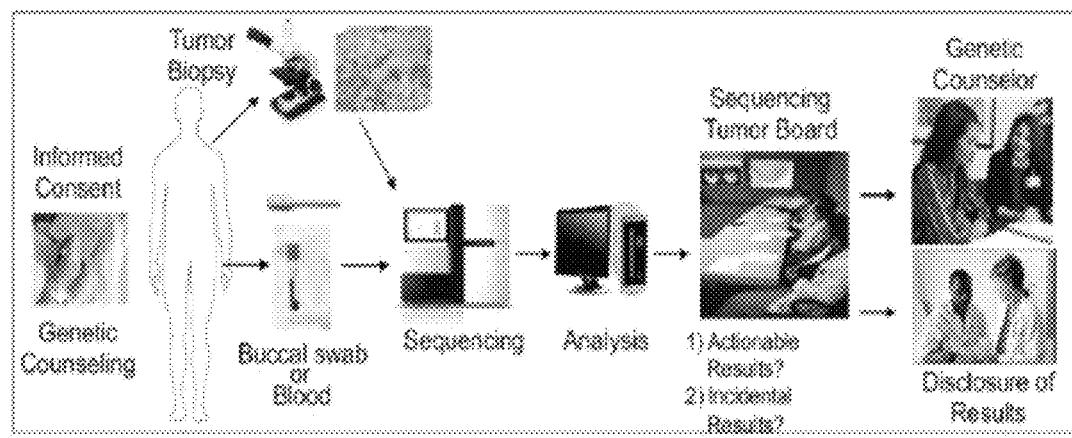

B          C

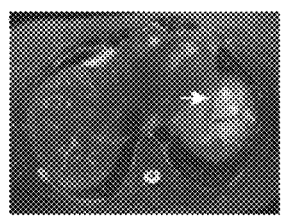 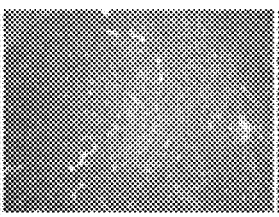 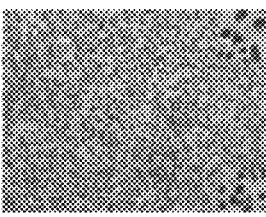 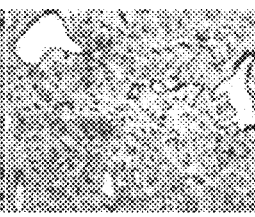

D

Nonsynonymous somatic mutations

| GENE | NAME | PROTEIN |
|---|---|---|
| EPRS | Glutamyl-prolyl-tRNA synthetase | L1014F |
| RBM10 | RNA binding motif protein 10 | N214S |
| FCGR3A | Fc fragment of IgG receptor IIIa | W70L |
| STX6 | Syntaxin 6 | S86I |
| ASCC3 | Activating signal cointegrator 1 complex subunit 3 | N1440S |
| FRYL | FRY-like | Q1360K |
| ZNF711 | Zinc finger protein 711 | N349I |
| RNF103 | Ring finger protein 103 | E94K |
| ARHGEF5 | Rho guanine nucleotide exchange factor (GEF) 5 | Q233* |
| GLIPR1L2 | GLI pathogenesis-related 1 like 2 | K240N |
| OR4K5 | Olfactory receptor, family 4, subfamily K, member 5 | T239M |
| SLFN14 | Schlafen family member 14 | E200G |
| CLCA1 | Chloride channel accessory 1 | S767N |
| OR2G2 | Olfactory receptor, family 2, subfamily G, member 2 | R125C |

A

B

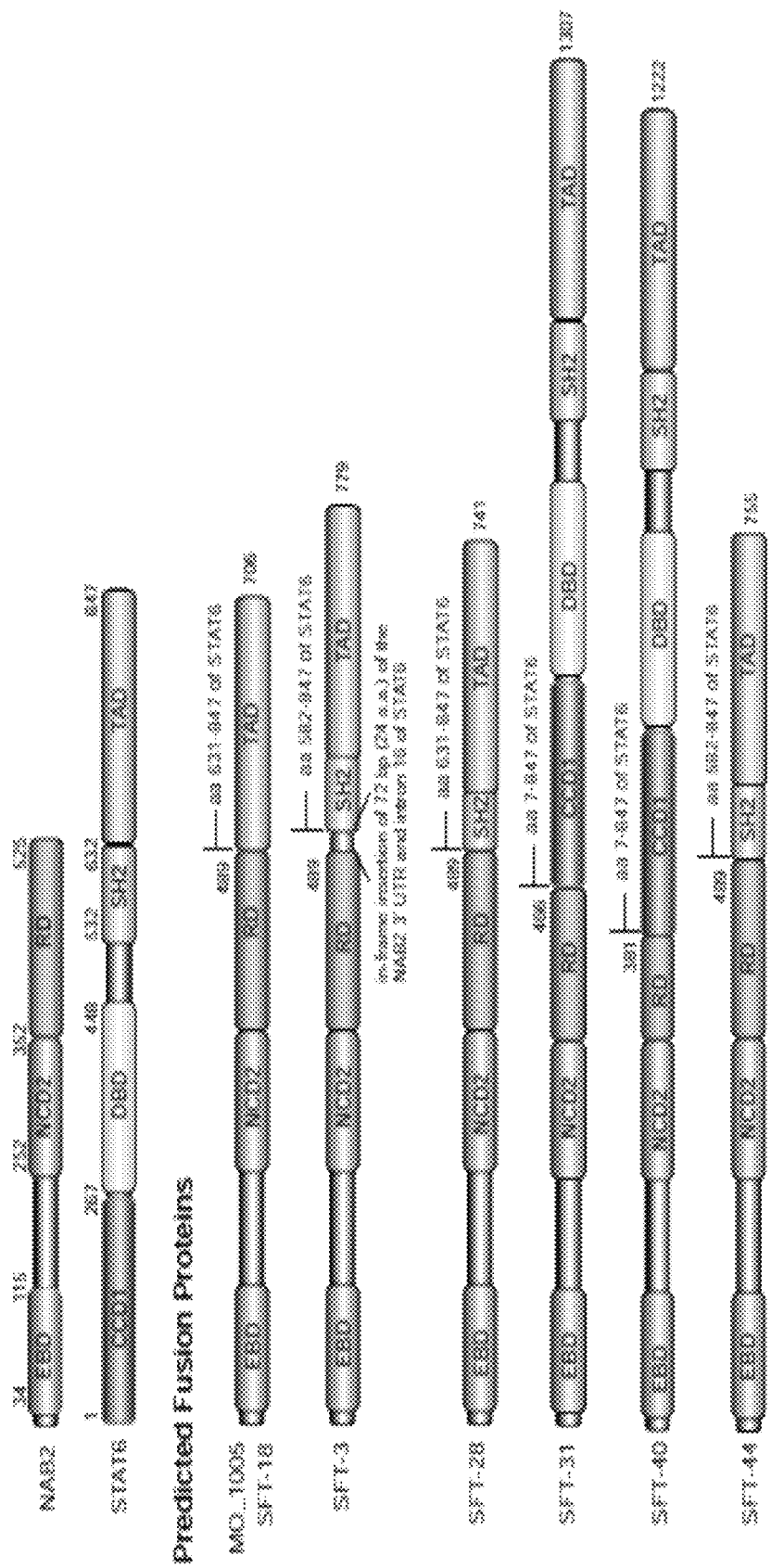

B

C

D

E

A

B

A

B

SFT-3 NAB2-STAT6 Fusion junction

SFT-18 NAB2-STAT6 Fusion junction (same as in MC_1005)

SFT-28 NAB2-STAT6 Fusion junction

SFT-44 NAB2-STAT6 Fusion junction

SEQUENCE LISTING

```
<160> NUMBER OF SEQ ID NOS: 52

<210> SEQ ID NO 1
<211> LENGTH: 23
<212> TYPE: DNA
<213> ORGANISM: Artificial Sequence
<220> FEATURE:
<223> OTHER INFORMATION: Synthetic

<400> SEQUENCE: 1
cctgtctggg gagagtctgg atg                                                 23
```

```
<210> SEQ ID NO 2
<211> LENGTH: 22
<212> TYPE: DNA
<213> ORGANISM: Artificial Sequence
<220> FEATURE:
<223> OTHER INFORMATION: Synthetic

<400> SEQUENCE: 2 gggggatgg agtgagagtg tg                                             22

<210> SEQ ID NO 3
<211> LENGTH: 31
<212> TYPE: DNA
<213> ORGANISM: Artificial Sequence
<220> FEATURE:
<223> OTHER INFORMATION: Synthetic

<400> SEQUENCE: 3
caacggtccg accatgcaca gagcgccttc c                                  31

<210> SEQ ID NO 4
<211> LENGTH: 40
<212> TYPE: DNA
<213> ORGANISM: Artificial Sequence
<220> FEATURE:
<223> OTHER INFORMATION: Synthetic

<400> SEQUENCE: 4
ccttacccat ctgttcagct gcgagaggtg gcttcgcagg                         40

<210> SEQ ID NO 5
<211> LENGTH: 40
<212> TYPE: DNA
<213> ORGANISM: Artificial Sequence
<220> FEATURE:
<223> OTHER INFORMATION: Synthetic

<400> SEQUENCE: 5
aagccacctc tcgcagctga acagatgggt aaggatggca                         40

<210> SEQ ID NO 6
<211> LENGTH: 31
<212> TYPE: DNA
<213> ORGANISM: Artificial Sequence
<220> FEATURE:
<223> OTHER INFORMATION: Synthetic

<400> SEQUENCE: 6
caacggaccg caagtgtcca gagcaggtct g                                  31

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
cctcagcctc cactttcacg                                               20

<210> SEQ ID NO 8
<211> LENGTH: 21
<212> TYPE: DNA
<213> ORGANISM: Artificial Sequence
<220> FEATURE:
<223> OTHER INFORMATION: Synthetic
```

```
<400> SEQUENCE: 8 cagggggaatg atagaaagga a                                              21

<210> SEQ ID NO 9
<211> LENGTH: 24
<212> TYPE: DNA
<213> ORGANISM: Artificial Sequence
<220> FEATURE:
<223> OTHER INFORMATION: Synthetic

<400> SEQUENCE: 9
gtacgcatgg tggtggaaag tgtg                                            24

<210> SEQ ID NO 10
<211> LENGTH: 22
<212> TYPE: DNA
<213> ORGANISM: Artificial Sequence
<220> FEATURE:
<223> OTHER INFORMATION: Synthetic

<400> SEQUENCE: 10
gggatgctgg ggaggtcaca tc                                              22

<210> SEQ ID NO 11
<211> LENGTH: 22
<212> TYPE: DNA
<213> ORGANISM: Artificial Sequence
<220> FEATURE:
<223> OTHER INFORMATION: Synthetic

<400> SEQUENCE: 11
gctatggagc cgacacatcc tg                                              22

<210> SEQ ID NO 12
<211> LENGTH: 22
<212> TYPE: DNA
<213> ORGANISM: Artificial Sequence
<220> FEATURE:
<223> OTHER INFORMATION: Synthetic

<400> SEQUENCE: 12
ggaagtggtt ggtccctttc ca                                              22

<210> SEQ ID NO 13
<211> LENGTH: 23
<212> TYPE: DNA
<213> ORGANISM: Artificial Sequence
<220> FEATURE:
<223> OTHER INFORMATION: Synthetic

<400> SEQUENCE: 13
tgcagcagac actgatggac gag                                             23

<210> SEQ ID NO 14
<211> LENGTH: 23
<212> TYPE: DNA
<213> ORGANISM: Artificial Sequence
<220> FEATURE:
<223> OTHER INFORMATION: Synthetic

<400> SEQUENCE: 14
tctccagcca gtcacccaga aga                                             23
```

```
<210> SEQ ID NO 15
<211> LENGTH: 25
<212> TYPE: DNA
<213> ORGANISM: Artificial Sequence
<220> FEATURE:
<223> OTHER INFORMATION: Synthetic

<400> SEQUENCE: 15
ccctccactg aagaagctga aacaa                                              25

<210> SEQ ID NO 16
<211> LENGTH: 24
<212> TYPE: DNA
<213> ORGANISM: Artificial Sequence
<220> FEATURE:
<223> OTHER INFORMATION: Synthetic

<400> SEQUENCE: 16
cactagccaa gttgcagcag aagg                                               24

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
acctggccct cctggagacg                                                    20

<210> SEQ ID NO 18
<211> LENGTH: 22
<212> TYPE: DNA
<213> ORGANISM: Artificial Sequence
<220> FEATURE:
<223> OTHER INFORMATION: Synthetic

<400> SEQUENCE: 18
ggggaagttg tccggaagca cg                                                 22

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
gcggcggcgg aaaccctaaa                                                    20

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
cgggaccgtc cactcgcaca                                                    20

<210> SEQ ID NO 21
<211> LENGTH: 20
<212> TYPE: DNA
<213> ORGANISM: Artificial Sequence
<220> FEATURE:
<223> OTHER INFORMATION: Synthetic
```

<400> SEQUENCE: 21
gtaggcgccc aggcatcgtg                                                  20

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
tccaaccagc tgccacgtcc                                                  20

<210> SEQ ID NO 23
<211> LENGTH: 21
<212> TYPE: DNA
<213> ORGANISM: Artificial Sequence
<220> FEATURE:
<223> OTHER INFORMATION: Synthetic

<400> SEQUENCE: 23
tgtggggtca tgtccaaggc t                                                21

<210> SEQ ID NO 24
<211> LENGTH: 23
<212> TYPE: DNA
<213> ORGANISM: Artificial Sequence
<220> FEATURE:
<223> OTHER INFORMATION: Synthetic

<400> SEQUENCE: 24
cggtcatctt gatggtagct ggg                                              23

<210> SEQ ID NO 25
<211> LENGTH: 38
<212> TYPE: DNA
<213> ORGANISM: Artificial Sequence
<220> FEATURE:
<223> OTHER INFORMATION: Synthetic

<400> SEQUENCE: 25
gcgaagccac ctctcgcagc tgaacagatg ggtaagga                              38

<210> SEQ ID NO 26
<211> LENGTH: 22
<212> TYPE: DNA
<213> ORGANISM: Artificial Sequence
<220> FEATURE:
<223> OTHER INFORMATION: Synthetic

<400> SEQUENCE: 26
aaattccagc gctctgattc ct                                               22

<210> SEQ ID NO 27
<211> LENGTH: 102
<212> TYPE: DNA
<213> ORGANISM: Artificial Sequence
<220> FEATURE:
<223> OTHER INFORMATION: Synthetic

<400> SEQUENCE: 27
ccacctctcg caggtttgca ccagtggtgt gagcagttgg actcagtttg gacagaggga      60
tctcagggtc tccttcctac cataggctct ccacagatag ag                        102

```
<210> SEQ ID NO 28
<211> LENGTH: 67
<212> TYPE: DNA
<213> ORGANISM: Artificial Sequence
<220> FEATURE:
<223> OTHER INFORMATION: Synthetic

<400> SEQUENCE: 28
cctgtgtgcc tgcgaagcca cctctcgcag ctgaacagat gggtaaggat ggcaggggtt    60
atgtccc                                                              67

<210> SEQ ID NO 29
<211> LENGTH: 67
<212> TYPE: DNA
<213> ORGANISM: Artificial Sequence
<220> FEATURE:
<223> OTHER INFORMATION: Synthetic

<400> SEQUENCE: 29
cctgtgtgcc tgcgaagcca cctctcgcag acctgtccat tcgctcactg ggggaccgaa    60
tccggga                                                              67

<210> SEQ ID NO 30
<211> LENGTH: 67
<212> TYPE: DNA
<213> ORGANISM: Artificial Sequence
<220> FEATURE:
<223> OTHER INFORMATION: Synthetic

<400> SEQUENCE: 30
cctgtgtgcc tgcgaagcca cctctcgcag gctctccaca gatagagaac atccagccat    60
tctctgc                                                              67

<210> SEQ ID NO 31
<211> LENGTH: 30
<212> TYPE: DNA
<213> ORGANISM: Artificial sequence
<220> FEATURE:
<223> OTHER INFORMATION: Synthetic

<400> SEQUENCE: 31
caacggtccg accatgcaca gagcgccttc                                     30

<210> SEQ ID NO 32
<211> LENGTH: 40
<212> TYPE: DNA
<213> ORGANISM: Artificial sequence
<220> FEATURE:
<223> OTHER INFORMATION: Synthetic

<400> SEQUENCE: 32
ccttacccat ctgttcagct gcgagaggtg gcttcgcagg                          40

<210> SEQ ID NO 33
<211> LENGTH: 40
<212> TYPE: DNA
<213> ORGANISM: Artificial sequence
<220> FEATURE:
<223> OTHER INFORMATION: Synthetic

<400> SEQUENCE: 33
aagccacctc tcgcagctga acagatgggt aaggatggca                          40
```

<210> SEQ ID NO 34
<211> LENGTH: 31
<212> TYPE: DNA
<213> ORGANISM: Artificial sequence
<220> FEATURE:
<223> OTHER INFORMATION: Synthetic

<400> SEQUENCE: 34
caacggaccg caagtgtcca gagcaggtct g        31

<210> SEQ ID NO 35
<211> LENGTH: 20
<212> TYPE: DNA
<213> ORGANISM: Artificial sequence
<220> FEATURE:
<223> OTHER INFORMATION: Synthetic

<400> SEQUENCE: 35
cctcagcctc cactttcacg        20

<210> SEQ ID NO 36
<211> LENGTH: 21
<212> TYPE: DNA
<213> ORGANISM: Artificial sequence
<220> FEATURE:
<223> OTHER INFORMATION: Synthetic

<400> SEQUENCE: 36 cagggggaatg atagaaagga a        21

<210> SEQ ID NO 37
<211> LENGTH: 24
<212> TYPE: DNA
<213> ORGANISM: Artificial sequence
<220> FEATURE:
<223> OTHER INFORMATION: Synthetic

<400> SEQUENCE: 37
gtacgcatgg tggtggaaag tgtg        24

<210> SEQ ID NO 38
<211> LENGTH: 22
<212> TYPE: DNA
<213> ORGANISM: Artificial sequence
<220> FEATURE:
<223> OTHER INFORMATION: Synthetic

<400> SEQUENCE: 38
gggatgctgg ggaggtcaca tc        22

<210> SEQ ID NO 39
<211> LENGTH: 22
<212> TYPE: DNA
<213> ORGANISM: Artificial sequence
<220> FEATURE:
<223> OTHER INFORMATION: Synthetic

<400> SEQUENCE: 39
gctatggagc cgacacatcc tg        22

<210> SEQ ID NO 40
<211> LENGTH: 22
<212> TYPE: DNA
<213> ORGANISM: Artificial sequence
<220> FEATURE:
<223> OTHER INFORMATION: Synthetic -continued

<400> SEQUENCE: 40
ggaagtggtt ggtccctttc ca                                           22

<210> SEQ ID NO 41
<211> LENGTH: 23
<212> TYPE: DNA
<213> ORGANISM: Artificial sequence
<220> FEATURE:
<223> OTHER INFORMATION: Synthetic

<400> SEQUENCE: 41
tgcagcagac actgatggac gag                                          23

<210> SEQ ID NO 42
<211> LENGTH: 23
<212> TYPE: DNA
<213> ORGANISM: Artificial sequence
<220> FEATURE:
<223> OTHER INFORMATION: Synthetic

<400> SEQUENCE: 42
tctccagcca gtcacccaga aga                                          23

<210> SEQ ID NO 43
<211> LENGTH: 25
<212> TYPE: DNA
<213> ORGANISM: Artificial sequence
<220> FEATURE:
<223> OTHER INFORMATION: Synthetic

<400> SEQUENCE: 43
ccctccactg aagaagctga aacaa                                        25

<210> SEQ ID NO 44
<211> LENGTH: 24
<212> TYPE: DNA
<213> ORGANISM: Artificial sequence
<220> FEATURE:
<223> OTHER INFORMATION: Synthetic

<400> SEQUENCE: 44
cactagccaa gttgcagcag aagg                                         24

<210> SEQ ID NO 45
<211> LENGTH: 20
<212> TYPE: DNA
<213> ORGANISM: Artificial sequence
<220> FEATURE:
<223> OTHER INFORMATION: Synthetic

<400> SEQUENCE: 45
acctggccct cctggagacg                                              20

<210> SEQ ID NO 46
<211> LENGTH: 22
<212> TYPE: DNA
<213> ORGANISM: Artificial sequence
<220> FEATURE:
<223> OTHER INFORMATION: Synthetic

<400> SEQUENCE: 46
ggggaagttg tccggaagca cg                                           22

```
<210> SEQ ID NO 47
<211> LENGTH: 20
<212> TYPE: DNA
<213> ORGANISM: Artificial sequence
<220> FEATURE:
<223> OTHER INFORMATION: Synthetic

<400> SEQUENCE: 47
gcggcggcgg aaaccctaaa                                                    20

<210> SEQ ID NO 48
<211> LENGTH: 20
<212> TYPE: DNA
<213> ORGANISM: Artificial sequence
<220> FEATURE:
<223> OTHER INFORMATION: Synthetic

<400> SEQUENCE: 48
cgggaccgtc cactcgcaca                                                    20

<210> SEQ ID NO 49
<211> LENGTH: 20
<212> TYPE: DNA
<213> ORGANISM: Artificial sequence
<220> FEATURE:
<223> OTHER INFORMATION: Synthetic

<400> SEQUENCE: 49
gtaggcgccc aggcatcgtg                                                    20

<210> SEQ ID NO 50
<211> LENGTH: 20
<212> TYPE: DNA
<213> ORGANISM: Artificial sequence
<220> FEATURE:
<223> OTHER INFORMATION: Synthetic

<400> SEQUENCE: 50
tccaaccagc tgccacgtcc                                                    20

<210> SEQ ID NO 51
<211> LENGTH: 21
<212> TYPE: DNA
<213> ORGANISM: Artificial sequence
<220> FEATURE:
<223> OTHER INFORMATION: Synthetic

<400> SEQUENCE: 51
tctggggtca tgtccaaggc t                                                  21

<210> SEQ ID NO 52
<211> LENGTH: 23
<212> TYPE: DNA
<213> ORGANISM: Artificial sequence
<220> FEATURE:
<223> OTHER INFORMATION: Synthetic

<400> SEQUENCE: 52
cggtcatctt gatggtagct ggg                                                23
```

RECURRENT GENE FUSIONS IN HEMANGIOPERICYTOMA

This application claims priority to U.S. Provisional Patent Application Ser. No. 61/680,891, filed Aug. 8, 2012, which is herein incorporated by reference in its entirety.

STATEMENT REGARDING FEDERALLY SPONSORED RESEARCH OR DEVELOPMENT

This invention was made with government support under CA111275 awarded by the National Institutes of Health. The government has certain rights in the invention.

FIELD OF THE INVENTION

Provided herein are kits, compositions and methods for cancer diagnosis, research and therapy, including but not limited to, cancer markers. In particular, the present invention relates to recurrent gene fusions as diagnostic markers and clinical targets for hemangiopericytoma.

BACKGROUND OF THE INVENTION

A central aim in cancer research is to identify altered genes that are causally implicated in oncogenesis. Several types of somatic mutations have been identified, including base substitutions, insertions, deletions, translocations, and chromosomal gains and losses, all of which result in altered activity of an oncogene or tumor suppressor gene. First hypothesized in the early 1900's, there is now compelling evidence for a causal role for chromosomal rearrangements in cancer (Rowley, *Nat Rev Cancer* 1: 245 (2001)). Reccurent chromosomal aberrations were thought to be primarily characteristic of leukemias, lymphomas, and sarcomas. Epithelial tumors (carcinomas), which are much more common and contribute to a relatively large fraction of the morbidity and mortality associated with human cancer, comprise less than 1% of the known, disease-specific chromosomal rearrangements (Mitelman, *Mutat Res* 462: 247 (2000)). While hematological malignancies are often characterized by balanced, disease-specific chromosomal rearrangements, most solid tumors have a plethora of non-specific chromosomal aberrations. It is thought that the karyotypic complexity of solid tumors is due to secondary alterations acquired through cancer evolution or progression.

Two primary mechanisms of chromosomal rearrangements have been described. In one mechanism, promoter/enhancer elements of one gene are rearranged adjacent to a proto-oncogene, thus causing altered expression of an oncogenic protein. This type of translocation is exemplified by the apposition of immunoglobulin (IG) and T-cell receptor (TCR) genes to MYC leading to activation of this oncogene in B- and T-cell malignancies, respectively (Rabbitts, *Nature* 372: 143 (1994)). In the second mechanism, rearrangement results in the fusion of two genes, which produces a fusion protein that may have a new function or altered activity. The prototypic example of this translocation is the BCR-ABL gene fusion in chronic myelogenous leukemia (CML) (Rowley, *Nature* 243: 290 (1973); de Klein et al., *Nature* 300: 765 (1982)). Importantly, this finding led to the rational development of imatinib mesylate (Gleevec), which successfully targets the BCR-ABL kinase (Deininger et al., *Blood* 105: 2640 (2005)). Thus, identifying recurrent gene rearrangements in common epithelial tumors may have profound implications for cancer drug discovery efforts as well as patient treatment.

SUMMARY OF THE INVENTION

Provided herein are kits, compositions and methods for cancer diagnosis, research and therapy, including but not limited to, cancer markers. In particular, the present invention relates to recurrent gene fusions as diagnostic markers and clinical targets for hemangiopericytoma.

For example, in some embodiments, the present invention provides a kit for detecting gene fusions associated with solitary fibrous tumor or hemangiopericytoma (SFT/HPC) in a subject, comprising or consisting essentially of or consisting of: at least a first gene fusion informative reagent for identification of a NGFI-A binding protein 2-signal transducer and activator of transcription 6, interleukin-4 induced (NAB2-STAT6) gene fusion. The present invention is not limited to a particular regent(s). Examples include but are not limited to, a probe that specifically hybridizes to the fusion junction of a NAB2-STAT6 gene fusion, a pair of primers that amplify a fusion junction of a NAB2-STAT6 gene fusion (e.g., a first primer that hybridizes to a NAB2 nucleic acid and second primer that hybridizes to a STAT6 nucleic acid), an antibody that binds to the fusion junction of a NAB2-STAT6 fusion polypeptide, a sequencing primer that binds to a NAB2-STAT6 fusion and generates an extension product that spans the fusion junction of said NAB2-STAT6 gene fusion, or a pair of probes wherein the first probe hybridizes to NAB2 and the second probe hybridizes to an STAT6 gene. In some embodiments, the reagent is labeled.

Further embodiments of the present invention provide uses and methods for diagnosing SFT/HPC in a subject using the aforementioned kits or other components. For example, in some embodiments, the present invention provides a method for diagnosing solitary fibrous tumor or hemangiopericytoma (SFT/HPC) in a subject, comprising: (a) contacting a biological sample from a subject with a nucleic acid or polypeptide detection assay comprising at least a first gene fusion informative reagent for identification of a NGFI-A binding protein 2-signal transducer and activator of transcription 6, interleukin-4 induced (NAB2-STAT6) gene fusion under conditions that the presence of a NGFI-A binding protein 2-signal transducer and activator of transcription 6, interleukin-4 induced (NAB2-STAT6) gene fusion is detected; and (b) diagnosing SFT/HPC in the subject when the NAB2-STAT6 gene fusion gene fusion is present in the sample. In some embodiments, the NAB2-STAT6 gene fusion comprises the early growth response (EGR) binding domain of the NAB2 gene fused to the activation domain of the STAT6 gene. In some embodiments, step (a) comprises detecting chromosomal rearrangements of genomic DNA having a 5' portion from NAB2 and a 3' portion from STAT6. In some embodiments, step (a) comprises detecting chromosomal rearrangements of genomic DNA using a nucleic acid sequencing technique. In some embodiments, step (a) comprises detecting chromosomal rearrangements of genomic DNA using a nucleic acid hybridization technique. In some embodiments, step (a) comprises detecting chromosomal rearrangements of genomic DNA using a nucleic acid hybridization technique (e.g., including but not limited to, in situ hybridization (ISH), microarray or Southern blot). In some embodiments, step (a) comprises detecting chromosomal rearrangements of genomic DNA using a nucleic acid amplification method (e.g., including but not limited to, polymerase chain reaction (PCR), reverse transcription polymerase chain reaction (RT-PCR), transcription-mediated amplification (TMA), ligase chain reaction (LCR), strand displacement amplification (SDA), or nucleic acid sequence based amplification (NASBA)). In some embodiments, step (a) comprises detecting chimeric mRNA transcripts having 5' portion from NAB2 and a 3' portion from STAT6. In some embodiments, step (a) comprises detecting chimeric mRNA transcripts using a nucleic acid sequencing technique. In some embodiments, step (a) comprises detecting chimeric mRNA transcripts using a nucleic acid hybridization technique. In some embodiments, step (a) comprises detecting chimeric mRNA transcripts using a nucleic acid hybridization technique (e.g., including but not limited to, in situ hybridization (ISH), microarray or Northern blot). In some embodiments, step (a) comprises detecting chimeric mRNA transcripts using a nucleic acid amplification method (e.g., including but not limited to, polymerase chain reaction (PCR), reverse transcription polymerase chain reaction (RT-PCR), transcription-mediated amplification (TMA), ligase chain reaction (LCR), strand displacement amplification (SDA), or nucleic acid sequence based amplification (NASBA)). In some embodiments, the method further comprised the step of collecting the sample from the subject. In some embodiments, the sample is, for example, tissue, blood, plasma, serum, or cells.

Additional embodiments of the present invention are provided in the description and examples below.

DESCRIPTION OF THE FIGURES

FIG. 8 shows relative expression of STAT6 in SFT tumors as measured by Affymetrix U133A microarray analysis across a panel of soft tissue sarcomas. SFT, solitary fibrous tumor; CCS, clear cell sarcoma; FS, fibrosarcoma; LMS, leiomyosarcoma; MFH, malignant fibrous histiocytoma; MLS, myxoid liposarcoma; SS, synovial sarcoma.

DEFINITIONS

Figure 1:
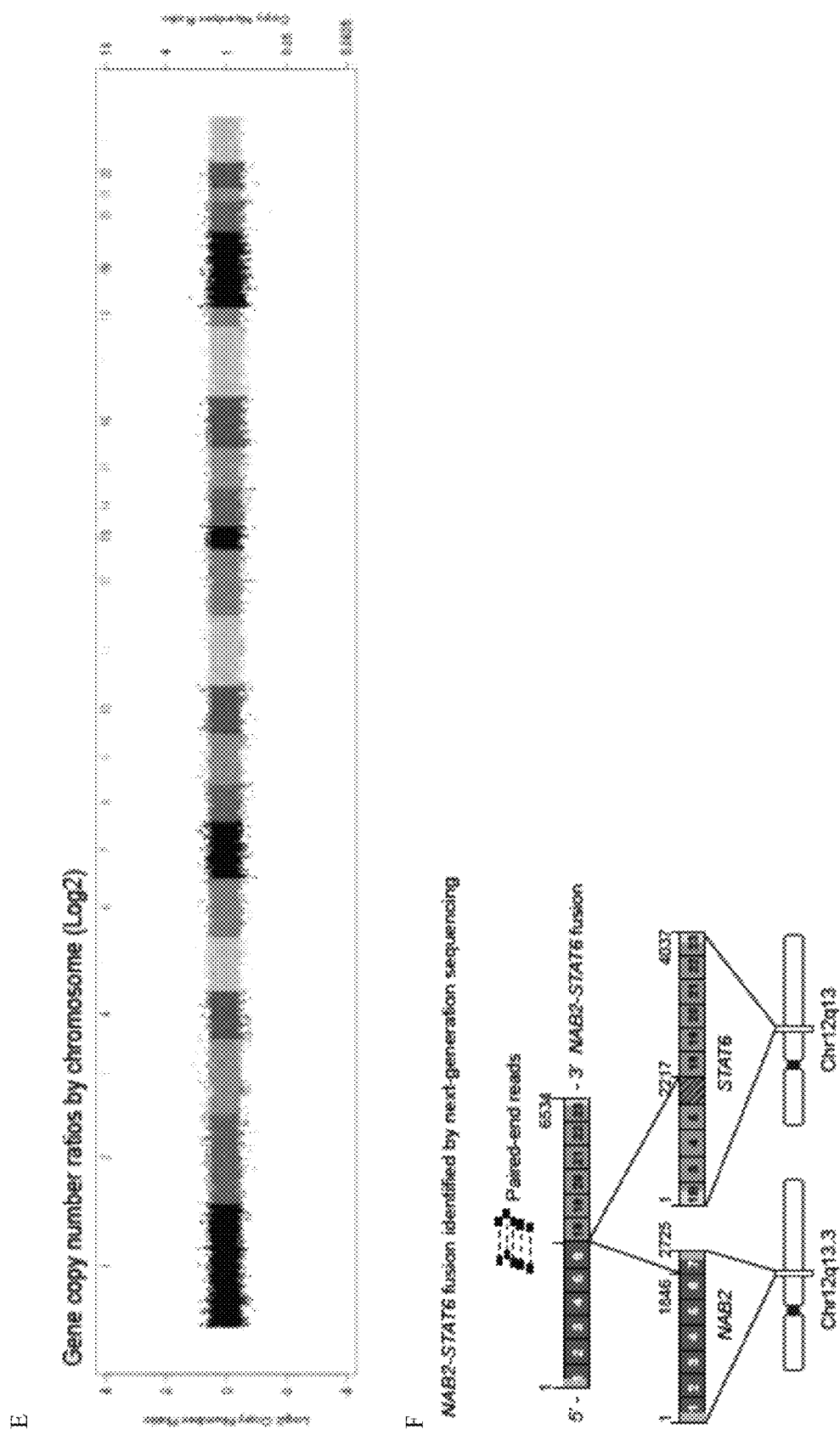
FIG. 1 shows integrative sequencing and mutational analysis of patient MO_1005 (SFT index case). A, A schematic of the workflow for the clinical sequencing protocol (MI-ONCOSEQ) in which the index patient (MO_1005) was enrolled. B, CT image of the liver metastasis that was biopsied. Arrow indicates metastasis that was biopsied. C, Pathologic features of index case (left and middle panels) and immunoreactivity for CD34 (right panel). D, Nonsynonymous somatic point mutations detected in the index case as determined by whole exome sequencing of the tumor and matched germline. E, Gene copy number landscape of the index case as assessed by whole exome sequencing matched to germline. F, Schematic of the NAB2-STAT6 gene fusion detected in the index case by paired-end transcriptome sequencing.

To facilitate an understanding of the present invention, a number of terms and phrases are defined below:

As used herein, the term "gene fusion" refers to a chimeric genomic DNA, a chimeric messenger RNA, a truncated protein or a chimeric protein resulting from the fusion of at least a portion of a first gene to at least a portion of a second gene. The gene fusion need not include entire genes or exons of genes.

As used herein, the term "sensitivity" is defined as a statistical measure of performance of an assay (e.g., method, test), calculated by dividing the number of true positives by the sum of the true positives and the false negatives.

As used herein, the term "specificity" is defined as a statistical measure of performance of an assay (e.g., method, test), calculated by dividing the number of true negatives by the sum of true negatives and false positives.

As used herein, the term "informative" or "informativeness" refers to a quality of a marker or panel of markers, and specifically to the likelihood of finding a marker (or panel of markers) in a positive sample.

As used herein, the terms "SFT/HPC informative reagent" refers to a reagent or reagents that are informative for identification of gene fusions described herein. In some embodiments, reagents are primers, probes or antibodies for detection of NAB2-STAT6 gene fusions described herein As used herein, the term "transcriptional regulatory region" refers to the non-coding upstream regulatory sequence of a gene, also called the 5' untranslated region (5'UTR).

As used herein, the terms "detect", "detecting", or "detection" may describe either the general act of discovering or discerning or the specific observation of a detectably labeled composition.

As used herein, the term "inhibits at least one biological activity of a gene fusion" refers to any agent that decreases any activity of a gene fusion of the present invention (e.g., including, but not limited to, the activities described herein), via directly contacting gene fusion protein, contacting gene fusion mRNA or genomic DNA, causing conformational changes of gene fusion polypeptides, decreasing gene fusion protein levels, or interfering with gene fusion interactions with signaling partners, and affecting the expression of gene fusion target genes. Inhibitors also include molecules that indirectly regulate gene fusion biological activity by intercepting upstream signaling molecules.

As used herein, the term "siRNAs" refers to small interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to, or substantially complementary to, a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment is retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under 'medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1× SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0× SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

Numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the conditions that promote hybridization under conditions of high stringency (e.g., increasing the temperature of the hybridization and/or wash steps, the use of formamide in the hybridization solution, etc.) (see definition above for "stringency") can be utilized.

As used herein, the term "amplification oligonucleotide" refers to an oligonucleotide that hybridizes to a target nucleic acid, or its complement, and participates in a nucleic acid amplification reaction. An example of an amplification oligonucleotide is a "primer" that hybridizes to a template nucleic acid and contains a 3' OH end that is extended by a polymerase in an amplification process. Another example of an amplification oligonucleotide is an oligonucleotide that is not extended by a polymerase (e.g., because it has a 3' blocked end) but participates in or facilitates amplification. Amplification oligonucleotides may optionally include modified nucleotides or analogs, or additional nucleotides that participate in an amplification reaction but are not complementary to or contained in the target nucleic acid. Amplification oligonucleotides may contain a sequence that is not complementary to the target or template sequence. For example, the 5' region of a primer may include a promoter sequence that is non-complementary to the target nucleic acid (referred to as a "promoter-primer"). Those skilled in the art will understand that an amplification oligonucleotide that functions as a primer may be modified to include a 5' promoter sequence, and thus function as a promoter-primer. Similarly, a promoter-primer may be modified by removal of, or synthesis without, a promoter sequence and still function as a primer. A 3' blocked amplification oligonucleotide may provide a promoter sequence and serve as a template for polymerization (referred to as a "promoter-provider").

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to at least a portion of another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

DETAILED DESCRIPTION OF THE INVENTION

Provided herein are kits, compositions and methods for cancer diagnosis, research and therapy, including but not limited to, cancer markers. In particular, the present invention relates to recurrent gene fusions as diagnostic markers and clinical targets for hemangiopericytoma.

Advances in high-throughput sequencing technologies will soon make it possible to define the molecular taxonomy of a spectrum of human diseases and facilitate a move towards "precision medicine". With regards to oncology, defining the mutational landscape of an individual patient's tumor leads to the more precise treatment and management of cancer patients. Comprehensive clinical sequencing programs for cancer patients have been initiated at a variety of medical centers (Roychowdhury et al., Sci Transl Med 2011; 3:111ra21; Ruiz et al., Proc Natl Acad Sci USA 2011; 108:12054-9; Welch et al. JAMA 2011; 305:1577-84). In addition to the identification of "actionable" therapeutic targets in cancer patients, these clinical sequencing efforts may lead to the identification of novel "driver" mutations that are relatively rare in a common cancer type or be newly revealed in relatively rare cancer types.

Cellular solitary fibrous tumor/hemangiopericytoma (SFT/HPC) represents a wide spectrum of tumor types of mesenchymal origin that can affect virtually any region of the body (Park et al., Curr Opin Oncol 2009; 21:327-31). SFT is composed of CD34-positive fibroblastic-appearing cells, arranged in a distinctive patternless growth of alternating cellularity and collagenous stroma. HPC, previously regarded as a distinct entity, displays a more uniform cellularity (resembling the cellular areas of SFT) and a prominent "stag-horn" vascular network. Due to its considerable morphological overlap and similar CD34 reactivity, HPC has been reclassified as a histologic variant of SFT (Guillou et al., Extrapleural solitary fibrous tumour and haemangiopericytoma. Pathology and genetics of tumours of soft tissue and bone. Lyon: IARC Press; 2002). While most SFTs are benign and can be cured with surgery, 15-20% of patients progress with either local recurrence or distant metastases, which can be difficult to treat (Park et al., supra; Gold et al., Cancer 2002; 94:1057-68).

Several cytogenetic reports have suggested gains or losses in several chromosomes, as well as structural rearrangements in 4q13, 9p22-9p23, 12q24, 12q13-12q15, however no highly recurrent abnormality has been found across the spectrum of SFTs (Debiec-Rychter et al., Cancer Genet Cytogenet 2001; 131:69-73). A study by Mitelman and colleagues observed recurrent rearrangement at the 12q13 locus in a subgroup of HPCs (Cancer 1993; 71:3009-13). Previous studies provide a role for IGF2 overexpression in the pathogenesis of these tumors, implicated in triggering hypoglycemia in some patients (Hajdu et al., J Pathol 2010; 221:300-7; Li et al., J Pathol 2007; 211:550-4). By gene expression profiling, SFTs exhibit a distinct signature of overexpressed tyrosine kinases compared to other sarcoma types, however no molecular subgroups emerged based on anatomic site (Hajdu et al., supra). Thus, it is unclear whether SFTs that originate at diverse sites such as the meninges, lung, and breast share a common pathogenesis.

During experiments conducted during the course of development of embodiments of the present invention, the NAB2-STAT6 fusion was identified by transcriptome sequencing of the index SFT patient MO_1005. This finding was corroborated by exome copy number data indicating a focal 5' deletion in the STAT6 genomic locus. The index case was relatively silent in terms of point mutations and copy number aberrations further supporting the notion that NAB2-STAT6 serves as a driver mutation. Long distance genomic PCR confirmed the existence of this fusion at the DNA level.

Recurrence analysis on an independent set of tumor samples indicated that nearly all SFTs (100% in this study) harbor a NAB2-STAT6 fusion. This indicates that the NAB2-STAT6 gene fusion is pathognomonic for SFT and that the spectrum of SFT characteristics and morphology have a common genetic origin. A NAB2-STAT6 fusion assessment finds use as a genetic marker in sarcoma cases that are not unambiguously classified as SFT (e.g. cases of CD34-negative SFT, and malignant and de-differentiated SFT) (Mosquera and Fletcher, Am J Surg Pathol 2009; 33:1314-21). While there are varied fusion protein structures in individual SFT patients, all fusions exhibit a truncation of the transcriptional repressor domain of NAB2 with an in-frame fusion to the transcriptional activation domain of STAT6 (although additional STAT6 domains may be included). The truncation of the repressor domain likely attenuates its repressive activity, while addition of a strong, intact activation domain engenders transcriptional activation potential.

Figure 4:
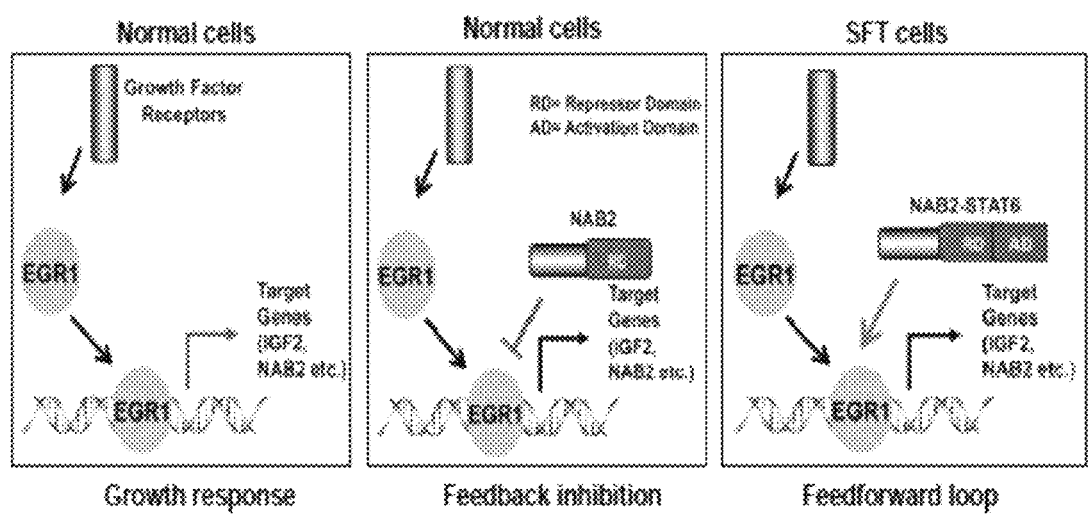
FIG. 4 shows a model for the function of the NAB2-STAT6 gene fusion in SFT. A, Schematic model of NAB2 and EGR1 signaling loops. B, Outlier gene expression in SFT predicted to be the result of the NAB2-STAT6 constitutive activation of EGR1 mediated pathways.
Figure 4:
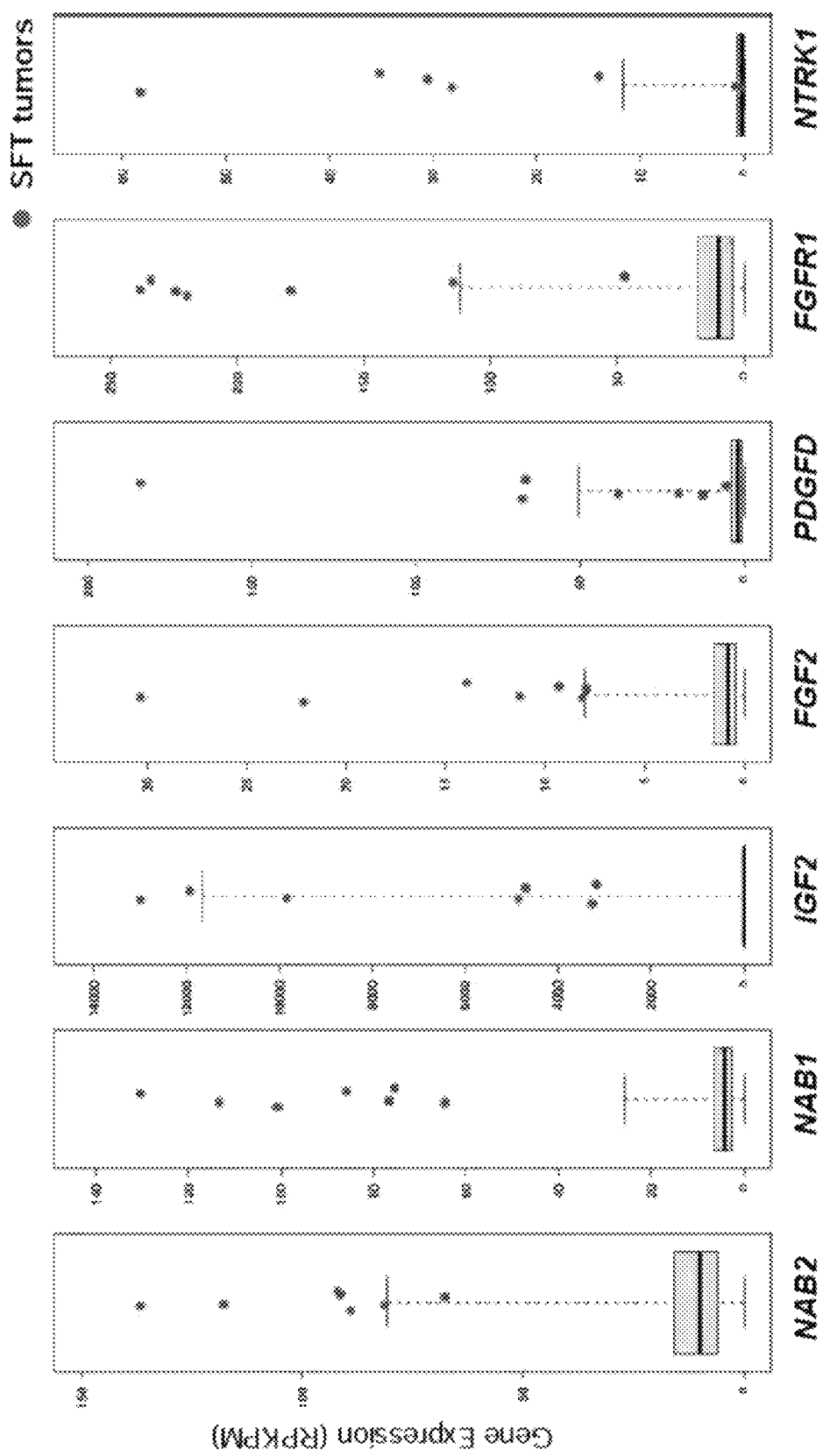

NAB2 is a well-known co-regulator of the EGR transcription factors 19 and all of the SFT fusion proteins maintain an intact N-terminal EGR binding domain (EBD). EGR1 is a zinc finger transcription factor which couples growth factor signaling with induction of nuclear programs of differentiation and proliferation mediated by EGR1 target genes (FIG. 4A) (Thiel et al., J Cell Physiol 2002; 193:287-92). As part of a homeostatic loop, NAB2 is induced by EGR family members and functions in a negative feedback manner to repress their activity (Kumbrink et al., J Biol Chem 2005; 280:42785-93; Kumbrink et al., J Cell Biochem 2010; 111:207-17). Milbrandt and colleagues showed that engineered mutations in NAB2, defective in their ability to bind EGR1 (e.g., mutation in the EBD), actually have a dominant negative effect and promote EGR1 mediated transcription (Svaren et al., EMBO J. 998; 17:6010-9). In the context of SFT, the NAB2 fusion inherits an activation domain from the signaling molecule STAT6, which converts a transcriptional repressor (NAB2) into a potent transcriptional activator (NAB2-STAT6) of EGR1. This leads to constitutive activation of EGR mediated transcription culminating in a feedforward loop that drives neoplastic progression. This hypothesis was further explored by comparing the RNA-Seq analysis of the 7 SFTs sequenced in this study with 282 other tumors. It was found that EGR target genes including NAB2, NAB1, IGF2, FGF2, PDGFD, and receptor tyrosine kinases like FGFR1 and NTRK1, all exhibited outlier levels in SFTs relative to other tumor types (FIG. 4B). A number of kinases including FGFR1 are targets of EGR1 and are also overexpressed in SFT and can be explained by the feedforward loop potentiated by the NAB2-STAT6 fusion.

I. Gene Fusions

Embodiments of the present invention provide diagnostic, screening, research, and therapeutic method of diagnosing and characterizing cancer (e.g., SFT/HPC) based on the presence of NAB2-STAT6 gene fusions in a sample. In some embodiments, gene fusions comprise the early growth response (EGR) binding domain of the NAB2 gene fused to the activation domain of the STAT6 gene, although other regions are specifically encopossed by embodiments of the present invention.

II. Antibodies

The gene fusion proteins of the present invention, including fragments, derivatives and analogs thereof, may be used as immunogens to produce antibodies having use in the diagnostic, research, and therapeutic methods described below. The antibodies may be polyclonal or monoclonal, chimeric, humanized, single chain or Fab fragments. Various procedures may be used for the production and labeling of such antibodies and fragments. See, e.g., Burns, ed., *Immunochemical Protocols*, 3$^{rd}$ ed., Humana Press (2005); Harlow and Lane, *Antibodies: A Laboratory Manual*, Cold Spring Harbor Laboratory (1988); Kozbor et al., *Immunology Today* 4: 72 (1983); Köhler and Milstein, *Nature* 256: 495 (1975).

III. Diagnostic Applications

The present invention provides DNA, RNA and protein based diagnostic methods that either directly or indirectly detect the gene fusions. The present invention also provides compositions and kits for diagnostic purposes.

The diagnostic methods of the present invention may be qualitative or quantitative. Quantitative diagnostic methods may be used, for example, to discriminate between indolent and aggressive cancers via a cutoff or threshold level. Where applicable, qualitative or quantitative diagnostic methods may also include amplification of target, signal or intermediary (e.g., a universal primer).

An initial assay may confirm the presence of a gene fusion but not identify the specific fusion. A secondary assay is then performed to determine the identity of the particular fusion, if desired. The second assay may use a different detection technology than the initial assay.

The gene fusions of embodiments of the present invention may be detected along with other markers in a multiplex or panel format. Markers are selected for their predictive value alone or in combination with the gene fusions. Markers for other cancers, diseases, infections, and metabolic conditions are also contemplated for inclusion in a multiplex of panel format.

The diagnostic methods of embodiments of the present invention may also be modified with reference to data correlating particular gene fusions with the stage, aggressiveness or progression of the disease or the presence or risk of metastasis. Ultimately, the information provided by the methods of the present invention will assist a physician in choosing the best course of treatment for a particular patient.

A. Sample

Any patient sample suspected of containing the gene fusions may be tested according to the methods of the present invention. By way of non-limiting examples, the sample may be tissue (e.g., a biopsy sample), blood, or a fraction thereof (e.g., plasma, serum, or cells).

In some embodiments, the patient sample typically requires preliminary processing designed to isolate or enrich the sample for the gene fusions or cells that contain the gene fusions. A variety of techniques may be used for this purpose, including but not limited: centrifugation; immunocapture; cell lysis; and, nucleic acid target capture.

B. DNA and RNA Detection

The gene fusions of the present invention may be detected as chromosomal rearrangements of genomic DNA or chimeric mRNA using a variety of nucleic acid techniques, including but not limited to: nucleic acid sequencing; nucleic acid hybridization; and, nucleic acid amplification.

1. Sequencing

Illustrative non-limiting examples of nucleic acid sequencing techniques include, but are not limited to, chain terminator (Sanger) sequencing and dye terminator sequencing. Those of ordinary skill in the art will recognize that because RNA is less stable in the cell and more prone to nuclease attack experimentally RNA is usually reverse transcribed to DNA before sequencing.

Chain terminator sequencing uses sequence-specific termination of a DNA synthesis reaction using modified nucleotide substrates. Extension is initiated at a specific site on the template DNA by using a short radioactive, fluorescent or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

Some embodiments of the present invention utilize next generation or high-throughput sequencing. A variety of nucleic acid sequencing methods are contemplated for use in the methods of the present disclosure including, for example, chain terminator (Sanger) sequencing, dye terminator sequencing, and high-throughput sequencing methods. See, e.g., Sanger et al., Proc. Natl. Acad. Sci. USA 74:5463-5467 (1997); Maxam et al., Proc. Natl. Acad. Sci. USA 74:560-564 (1977); Drmanac, et al., Nat. Biotechnol. 16:54-58 (1998); Kato, Int. J. Clin. Exp. Med. 2:193-202 (2009); Ronaghi et al., Anal. Biochem. 242:84-89 (1996); Margulies et al., Nature 437:376-380 (2005); Ruparel et al., Proc. Natl. Acad. Sci. USA 102:5932-5937 (2005), and Harris et al., Science 320:106-109 (2008); Levene et al., Science 299: 682-686 (2003); Korlach et al., Proc. Natl. Acad. Sci. USA 105:1176-1181 (2008); Branton et al., Nat. Biotechnol. 26(10):1146-53 (2008); Eid et al., Science 323:133-138 (2009); each of which is herein incorporated by reference in its entirety.

In some embodiments, sequencing technology including, but not limited to, pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. Morozova and Marra provide a review of some such technologies in *Genomics*, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

A number of DNA sequencing techniques can be used including fluorescence-based sequencing methodologies (See, e.g., Birren et al., Genome Analysis: Analyzing DNA, 1, Cold Spring Harbor, N.Y.; herein incorporated by reference in its entirety). In some embodiments, the technology finds use in automated sequencing techniques understood in that art. In some embodiments, the present technology finds use in parallel sequencing of partitioned amplicons (PCT Publication No: WO2006084132 to Kevin McKernan et al., herein incorporated by reference in its entirety). In some embodiments, the technology finds use in DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques in which the technology finds use include the Church polony technology (Mitra et al., 2003, Analytical Biochemistry 320, 55-65; Shendure et al., 2005 Science 309, 1728-1732; U.S. Pat. No. 6,432,360, U.S. Pat. No. 6,485,944, U.S. Pat. No. 6,511,803; herein incorporated by reference in their entireties), the 454 picoliter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. No. 6,787,308; U.S. Pat. No. 6,833,246;

herein incorporated by reference in their entireties), the Lynx massively parallel signature sequencing technology (Brenner et al. (2000). Nat. Biotechnol. 18:630-634; U.S. Pat. No. 5,695,934; U.S. Pat. No. 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., *Clinical Chem.*, 55: 641-658, 2009; MacLean et al., *Nature Rev. Microbiol.*, 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., Life Technologies/Ion Torrent, and Pacific Biosciences, respectively.

In pyrosequencing (Voelkerding et al., *Clinical Chem.*, 55: 641-658, 2009; MacLean et al., *Nature Rev. Microbiol.*, 7: 287-296; U.S. Pat. No. 6,210,891; U.S. Pat. No. 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picoliter plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., *Clinical Chem.*, 55: 641-658, 2009; MacLean et al., *Nature Rev. Microbiol.*, 7: 287-296; U.S. Pat. No. 6,833,246; U.S. Pat. No. 7,115,400; U.S. Pat. No. 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., *Clinical Chem.*, 55: 641-658, 2009; MacLean et al., *Nature Rev. Microbiol.*, 7: 287-296; U.S. Pat. No. 5,912,148; U.S. Pat. No. 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, the technology finds use in nanopore sequencing (see, e.g., Astier et al., J. Am. Chem. Soc. 2006 Feb. 8; 128(5):1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, the technology finds use in HeliScope by Helicos BioSciences (Voelkerding et al., *Clinical Chem.*, 55: 641-658, 2009; MacLean et al., *Nature Rev. Microbiol.*, 7: 287-296; U.S. Pat. No. 7,169,560; U.S. Pat. No. 7,282,337; U.S. Pat. No. 7,482,120; U.S. Pat. No. 7,501,245; U.S. Pat. No. 6,818,395; U.S. Pat. No. 6,911,345; U.S. Pat. No. 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the Ion Torrent sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs.

The technology finds use in another nucleic acid sequencing approach developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other emerging single molecule sequencing methods include real-time sequencing by synthesis using a VisiGen platform (Voelkerding et al., Clinical Chem., 55: 641-58, 2009; U.S. Pat. No. 7,329,492; U.S. patent application Ser. No. 11/671,956; U.S. patent application Ser. No. 11/781, 166; each herein incorporated by reference in their entirety) in which immobilized, primed DNA template is subjected to strand extension using a fluorescently-modified polymerase and florescent acceptor molecules, resulting in detectable fluorescence resonance energy transfer (FRET) upon nucleotide addition.

In some embodiments, capillary electrophoresis (CE) is utilized to analyze amplification fragments. During capillary electrophoresis, nucleic acids (e.g., the products of a PCR reaction) are injected electrokinetically into capillaries filled with polymer. High voltage is applied so that the fluorescent DNA fragments are separated by size and are detected by a laser/camera system. In some embodiments, CE systems from Life Technologies (Grand Island, N.Y.) are utilized for fragment sizing (See e.g., U.S. Pat. No. 6,706,162, U.S. Pat. No. 8,043,493, each of which is herein incorporated by reference in its entirety).

2. Hybridization

Illustrative non-limiting examples of nucleic acid hybridization techniques include, but are not limited to, in situ hybridization (ISH), microarray, and Southern or Northern blot.

In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

2.1 FISH

In some embodiments, fusion sequences are detected using fluorescence in situ hybridization (FISH). The preferred FISH assays for the present invention utilize bacterial artificial chromosomes (BACs). These have been used extensively in the human genome sequencing project (see Nature 409: 953-958 (2001)) and clones containing specific BACs are available through distributors that can be located through many sources, e.g., NCBI. Each BAC clone from the human genome has been given a reference name that unambiguously identifies it. These names can be used to find a corresponding GenBank sequence and to order copies of the clone from a distributor. In some embodiments, the detection assay is a FISH assay utilizing a probe for NAB2 and/or STAT6.

2.2 Microarrays

Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink jet printing; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

3. Amplification

Chromosomal rearrangements of genomic DNA and chimeric mRNA may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800,159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399, 491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαs to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *BioTechnol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

4. Detection Methods

Non-amplified or amplified gene fusion nucleic acids can be detected by any means. For example, the gene fusions can be detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification including methods disclosed in U.S. Pat. Nos. 6,303,305 and 6,541,205, each of which is herein incorporated by reference in its entirety can be used. Another method for determining the quantity of target sequence initially present in a sample, but which is not based on a real-time amplification, is disclosed in U.S. Pat. No. 5,710, 029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, herein incorporated by reference in its entirety.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DAB-CYL and EDANS). Molecular beacons are disclosed in U.S. Pat. Nos. 5,925,517 and 6,150,097, herein incorporated by reference in its entirety.

Other self-hybridizing are, for example, probe binding pairs having interacting labels, such as those disclosed in U.S. Pat. No. 5,928,862 (herein incorporated by reference in its entirety) might be adapted for use in the present invention. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products in the present invention. See, e.g., U.S. Pat. No. 5,814,447 (herein incorporated by reference in its entirety).

C. Protein Detection

The gene fusions of the present invention may be detected as truncated or chimeric proteins using a variety of protein techniques, including but not limited to: protein sequencing; and, immunoassays.

1. Sequencing

Illustrative non-limiting examples of protein sequencing techniques include, but are not limited to, mass spectrometry and Edman degradation.

Mass spectrometry can, in principle, sequence any size protein but becomes computationally more difficult as size increases. A protein is digested by an endoprotease, and the resulting solution is passed through a high pressure liquid chromatography column. At the end of this column, the solution is sprayed out of a narrow nozzle charged to a high positive potential into the mass spectrometer. The charge on the droplets causes them to fragment until only single ions remain. The peptides are then fragmented and the mass-charge ratios of the fragments measured. The mass spectrum is analyzed by computer and often compared against a database of previously sequenced proteins in order to determine the sequences of the fragments. The process is then repeated with a different digestion enzyme, and the overlaps in sequences are used to construct a sequence for the protein.

In the Edman degradation reaction, the peptide to be sequenced is adsorbed onto a solid surface (e.g., a glass fiber coated with polybrene). The Edman reagent, phenylisothiocyanate (PTC), is added to the adsorbed peptide, together with a mildly basic buffer solution of 12% trimethylamine, and reacts with the amine group of the N-terminal amino acid. The terminal amino acid derivative can then be selectively detached by the addition of anhydrous acid. The derivative isomerizes to give a substituted phenylthiohydantoin, which can be washed off and identified by chromatography, and the cycle can be repeated. The efficiency of each step is about 98%, which allows about 50 amino acids to be reliably determined.

2. Immunoassays

Illustrative non-limiting examples of immunoassays include, but are not limited to: immunoprecipitation; Western blot; ELISA; immunohistochemistry; immunocytochemistry; flow cytometry; and, immuno-PCR. Polyclonal or monoclonal antibodies detectably labeled using various techniques (e.g., colorimetric, fluorescent, chemiluminescent or radioactive) are suitable for use in the immunoassays.

Immunoprecipitation is the technique of precipitating an antigen out of solution using an antibody specific to that antigen. The process can be used to identify protein complexes present in cell extracts by targeting a protein believed to be in the complex. The complexes are brought out of solution by insoluble antibody-binding proteins isolated initially from bacteria, such as Protein A and Protein G. The antibodies can also be coupled to sepharose beads that can easily be isolated out of solution. After washing, the precipitate can be analyzed using mass spectrometry, Western blotting, or any number of other methods for identifying constituents in the complex.

A Western blot, or immunoblot, is a method to detect protein in a given sample of tissue homogenate or extract. It uses gel electrophoresis to separate denatured proteins by mass. The proteins are then transferred out of the gel and onto a membrane, typically polyvinyldifluoride or nitrocellulose, where they are probed using antibodies specific to the protein of interest. As a result, researchers can examine the amount of protein in a given sample and compare levels between several groups.

An ELISA, short for Enzyme-Linked ImmunoSorbent Assay, is a biochemical technique to detect the presence of an antibody or an antigen in a sample. It utilizes a minimum of two antibodies, one of which is specific to the antigen and the other of which is coupled to an enzyme. The second antibody will cause a chromogenic or fluorogenic substrate to produce a signal. Variations of ELISA include sandwich ELISA, competitive ELISA, and ELISPOT. Because the ELISA can be performed to evaluate either the presence of antigen or the presence of antibody in a sample, it is a useful tool both for determining serum antibody concentrations and also for detecting the presence of antigen.

Immunohistochemistry and immunocytochemistry refer to the process of localizing proteins in a tissue section or cell, respectively, via the principle of antigens in tissue or cells binding to their respective antibodies. Visualization is enabled by tagging the antibody with color producing or fluorescent tags. Typical examples of color tags include, but are not limited to, horseradish peroxidase and alkaline phosphatase. Typical examples of fluorophore tags include, but are not limited to, fluorescein isothiocyanate (FITC) or phycoerythrin (PE).

Flow cytometry is a technique for counting, examining and sorting microscopic particles suspended in a stream of fluid. It allows simultaneous multiparametric analysis of the physical and/or chemical characteristics of single cells flowing through an optical/electronic detection apparatus. A beam of light (e.g., a laser) of a single frequency or color is directed onto a hydrodynamically focused stream of fluid. A number of detectors are aimed at the point where the stream passes through the light beam; one in line with the light beam (Forward Scatter or FSC) and several perpendicular to it (Side Scatter (SSC) and one or more fluorescent detectors). Each suspended particle passing through the beam scatters the light in some way, and fluorescent chemicals in the particle may be excited into emitting light at a lower frequency than the light source. The combination of scattered and fluorescent light is picked up by the detectors, and by analyzing fluctuations in brightness at each detector, one for each fluorescent emission peak, it is possible to deduce various facts about the physical and chemical structure of each individual particle. FSC correlates with the cell volume and SSC correlates with the density or inner complexity of the particle (e.g., shape of the nucleus, the amount and type of cytoplasmic granules or the membrane roughness).

Immuno-polymerase chain reaction (IPCR) utilizes nucleic acid amplification techniques to increase signal generation in antibody-based immunoassays. Because no protein equivalence of PCR exists, that is, proteins cannot be replicated in the same manner that nucleic acid is replicated during PCR, the only way to increase detection sensitivity is by signal amplification. The target proteins are bound to antibodies which are directly or indirectly conjugated to oligonucleotides. Unbound antibodies are washed away and the remaining bound antibodies have their oligonucleotides amplified. Protein detection occurs via detection of amplified oligonucleotides using standard nucleic acid detection methods, including real-time methods.

D. Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., likelihood of cancer being present) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

E. In Vivo Imaging

The gene fusions of the present invention may also be detected using in vivo imaging techniques, including but not limited to: radionuclide imaging; positron emission tomography (PET); computerized axial tomography, X-ray or magnetic resonance imaging method, fluorescence detection, and chemiluminescent detection. In some embodiments, in vivo imaging techniques are used to visualize the presence of or expression of cancer markers in an animal (e.g., a human or non-human mammal). For example, in some embodiments, cancer marker mRNA or protein is labeled using a labeled antibody specific for the cancer marker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the cancer markers of the present invention are described below.

The in vivo imaging methods of the present invention are useful in the diagnosis of cancers that express the cancer markers of the present invention. In vivo imaging is used to visualize the presence of a marker indicative of the cancer. Such techniques allow for diagnosis without the use of an unpleasant biopsy. The in vivo imaging methods of the present invention are also useful for providing prognoses to cancer patients. For example, the presence of a marker indicative of cancers likely to metastasize can be detected. The in vivo imaging methods of the present invention can further be used to detect metastatic cancers in other parts of the body.

In some embodiments, reagents (e.g., antibodies) specific for the cancer markers of the present invention are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107, herein incorporated by reference).

In other embodiments, antibodies are radioactively labeled. Sumerdon et al., (Nucl. Med. Biol 17:247-254 [1990] have described an optimized antibody-chelator for the radioimmunoscintographic imaging of tumors using Indium-111 as the label. Griffin et al., (J Clin One 9:631-640 [1991]) have described the use of this agent in detecting tumors in patients suspected of having recurrent colorectal cancer. Agents with paramagnetic ions as labels for magnetic resonance imaging can be utilized (Lauffer, Magnetic Resonance in Medicine 22:339-342 [1991]). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetium-99m (6 hours), and indium-111 (3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 [1980]) for In-111 and Tc-99m, and by Scheinberg et al. (Science 215:1511 [1982]). Other chelating agents may also be used, but the 1-(p-carboxymethoxybenzyl)EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 [1982]) for labeling of albumin with In-111, but which can be adapted for labeling of antibodies. A suitable method of labeling antibodies with Tc-99m which does not use chelation with DPTA is the pretinning method of Crockford et al., (U.S. Pat. No. 4,323,546, herein incorporated by reference).

A preferred method of labeling immunoglobulins with Tc-99m is that described by Wong et al. (Int. J. Appl. Radiat. Isot., 29:251 [1978]) for plasma protein, and recently applied successfully by Wong et al. (J. Nucl. Med., 23:229 [1981]) for labeling antibodies.

In the case of the radiometals conjugated to the specific antibody, it is likewise desirable to introduce as high a proportion of the radiolabel as possible into the antibody molecule without destroying its immunospecificity. A further improvement may be achieved by effecting radiolabeling in the presence of the specific cancer marker of the present invention, to insure that the antigen binding site on the antibody will be protected. The antigen is separated after labeling.

In still further embodiments, in vivo biophotonic imaging (Xenogen, Almeda, Calif.) is utilized for in vivo imaging. This real-time in vivo imaging utilizes luciferase. The luciferase gene is incorporated into cells, microorganisms, and animals (e.g., as a fusion protein with a cancer marker of the present invention). When active, it leads to a reaction that emits light. A CCD camera and software is used to capture the image and analyze it.

F. Compositions & Kits

Compositions for use in the diagnostic methods of the present invention include, but are not limited to, probes, amplification oligonucleotides, and antibodies. Particularly preferred compositions detect a product only when a NAB2-STAT6 fusion is present in a sample. These compositions include: a single labeled probe comprising a sequence that hybridizes to the junction at which a 5' portion from a NAB2 fuses to a 3' portion from a STAT6 gene (i.e., spans the gene fusion junction); a pair of amplification oligonucleotides wherein the first amplification oligonucleotide comprises a sequence that hybridizes to NAB2 and the second amplification oligonucleotide comprises a sequence that hybridizes to STAT6 gene; an antibody to a NAB2-STAT6 fusion.

Other useful compositions, however, include: a pair of labeled probes wherein the first labeled probe comprises a sequence that hybridizes to NAB2 and a second labeled probe comprises a sequence that hybridizes to an STAT6 gene.

Any of these compositions, alone or in combination with other compositions of the present invention, may be provided in the form of a kit. For example, the single labeled probe and pair of amplification oligonucleotides may be provided in a kit for the amplification and detection of gene fusions of the present invention. Kits may further comprise appropriate controls and/or detection reagents.

The probe and antibody compositions of the present invention may also be provided in the form of an array.

IV. Drug Screening Applications

In some embodiments, the present invention provides drug screening assays (e.g., to screen for anticancer drugs). The screening methods of the present invention utilize cancer markers identified using the methods of the present invention (e.g., including but not limited to NAB2-STAT6 gene fusions). For example, in some embodiments, the present invention provides methods of screening for compounds that alter (e.g., decrease) the expression of cancer marker genes. The compounds or agents may interfere with transcription, by interacting, for example, with the promoter region. The compounds or agents may interfere with mRNA produced from the fusion (e.g., by RNA interference, antisense technologies, etc.). The compounds or agents may interfere with pathways that are upstream or downstream of the biological activity of the fusion. In some embodiments, candidate compounds are antisense or interfering RNA agents (e.g., oligonucleotides) directed against cancer markers. In other embodiments, candidate compounds are antibodies or small molecules that specifically bind to a cancer marker regulator or expression products of the present invention and inhibit its biological function.

In one screening method, candidate compounds are evaluated for their ability to alter cancer marker expression by contacting a compound with a cell expressing a cancer marker and then assaying for the effect of the candidate compounds on expression. In some embodiments, the effect of candidate compounds on expression of a cancer marker gene is assayed for by detecting the level of cancer marker mRNA expressed by the cell. mRNA expression can be detected by any suitable method. In other embodiments, the effect of candidate compounds on expression of cancer marker genes is assayed by measuring the level of polypeptide encoded by the cancer markers. The level of polypeptide expressed can be measured using any suitable method, including but not limited to, those disclosed herein.

Specifically, the present invention provides screening methods for identifying modulators, i.e., candidate or test compounds or agents (e.g., proteins, peptides, peptidomimetics, peptoids, small molecules or other drugs) which bind to cancer markers of the present invention, have an inhibitory (or stimulatory) effect on, for example, cancer marker expression or cancer marker activity, or have a stimulatory or inhibitory effect on, for example, the expression or activity of a cancer marker substrate. Compounds thus identified can be used to modulate the activity of target gene products (e.g., cancer marker genes) either directly or indirectly in a therapeutic protocol, to elaborate the biological function of the target gene product, or to identify compounds that disrupt normal target gene interactions. Compounds that inhibit the activity or expression of cancer markers are useful in the treatment of proliferative disorders, e.g., cancer, particularly SFT/HPC cancer.

In one embodiment, the invention provides assays for screening candidate or test compounds that are substrates of a cancer marker protein or polypeptide or a biologically active portion thereof. In another embodiment, the invention provides assays for screening candidate or test compounds that bind to or modulate the activity of a cancer marker protein or polypeptide or a biologically active portion thereof.

The test compounds of the present invention can be obtained using any of the numerous approaches in combinatorial library methods, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364:555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249:404-406 [1990]; Cwirla et al., Proc. Natl. Acad. Sci. 87:6378-6382 [1990]; Felici, J. Mol. Biol. 222:301 [1991]).

VI. Therapeutic Applications

In some embodiments, the present invention provides therapies for cancer (e.g., SFT/HPC). In some embodiments, therapies directly or indirectly target cancer markers (e.g., including but not limited to, NAB2-STAT6 gene fusions).

A. RNA Interference and Antisense Therapies

In some embodiments, the present invention targets the expression of cancer markers. For example, in some embodiments, the present invention employs compositions comprising oligomeric antisense or RNAi compounds, particularly oligonucleotides (e.g., those identified in the drug screening methods described above), for use in modulating the function of nucleic acid molecules encoding cancer markers of the present invention, ultimately modulating the amount of cancer marker expressed.

1. RNA Interference (RNAi)

In some embodiments, RNAi is utilized to inhibit fusion protein function. RNAi represents an evolutionary conserved cellular defense for controlling the expression of foreign genes in most eukaryotes, including humans. RNAi is typically triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g. 21-23 nucleotides in length), and have a base-paired structure characterized by two nucleotide 3'-overhangs. Following the introduction of a small RNA, or RNAi, into the cell, it is believed the sequence is delivered to an enzyme complex called RISC(RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments. In some embodiments, RNAi oligonucleotides are designed to target the junction region of fusion proteins.

Chemically synthesized siRNAs have become powerful reagents for genome-wide analysis of mammalian gene function in cultured somatic cells. Beyond their value for validation of gene function, siRNAs also hold great potential as gene-specific therapeutic agents (Tuschl and Borkhardt, Molecular Intervent. 2002; 2(3):158-67, herein incorporated by reference).

The transfection of siRNAs into animal cells results in the potent, long-lasting post-transcriptional silencing of specific genes (Caplen et al, Proc Natl Acad Sci U.S.A. 2001; 98:9742-7; Elbashir et al., Nature. 2001; 411:494-8; Elbashir et al., Genes Dev. 2001; 15: 188-200; and Elbashir et al., EMBO J. 2001; 20: 6877-88, all of which are herein incorporated by reference). Methods and compositions for performing RNAi with siRNAs are described, for example, in U.S. Pat. No. 6,506,559, herein incorporated by reference.

siRNAs are extraordinarily effective at lowering the amounts of targeted RNA, and by extension proteins, frequently to undetectable levels. The silencing effect can last several months, and is extraordinarily specific, because one nucleotide mismatch between the target RNA and the central region of the siRNA is frequently sufficient to prevent silencing (Brummelkamp et al, Science 2002; 296:550-3; and Holen et al, Nucleic Acids Res. 2002; 30:1757-66, both of which are herein incorporated by reference). An important factor in the design of siRNAs is the presence of accessible sites for siRNA binding. Bahoia et al., (J. Biol. Chem., 2003; 278: 15991-15997; herein incorporated by reference) describe the use of a type of DNA array called a scanning array to find accessible sites in mRNAs for designing effective siRNAs. These arrays comprise oligonucleotides ranging in size from monomers to a certain maximum, usually Corners, synthesized using a physical barrier (mask) by stepwise addition of each base in the sequence. Thus the arrays represent a full oligonucleotide complement of a region of the target gene. Hybridization of the target mRNA to these arrays provides an exhaustive accessibility profile of this region of the target mRNA. Such data are useful in the design of antisense oligonucleotides (ranging from 7mers to 25mers), where it is important to achieve a compromise between oligonucleotide length and binding affinity, to retain efficacy and target specificity (Sohail et al, Nucleic Acids Res., 2001; 29(10): 2041-2045). Additional methods and concerns for selecting siRNAs are described for example, in WO 05054270, WO05038054A1, WO03070966A2, J Mol. Biol. 2005 May 13; 348(4):883-93, J Mol. Biol. 2005 May 13; 348(4):871-81, and Nucleic Acids Res. 2003 Aug. 1; 31(15):4417-24, each of which is herein incorporated by reference in its entirety. In addition, software (e.g., the MWG online siMAX siRNA design tool) is commercially or publicly available for use in the selection of siRNAs.

2. Antisense

In other embodiments, fusion protein expression is modulated using antisense compounds that specifically hybridize with one or more nucleic acids encoding cancer markers of the present invention. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of cancer markers of the present invention. In the context of the present invention, "modulation" means either an increase (stimulation) or a decrease (inhibition) in the expression of a gene. For example, expression may be inhibited to potentially prevent tumor proliferation.

It is preferred to target specific nucleic acids for antisense. "Targeting" an antisense compound to a particular nucleic acid, in the context of the present invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding a cancer marker of the present invention. The targeting process also includes determination of a site or sites within this gene for the antisense interaction to occur such that the desired effect, e.g., detection or modulation of expression of the protein, will result.

Chimeric antisense compounds of the present invention may be formed as composite structures of two or more oligonucleotides, modified oligonucleotides, oligonucleosides and/or oligonucleotide mimetics as described above.

The present invention also includes pharmaceutical compositions and formulations that include the antisense compounds of the present invention as described below.

B. Gene Therapy

The present invention contemplates the use of any genetic manipulation for use in modulating the expression of cancer markers of the present invention. Examples of genetic manipulation include, but are not limited to, gene knockout (e.g., removing the fusion gene from the chromosome using, for example, recombination), expression of antisense constructs with or without inducible promoters, and the like. Delivery of nucleic acid construct to cells in vitro or in vivo may be conducted using any suitable method. A suitable method is one that introduces the nucleic acid construct into the cell such that the desired event occurs (e.g., expression of an antisense construct). Genetic therapy may also be used to deliver siRNA or other interfering molecules that are expressed in vivo (e.g., upon stimulation by an inducible promoter).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to subject in a variety of ways. For example, in some embodiments of the present invention, vectors are administered into tumors or tissue associated with tumors using direct injection. In other embodiments, administration is via the blood or lymphatic circulation (See e.g., PCT publication 99/02685 herein incorporated by reference in its entirety). Exemplary dose levels of adenoviral vector are preferably $10^8$ to $10^{11}$ vector particles added to the perfusate.

C. Antibody Therapy

In some embodiments, the present invention provides antibodies that target SFT/HPC tumors that express a cancer marker of the present invention (e.g., NAB2-STAT6 gene fusions). Any suitable antibody (e.g., monoclonal, polyclonal, or synthetic) may be utilized in the therapeutic methods disclosed herein. In preferred embodiments, the antibodies used for cancer therapy are humanized antibodies. Methods for humanizing antibodies can be utilized (See e.g., U.S. Pat. Nos. 6,180,370, 5,585,089, 6,054,297, and 5,565,332; each of which is herein incorporated by reference).

In some embodiments, the therapeutic antibodies comprise an antibody generated against a cancer marker of the present invention (e.g., NAB2-STAT6 gene fusions), wherein the antibody is conjugated to a cytotoxic agent. In such embodiments, a tumor specific therapeutic agent is generated that does not target normal cells, thus reducing many of the detrimental side effects of traditional chemotherapy. For certain applications, it is envisioned that the therapeutic agents will be pharmacologic agents that will serve as useful agents for attachment to antibodies, particularly cytotoxic or otherwise anticellular agents having the ability to kill or suppress the growth or cell division of endothelial cells. The present invention contemplates the use of any pharmacologic agent that can be conjugated to an antibody, and delivered in active form. Exemplary anticellular agents include chemotherapeutic agents, radioisotopes, and cytotoxins. The therapeutic antibodies of the present invention may include a variety of cytotoxic moieties, including but not limited to, radioactive isotopes (e.g., iodine-131, iodine-123, technicium-99m, indium-111, rhenium-188, rhenium-186, gallium-67, copper-67, yttrium-90, iodine-125 or astatine-211), hormones such as a steroid, antimetabolites such as cytosines (e.g., arabinoside, fluorouracil, methotrexate or aminopterin; an anthracycline; mitomycin C), vinca alkaloids (e.g., demecolcine; etoposide; mithramycin), and antitumor alkylating agent such as chlorambucil or melphalan. Other embodiments may include agents such as a coagulant, a cytokine, growth factor, bacterial endotoxin or the lipid A moiety of bacterial endotoxin. For example, in some embodiments, therapeutic agents will include plant-, fungus- or bacteria-derived toxin, such as an A chain toxins, a ribosome inactivating protein, α-sarcin, aspergillin, restrictocin, a ribonuclease, diphtheria toxin or pseudomonas exotoxin, to mention just a few examples. In some preferred embodiments, deglycosylated ricin A chain is utilized.

In any event, it is proposed that agents such as these may, if desired, be successfully conjugated to an antibody, in a manner that will allow their targeting, internalization, release or presentation to blood components at the site of the targeted tumor cells as required using conjugation technology (See, e.g., Ghose et al., Methods Enzymol., 93:280 [1983]).

For example, in some embodiments the present invention provides immunotoxins targeted a cancer marker of the present invention (e.g., NAB2-STAT6 gene fusions). Immunotoxins are conjugates of a specific targeting agent typically a tumor-directed antibody or fragment, with a cytotoxic agent, such as a toxin moiety. The targeting agent directs the toxin to, and thereby selectively kills, cells carrying the targeted antigen. In some embodiments, therapeutic antibodies employ crosslinkers that provide high in vivo stability (Thorpe et al., Cancer Res., 48:6396 [1988]).

In other embodiments, particularly those involving treatment of solid tumors, antibodies are designed to have a cytotoxic or otherwise anticellular effect against the tumor vasculature, by suppressing the growth or cell division of the vascular endothelial cells. This attack is intended to lead to a tumor-localized vascular collapse, depriving the tumor cells, particularly those tumor cells distal of the vasculature, of oxygen and nutrients, ultimately leading to cell death and tumor necrosis.

In preferred embodiments, antibody based therapeutics are formulated as pharmaceutical compositions as described below. In preferred embodiments, administration of an antibody composition of the present invention results in a measurable decrease in cancer (e.g., decrease or elimination of tumor).

D. Pharmaceutical Compositions

The present invention further provides pharmaceutical compositions (e.g., comprising pharmaceutical agents that modulate the expression or activity of gene fusions of the present invention). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to techniques such as, for example, bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Certain embodiments of the invention provide pharmaceutical compositions containing (a) one or more antisense compounds and (b) one or more other chemotherapeutic agents that function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Other non-antisense chemotherapeutic agents are also within the scope of this invention. Two or more combined compounds may be used together or sequentially.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 μg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 μg to 100 g per kg of body weight, once or more daily, to once every 20 years.

VII. Transgenic Animals

The present invention contemplates the generation of transgenic animals comprising an exogenous cancer marker gene (e.g., gene fusion) of the present invention or mutants and variants thereof (e.g., truncations or single nucleotide polymorphisms). In preferred embodiments, the transgenic animal displays an altered phenotype (e.g., increased or decreased presence of markers) as compared to wild-type animals. Methods for analyzing the presence or absence of such phenotypes include but are not limited to, those disclosed herein. In some preferred embodiments, the transgenic animals further display an increased or decreased growth of tumors or evidence of cancer.

The transgenic animals of the present invention find use in drug (e.g., cancer therapy) screens. In some embodiments, test compounds (e.g., a drug that is suspected of being useful to treat cancer) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad. Sci. USA 82:6927 [1985]). Transfection is easily and efficiently obtained by culturing the blastomeres on a monolayer of virus-producing cells (Stewart, et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals involve the microinjection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., truncation mutants). Methods for homologous recombination are described in U.S. Pat. No. 5,614,396, incorporated herein by reference.

EXPERIMENTAL

The following examples are provided in order to demonstrate and further illustrate certain preferred embodiments and aspects of the present invention and are not to be construed as limiting the scope thereof.

Example 1

Methods
Clinical Study

Research was performed under Institutional Review Board (IRB)-approved studies. Patient are enrolled and consented through a University of Michigan IRB-approved protocol for integrative tumor sequencing (Roychowdhury et al., Sci Transl Med 2011; 3:111ra21). Medically fit patients 18 years or older with advanced or refractory cancer were eligible for the study. Informed consent detailed the risks of integrative sequencing and included up-front genetic counseling. Biopsies are arranged for safely accessible tumor sites. Needle biopsies were snap frozen in OCT and a longitudinal section was cut. Hematoxylin and eosin (H&E) stained frozen sections were reviewed by study pathologist to identify cores with highest tumor content. Remaining portions of each needle biopsy core were retained for nucleic acid extraction.

Clinicopathologic Features of the Validation Tumor Set

21 SFT with available frozen tissue material from MSKCC files were included for analysis. Sixteen of the SFT were previously analyzed as part of a prior gene expression profiling study and CEL files have been made publicly available 10. There were 11 females and 10 males with a wide age range at diagnosis (27-72 years; mean 54 years). Ten cases were located in the soft tissue (pelvis, 6; flank, 1; thigh, 1; buttock, 1; trunk/peri-scapular, 1), 6 originated in the meninges and 5 were pleural. The samples analyzed by RT-PCR were collected from the primary site in 11 tumors, local recurrence in 5 cases (chest wall/intra-thoracic in 3, orbit/brain in 2), and distant metastases in 5 patients (lung, liver, kidney, pancreas, small bowel). All tumors exhibited diffuse reactivity for CD34. Six tumors were classified as benign, including 5 from soft tissue location and one pleural. The remaining 15 cases were deemed as malignant SFT, based on a mitotic count of >4 MF/10 HPFs, plus/minus areas of necrosis. Among the malignant SFT group of patients, 7 developed distant metastases and 3 local recurrences. Four of the malignant soft tissue SFT cases were also investigated for the presence of an SYT-SSX fusion, diagnostic for synovial sarcoma, which is a close diagnostic mimic included in the differential diagnosis; none of the cases being positive.

DNA/RNA Isolation and cDNA Synthesis

Genomic DNA from frozen needle biopsies and blood was isolated using the Qiagen DNeasy Blood & Tissue Kit, according to the manufacturer's instructions. Briefly, cell or tissue lysates were incubated at 56° C. in the presence of proteinase K and SDS, purified on silica membrane-based mini-columns, and eluted in buffer AE (10 mM Tris-HCl, 0.5 mM EDTA pH 9.0).

Total RNA was extracted from frozen needle biopsies (for RNA-Seq libraries, gene expression analysis and RT-PCR) using the Qiazol reagent with disruption using a 5 mm bead on a Tissuelyser II (Qiagen). RNA was purified using a miRNeasy kit (Qiagen) with DNase I digestion, according to the manufacturer's instructions. RNA integrity was verified on an Agilent 2100 Bioanalyzer (Agilent Technologies) using RNA Nano reagents. cDNA was synthesized from total RNA using Superscript III (Invitrogen) and random primers (Invitrogen). For the MSKCC samples, total RNA was extracted from frozen tumor tissue using the Trizol reagent according to the manufacturer's instructions (Invitrogen). The quality of RNA was tested by RTPCR, using primers for the PGK housekeeping gene.

Next Generation Sequencing Library Preparation

Exome libraries of matched pairs of tumor/normal genomic DNAs were generated using the Illumina TruSeq DNA Sample Prep Kit, following the manufacturer's instructions. 3 μg of each genomic DNA was sheared using a Covaris S2 to a peak target size of 250 bp. Fragmented DNA was concentrated using AMPure XP beads (Beckman Coulter), and DNA ends were repaired using T4 DNA polymerase, Klenow polymerase, and T4 polynucleotide kinase. 3' A-tailing with exo-minus Klenow polymerase was followed by ligation of Illumina paired-end adapters to the genomic DNA fragments. The adapter-ligated libraries were electrophoresed on 3% Nusieve 3:1 (Lonza) agarose gels and fragments between 300 to 350 bp were recovered using QIAEX II gel extraction reagents (Qiagen). Recovered DNA was then amplified using Illumina indexed primers for 9 cycles. The amplified libraries were purified using AMPure XP beads and the DNA concentration was determined using a Nanodrop spectrophotometer. 1 µg of the libraries were hybridized to the Roche EZ Exome v2 capture library at 47° C. for 65 hr following the manufacturer's protocol. The targeted exon fragments were captured on Dynal M-280 streptavidin beads (Invitrogen), washed, eluted, and enriched by amplification with the Illumina indexed primers for 8 additional cycles. After purification of the PCR products with AMPure XP beads, the quality and quantity of the resulting exome libraries were analyzed using an Agilent 2100 Bioanalyzer and DNA 1000 reagents.

RNA-Seq transcriptome libraries were prepared following Illumina's TruSeq RNA protocol, using 2 µg of total RNA. RNA integrity was measured using an Agilent 2100 Bioanalyzer. PolyA+ RNA was isolated using Sera-Mag oligo(dT) beads (Thermo Scientific) and fragmented with the Ambion Fragmentation Reagents kit (Ambion, Austin, Tex.). cDNA synthesis, end-repair, A-base addition, and ligation of the Illumina indexed adapters were performed according to Illumina's protocol. Libraries were then size-selected for 250-300 bp cDNA fragments on a 3% Nusieve 3:1 (Lonza) agarose gel, recovered using QIAEX II gel extraction reagents (Qiagen), and PCR amplified using Phusion DNA polymerase (New England Biolabs) for 14 PCR cycles. The amplified libraries were purified using AMPure XP beads. Library quality was determined by assaying each library on an Agilent 2100 Bioanalyzer for product size and concentration. Paired-end libraries were sequenced with the Illumina HiSeq 2000, (2×100 nucleotide read length). Reads that passed the chastity filter of Illumina BaseCall software were used for subsequent analysis.

The publicly available software FastQC was used to assess sequence quality. For each lane, per-base quality scores were examined across the length of the reads. Lanes were deemed passing if the per-base quality score boxplot indicated that >75% of the reads had >Q20 for bases 1-80. All lanes passed this threshold. In addition to the raw sequence quality, alignment quality was assessed using the Picard package. This allows monitoring of duplication rates and chimeric reads that may result from ligation artifacts; crucial statistics for interpreting the results of copy number and structural variant analysis.

Mutation Analyses

The resulting somatic mutations were annotated using RefSeq transcripts. HUGO gene names were used. For NAB2 mRNA and protein, positions and annotations are derived from RefSeq accessions NM_005967 and NP_005958 respectively. For STAT6 mRNA and protein, positions and annotations are derived from RefSeq accessions NM_001178078 and NP_001171549 respectively. The impact of coding nonsynonymous amino acid substitutions on the structure and function of a protein was assessed using PolyPhen-267. It was also assessed whether the somatic variant was previously reported in dbSNP135 or COSMIC v5668.

Tumor content for each tumor exome library was estimated from the sequence data by fitting a binomial mixture model with two components to the set of most likely SNV candidates on 2-copy genomic regions. The set of candidates used for estimation consisted of coding variants that (1) exhibited at least 3 variant fragments in the tumor sample, (2) exhibited zero variant fragments in the matched benign sample with at least 16 fragments of coverage, (3) were not present in dbSNP, (4) were within a targeted exon or within 100 base pairs of a targeted exon, (5) were not in homopolymer runs of four or more bases, and (6) exhibited no evidence of amplification or deletion. In order to filter out regions of possible amplification or deletion, exon coverage ratios were used to infer copy number changes, as described below. Resulting SNV candidates were not used for estimation of tumor content if the segmented logratio exceeded 0.2 in absolute value. Candidates on the Y chromosome were also eliminated because they were unlikely to exist in 2-copy genomic regions. Using this set of candidates, a binomial mixture model with two components was fit using the R package flexmix, version 2.3-8. The component consisted of SNV candidates with very low variant fractions, resulting from recurrent sequencing errors and other artifacts. The other component, consisting of the likely set of true SNVs, was informative of tumor content in the tumor sample. Specifically, under the assumption that most or all of the observed SNV candidates in this component are heterozygous SNVs, the estimated binomial proportion of this component represents one-half of the proportion of tumor cells in the sample. Thus, the estimated binomial proportion as obtained from the mixture model was doubled to obtain an estimate of tumor content.

Copy number aberrations were quantified and reported for each gene as the segmented normalized log 2-transformed exon coverage ratios between each tumor sample and matched normal sample (Lonigro et al., Neoplasia 2011; 13:1019-25). To account for observed associations between coverage ratios and variation in GC content across the genome, lowess normalization was used to correct per-exon coverage ratios prior to segmentation analysis. Specifically, mean GC percentage was computed for each targeted region, and a lowess curve was fit to the scatterplot of log 2-coverage ratios vs. mean GC content across the targeted exome using the lowess function in R (version 2.13.1) with smoothing parameter f=0.05.

Somatic point mutations were identified in the tumor exome sequence data using the matched normal exome data to eliminate germline polymorphisms. Parameters and computational methods were as previously described (Grasso et al., Nature 2012; advance online publication).

To identify gene fusions, paired-end transcriptome reads passing filter were mapped to the human reference genome (hg19) and UCSC genes, allowing up to two mismatches, with Illumina ELAND software (Efficient Alignment of Nucleotide Databases) and Bowtie (Langmead B. Aligning short sequencing reads with Bowtie. Curr Protoc Bioinformatics 2010; Chapter 11: Unit 11 7). Sequence alignments were subsequently processed to nominate gene fusions using the methods described earlier (Iyer et al., Bioinformatics 2011; 27:2903-4; Robinson et al., Nat Med 2011; 17:1646-51). In brief, paired end reads were processed to identify any that either contained or spanned a fusion junction. Encompassing paired reads refer to those in which each read aligns to an independent transcript, thereby encompassing the fusion junction. Spanning mate pairs refer to those in which one sequence read aligns to a gene and its paired end spans the fusion junction. Both categories undergo a series of filtering steps to remove false positives before being merged together to generate the final chimera nominations. Reads supporting each fusion were realigned using BLAT (UCSC Genome Browser) to reconfirm the fusion breakpoint.

For RNA-Seq gene expression analysis, transcriptome data was processed as previously described (Roychowdhury et al., Sci Transl Med 2011; 3:111ra21). Genes were nominated as exhibiting potential "outlier" expression relative to a cohort of N=282 previously sequenced tissues using the following conditions: (1) the gene was required to have an expression value of at least 20 RPKM in the sample of interest; (2) the gene was required to be at or above the 90th percentile relative to all previously sequenced tissues, of any type; (3) the gene was required to have a fold change of at least 2 relative to the maximum RPKM over all previously sequenced benign tissues; and (4) the 25th percentile of the gene expression measurements over the previously sequenced tissues was required to be less than 50 RPKM. Collectively, these parameters target genes with (1) high absolute expression, (2) high expression relative to previously sequenced tissues, (3) high expression relative to all benign tissues, and (4) expression that is not uniformly high across all tissues.

Partially redundant sequencing of areas of the genome affords the ability for cross validation of findings. Cross-validated exome-based point mutation calls were validated by manually examining the genomic and transcriptomic reads covering the mutation using the UCSC Genome Browser. Likewise, gene fusion calls from the transcriptome data can be further supported by structural variant detection in the genomic sequence data, as well as copy number information derived from the genome and exome sequencing.

Quantitative RT-PCR and Long-Range PCR

For validation of fusion transcripts, RT-PCR and quantitative RT-PCR assays were performed. One microgram of total RNA from 21 SFT was used for RT-PCR using SuperScript III First-Strand System (Invitrogen), according to the manufacturer's instructions. The primers used were: NAB2ex5 Forward: 5' CCTGTCTGGGGAGAGTCTG-GATG 3' (SEQ ID NO:1) and STAT6ex20 Reverse: 5' GGGGGGATGGAGTGAGAGTGTG 3' (SEQ ID NO:2). The PCR products were analyzed by agarose gel electrophoresis. The amplified PCR products were purified then sequenced using the Sanger method. Quantitative RT-PCR assay was performed using SYBR Green Master Mix (Applied Biosystems) and was carried out with the StepOne Real-Time PCR System (Applied Biosystems). Relative mRNA levels of the fusion transcripts were normalized to the expression of the housekeeping gene GAPDH. Oligonucleotide primers were obtained from Integrated DNA Technologies (IDT) and the sequences given in the Supplement. To detect the genomic fusion junction between the NAB2 and STAT6 genes in the MO_1005 tumor DNA, primers were designed flanking the predicted genomic junction and PCR reactions were carried out to amplify the fusion fragments. PCR products were purified from agarose gels using the QIAEX II system (QIAGEN) and sequenced by Sanger sequencing methods at the University of Michigan Sequencing Core.

Immunoblot and Immunofluorescence Assays

Total protein lysates were extracted from frozen tissue from 8 SFT tumors. In three of the cases, adequate quality frozen normal tissues were available for protein extraction for comparison. Electrophoresis and immunoblotting were performed using 30 μg of total protein extract, following the standard protocol. Total STAT6 and β-actin were detected by rabbit polyclonal anti-STAT6 (Cell Signaling Technology, Cat #9362S; 1:1500 dilution) and rabbit monoclonal anti-β-actin (Cell Signaling Technology, Cat #4970; 1:1500 dilution). The secondary antibodies used were goat anti-rabbit (Santa Cruz Biotechnology, Cat #SC-2034) with 1:20000 dilution. The same total STAT6 antibody was used for immunofluorescence (IF) for detecting the cellular localization of the protein.

NAB2-STAT6 Cloning, Expression, and Stable Cell Line Analyses

The NAB2-STAT6 fusion allele was PCR amplified from cDNA of the index case (MO_1005) using the primers listed in the supplement and the Expand High Fidelity protocol (Roche). The PCR product was digested with restriction endonuclease Cpo I (Fermentas) and ligated into the pCDH510B lentiviral vector (System Biosciences), which had been modified to contain an N-terminal FLAG epitope tag. Lentiviruses were produced by cotransfecting the NAB2-STAT6 construct or vector with the ViraPower packaging mix (Invitrogen) into 293T cells using FuGene HD transfection reagent (Roche). Twelve hours post-transfection, the media was changed. Thirty-six hours post-transfection the viral supernatants were harvested, centrifuged at 5,000×g for 30 minutes and then filtered through a 0.45 micron Steriflip filter unit (Millipore). Benign RWPE-1 cells at 30% confluence were infected at an MOI of 20 with the addition of polybrene at 8 mg/ml. Forty-eight hours post-infection, the cells were split and placed into selective media containing 10 μg/ml puromycin. Two stable pools of resistant cells were obtained and analyzed for expression of the FLAG-NAB2-STAT6 fusion allele by western blot analysis with monoclonal anti-FLAG M2 antibody (Sigma-Aldrich). Expression was confirmed by qPCR for the NAB2-STAT6 fusion allele.

For the cell proliferation assay, vector control, NAB2-STAT6 high, and NAB2-STAT6 low level over-expressing cells were plated in quadruplicate at 8,000 cells per well in 24 well plates. The plates were incubated at 37° C. and 5% $CO_2$ atmosphere using the IncuCyte live-cell imaging system (Essen Biosciences). Cell proliferation was assessed by kinetic imaging confluence measurements at 3-hour time intervals.

Results

Clinical Sequencing of the Index Patient (MO_1005)

The index patient was a 44 year-old woman who had surgery and post-operative radiation for an anaplastic meningioma in 2002. In 2009, MRI showed a new brain mass, but also showed a paraspinal mass. Laminectomy was performed and review of the tissue showed metastatic SFT, strongly immunoreactive for CD34. In 2011, the patient was enrolled in the MI-ONCOSEQ integrated cancer sequencing program (FIG. 1A) after progression of sarcoma on chemotherapy. The MI-ONCOSEQ study focuses on a patient population considering clinical trials where integrative sequencing could have a potential impact and features a clinically relevant timeframe of four weeks from biopsy to disclosure of results (Roychowdhury et al., supra). Normal blood/buccal swab specimens and CT-guided core needle biopsies were obtained from a metastatic site in the liver (FIG. 1B). Representative images of the original diagnostic material are shown in FIG. 1C. The specimen displayed typical morphologic features of SFT with HPC-like vessels, collagenous stroma, patternless architecture of spindled (FIG. 1C, left panel) to ovoid tumor cells (FIG. 1C, middle panel). More than 4 mitoses per 10 high power field were identified. Immunostaining for CD34 was positive in the tumor cells and in the endothelial cells, highlighting branching vessels (FIG. 1C, right panel). An image of a representative frozen section used for molecular analyses was recorded. The biopsy cores used for molecular analysis had over 70% tumor cell content based on morphologic analysis.

High quality DNA and RNA was isolated from the core needle biopsies and subjected to next generation sequencing. Cancer arises from diverse genetic alterations including nucleic acid substitutions, gene fusions/rearrangements, amplifications/deletions, and other aberrations that perturb gene expression levels. Therefore, clinical application of a sequencing strategy should identify clinically significant alterations. Thus, an integrative sequencing strategy that incorporates whole exome sequencing of the tumor and normal tissue, low pass genome sequencing and transcriptome sequencing of the tumor was employed (Roychowdhury et al., supra). Classes of mutations detectable using this approach include germline alterations, point mutations, indels, amplifications, deletions, gene fusions/translocations, and outlier gene expression.

Figure 5:
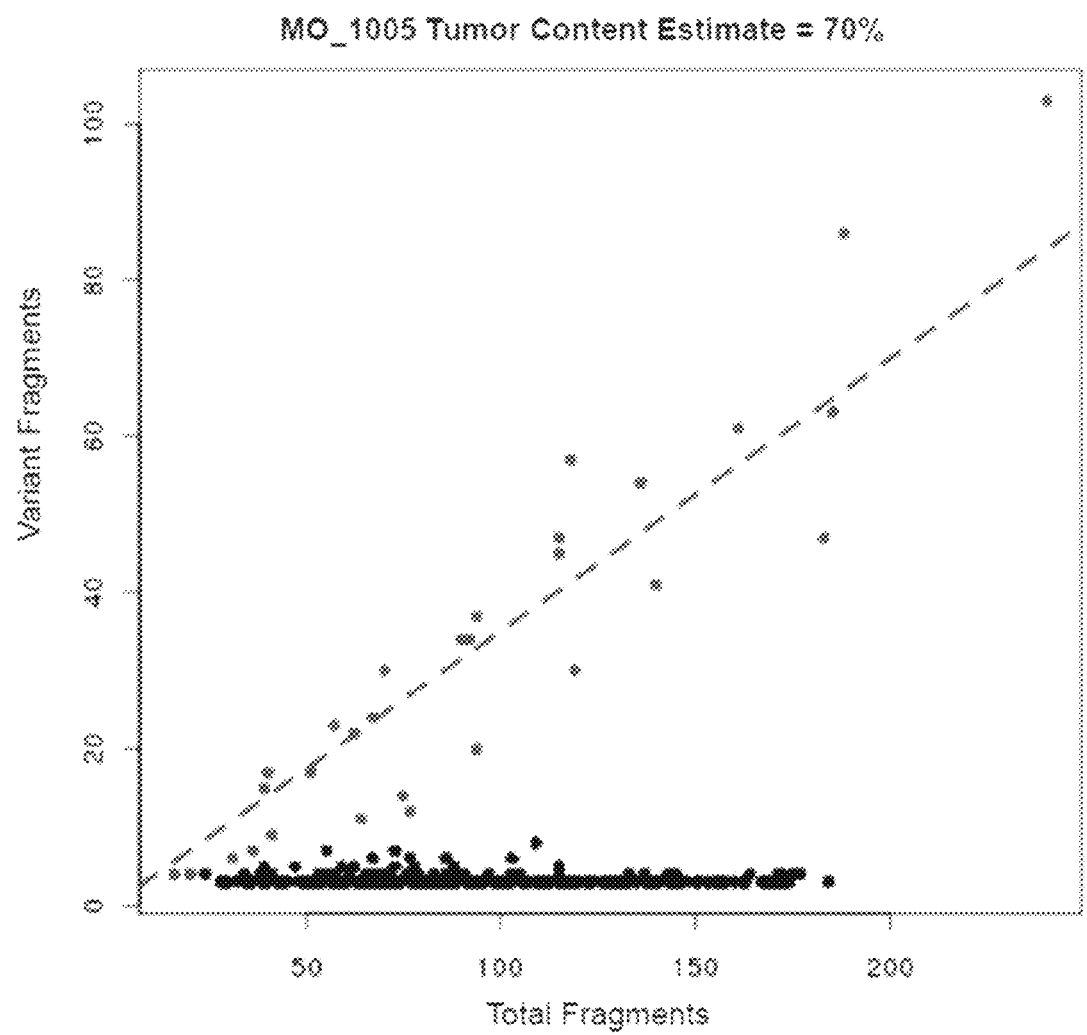
FIG. 5 shows tumor content of index case MO_1005.
Figure 6:
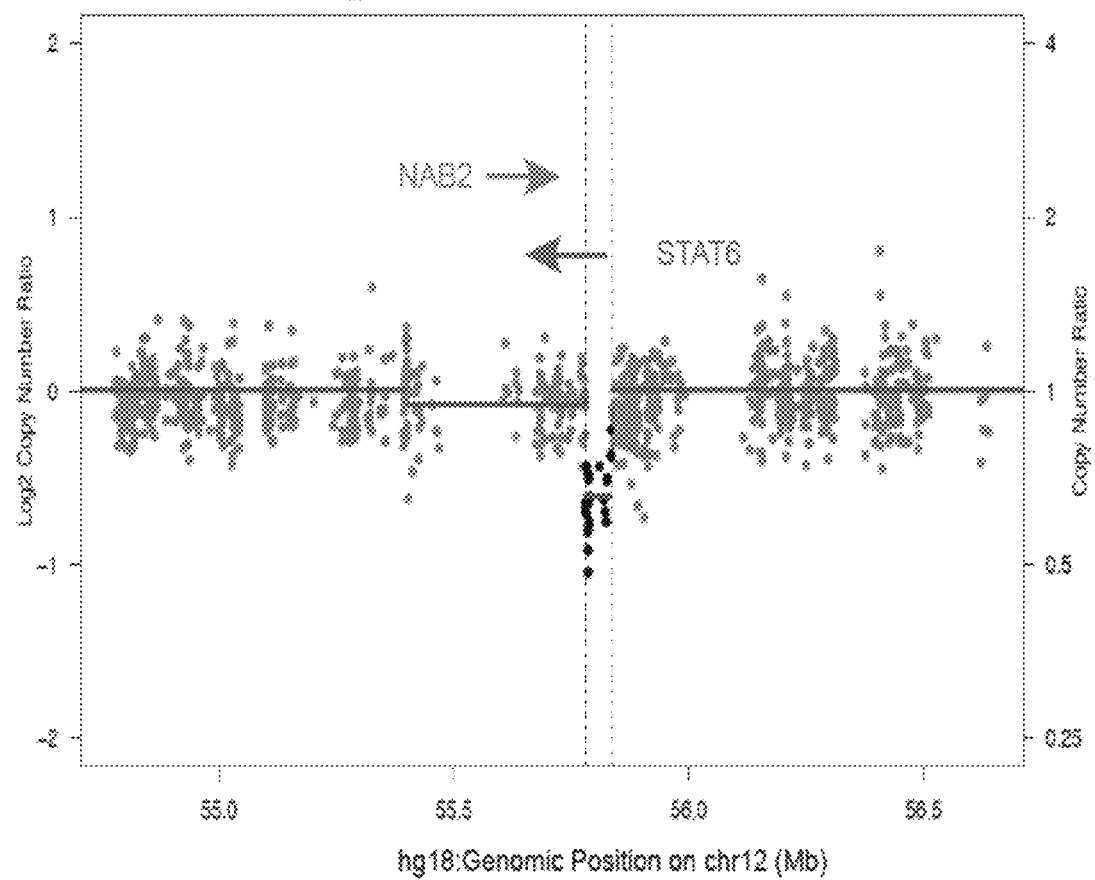
FIG. 6 shows copy number changes around STAT6 gene in MO_1005.

Whole exome sequencing of the tumor and matched normal from MO_1005 revealed 14 nonsynonymous point mutations (FIG. 1D and Table 3). No significant germline aberrations or somatic point mutations were identified in genes frequently mutated in cancer such as TP53, KRAS, BRAF, or PIK3CA among others. The exome data coupled with SNV candidate variant modeling were used to estimate tumor content of the biopsy specimen at 70% corroborating the histologic assessment (Supplemental FIG. 5). A global landscape of copy number alterations was generated based on exome sequencing (FIG. 1E) and there were only a few regions of significant copy number gain or loss (Tables 4 and 5). Of note there was a focal 56 kb one copy deletion observed in the STAT6 locus. Paired-end transcriptome sequencing of RNA revealed an intrachromosomal fusion between NAB2 and STAT6 (FIG. 1F). The NAB2-STAT6 fusion was represented by 1,104 paired-end reads and indicated a fusion of exon 6 of NAB2 to exon 18 of STAT6. Wild type NAB2 and STAT6 are adjacent genes on chromosome 12q13, transcribed in opposite directions. NAB2-STAT6 was the single fusion identified in the index case, consistent with the overall copy number profile and unlike the greater number of gene fusions observed in cancers with more extensively rearranged genomes (Robinson et al., Nat Med 2011; 17:1646-51; Stephens et al., Nature 2009; 462:1005-10).

Validation of the NAB2-STAT6 Gene Fusion

Figure 2:
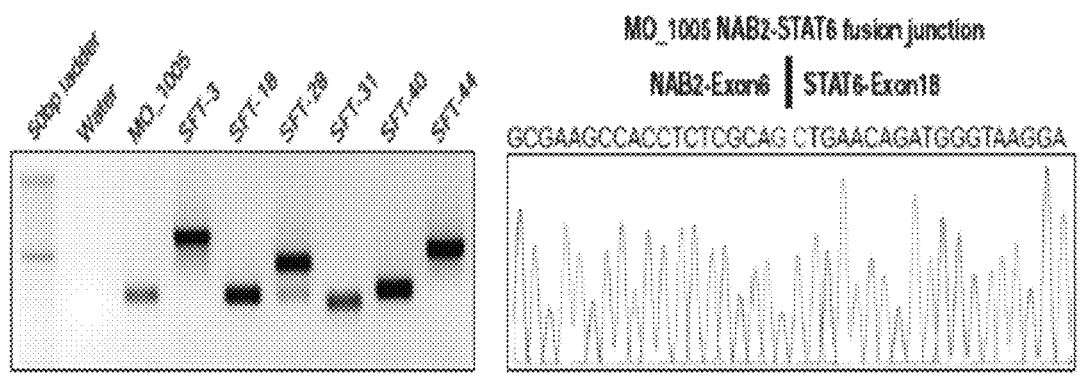
FIG. 2 shows validation and recurrence of NAB2-STAT6 gene fusions in SFT. A, RT-PCR (left panel) and capillary sequencing trace (right panel; SEQ ID NO:25) of the index case and additional SFT cases using primers for NAB2-exon 6 and STAT6-exon 19. B, Genomic long-range PCR of the index case confirming the existence of the NAB2-STAT6 gene fusion at the DNA level. Gel electrophoresis of the amplified product (left panel) and schematic of exon-intron structure of the index NAB2-STAT6 gene fusion (right panel) are shown. C, Schematic representations of additional NAB2-STAT6 gene fusions identified by transcriptome sequencing of 6 SFT samples.
Figure 2:
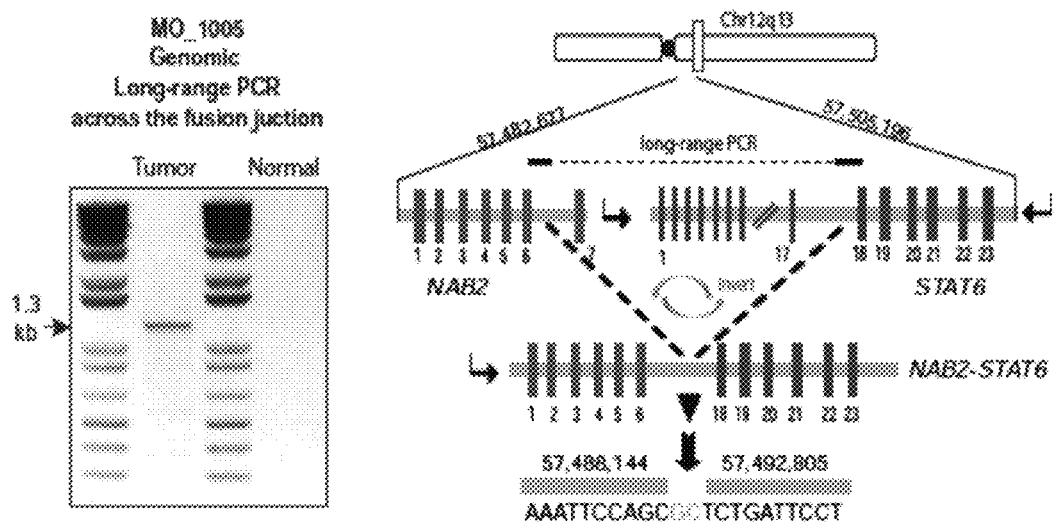
Figure 2:
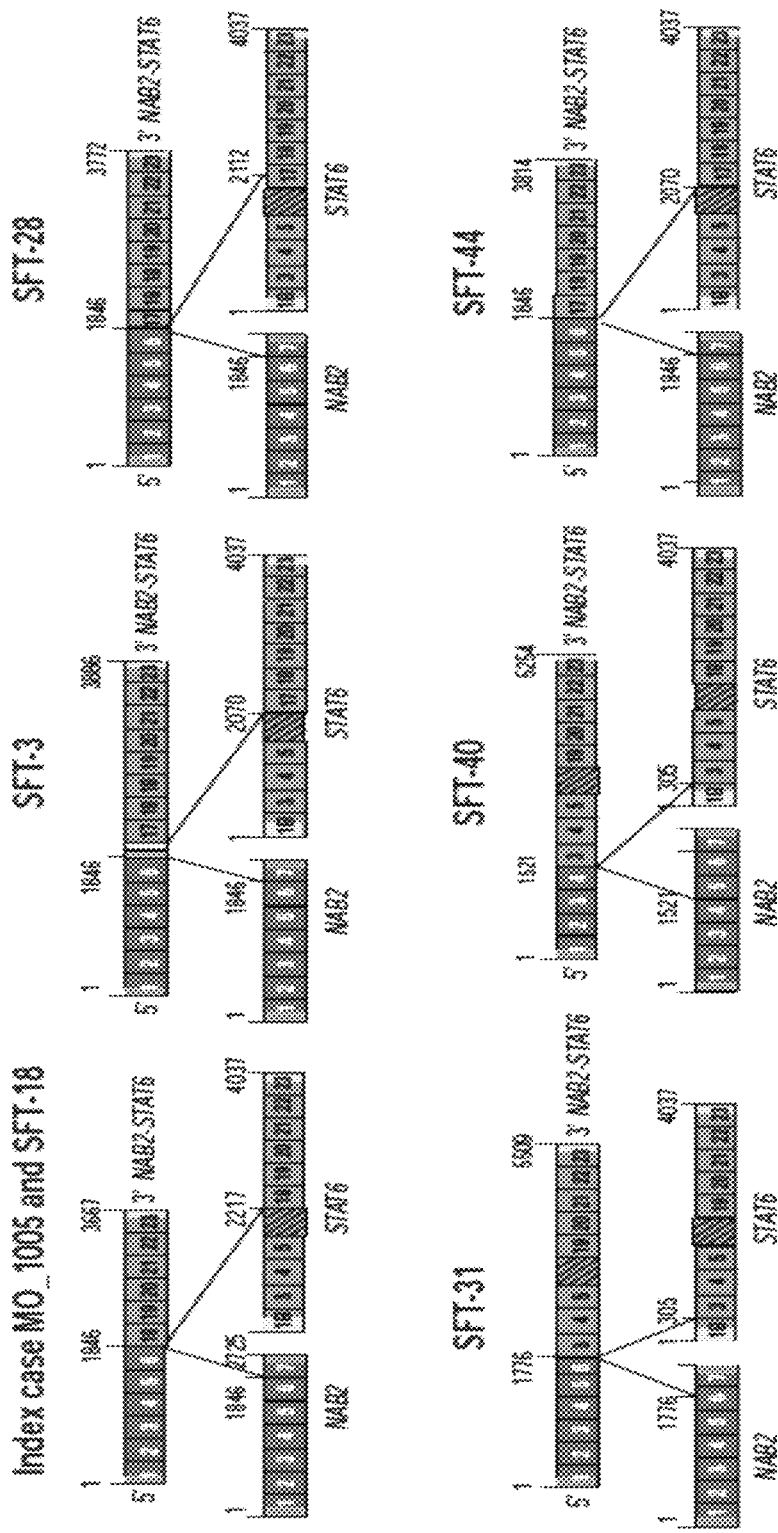

Using primers located within exon 6 of NAB2 and exon 19 of STAT6, the NAB2-STAT6 fusion was confirmed in the index case by RT-PCR (FIG. 2A, left panel) followed by Sanger sequencing of the amplified product (FIG. 2A, right panel). To confirm that that the fusion exists at the DNA level and is not a product of a complex trans-splicing event long range PCR of genomic DNA was performed. A 1.3 kb product was obtained specifically in the index tumor and not the matched normal tissue (FIG. 2B, left panel). This allowed mapping of the genomic breakpoint of the NAB2-STAT6 fusion (FIG. 2B, right panel) in the index case and confirmed that a genomic inversion occurs at the Chr12q13 locus fusing NAB2 and STAT6 in a common direction of transcription.

Figure 7:
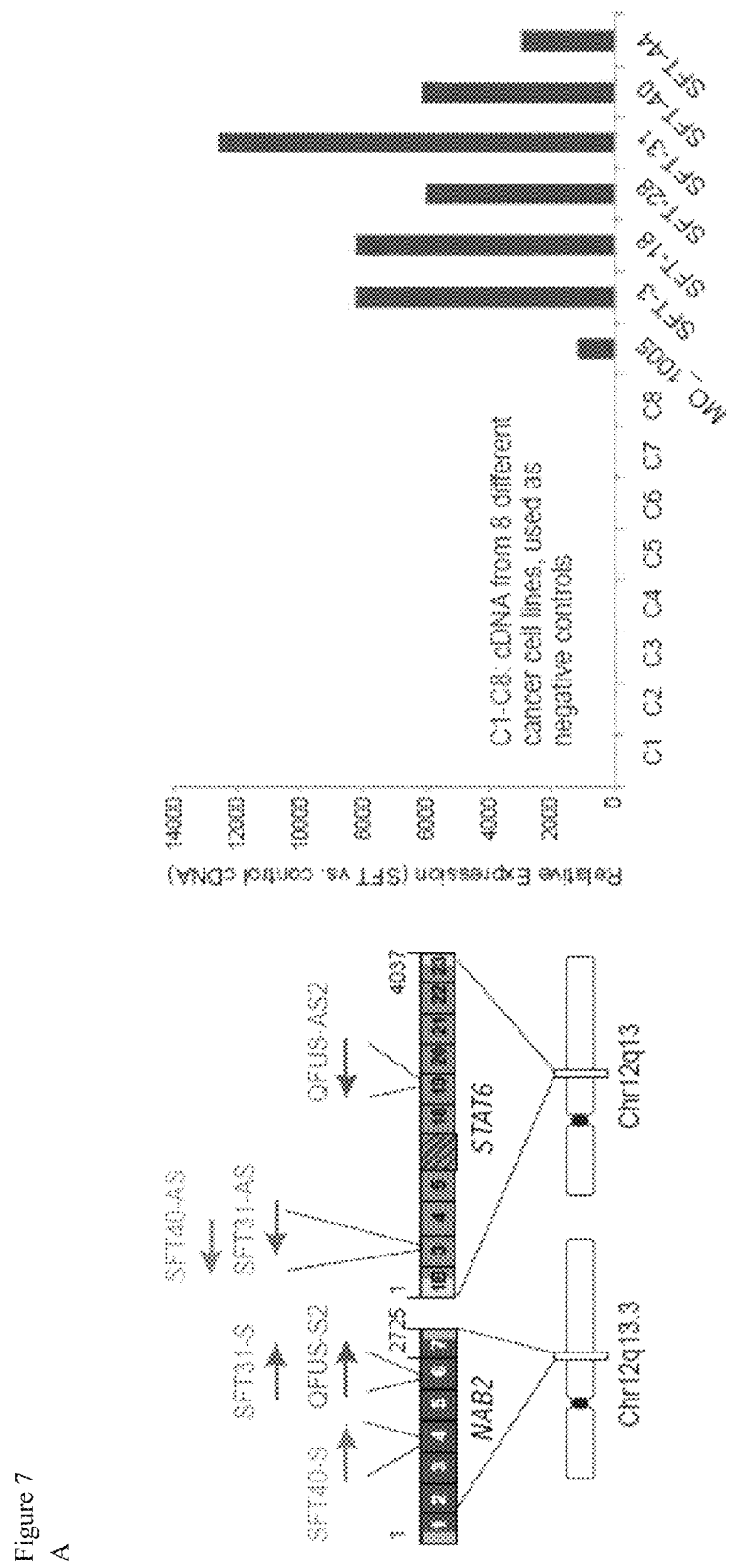
FIG. 7 shows validation of NAB2-STAT6 fusions in SFT samples by quantitative RT-PCR. A. The locations of PCR primer pairs are shown on the left. B. Sequences across NAB2-STAT6 fusion junctions in SFT samples (SEQ ID NOs: 27-30).
Figure 7:
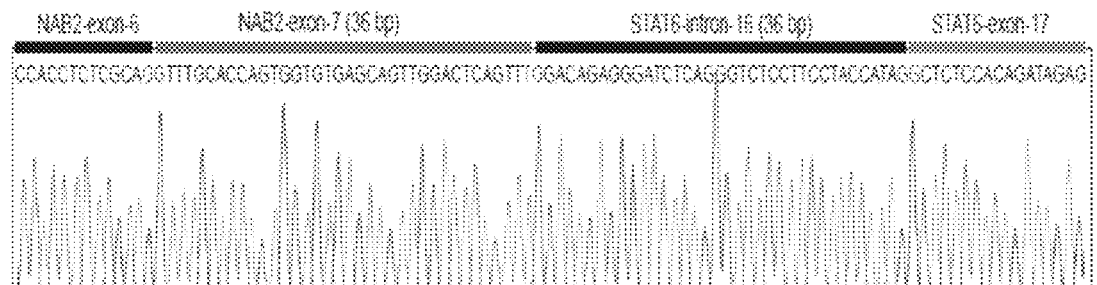
Figure 7:
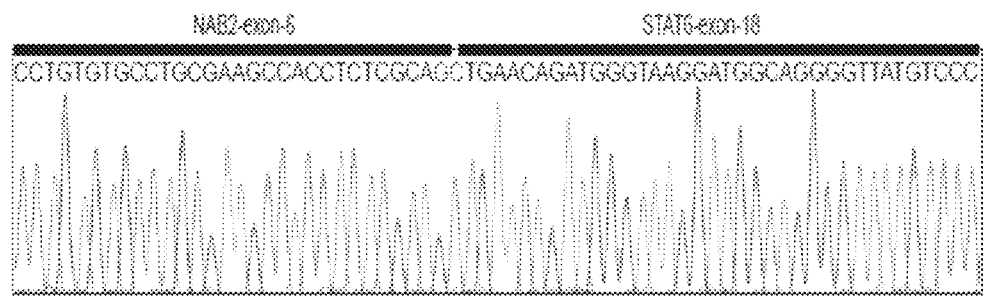
Figure 7:
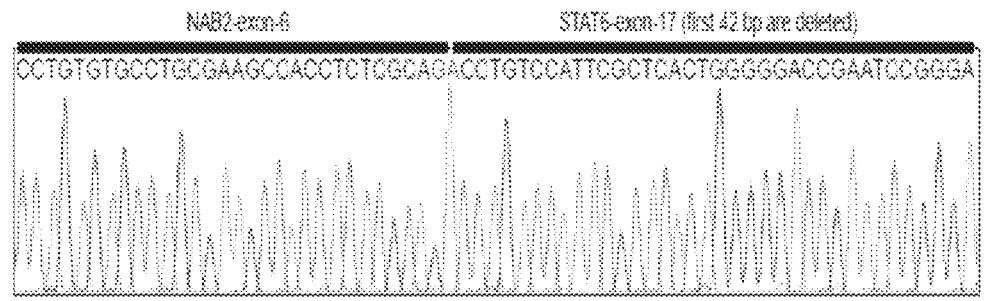
Figure 7:
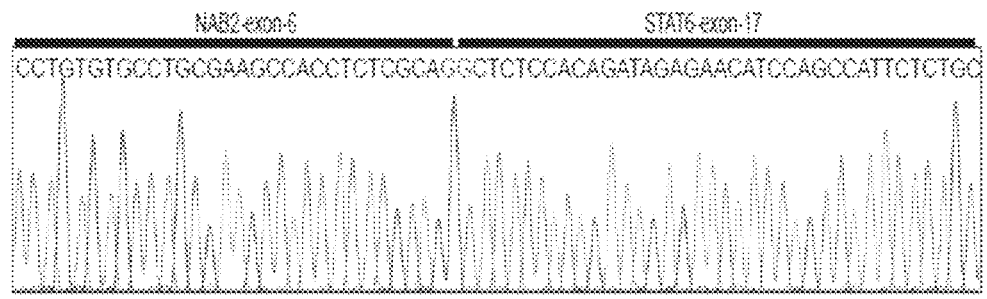
Figure 8:
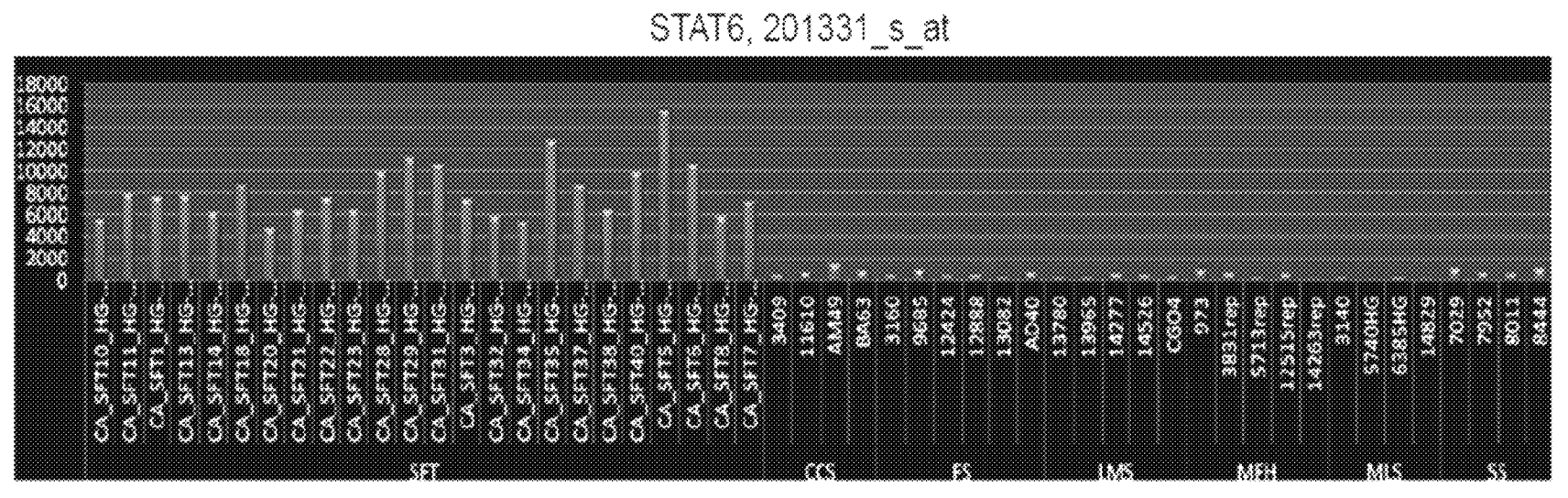

To determine whether the NAB2-STAT6 fusion is recurrent 6 cases of SFT from MSKCC were analyzed by transcriptome sequencing. While there was variation in the precise exon structure of the fusions detected, 6 out of 6 cases displayed high levels of a NAB2-STAT6 gene fusion (FIG. 2C). The number of paired-end reads varied from 1,104 to 4,483 per case and Exon 4 or 6 of NAB2 was found to be fused to Exon 3, 17 or 18 of STAT6. RT-PCR combined with sequencing was carried out on 21 total cases of SFT from MSKCC and all cases were positive for a NAB2-STAT6 fusion (FIG. 2A and Table 1). Selected cases were further confirmed by QRT-PCR analysis (Table 1 and FIG. 7A). Thus, regardless of anatomic site of origin or malignant versus benign status, all cases of SFT harbored a NAB2-STAT6 gene fusion. As all of the NAB2-STAT6 gene fusions identified harbor 3' exons of STAT6, an Affymetrix gene expression dataset of soft tissue sarcomas that included a 3' probe to STAT6 (U133A, probeset 201331_s_at) was used to assess expression. Importantly, 100% of the SFTs (24 out of 24) expressed the 3' exons of STAT6 as compared to other sarcomas (FIG. 8).

Analysis of the Predicted NAB2-STAT6 Fusion Proteins

Figure 3:
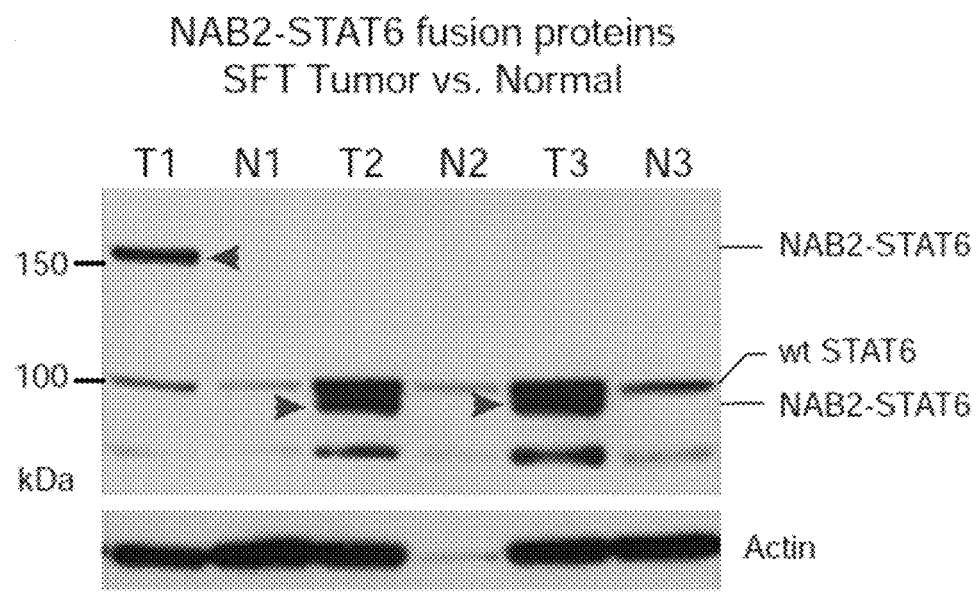
FIG. 3 shows characterization and functional analysis of the NAB2-STAT6 gene fusion protein. A, Schematic representations of the predicted NAB2-STAT6 fusion protein products identified in this study. EBD, EGR1 binding domain; NCD2, NAB2 conserved domain; RD, transcriptional repressor domain; CCD1, coiled coil domain; DBD, DNA binding domain; TAD, transcriptional activator domain. B, Immunoblot analysis of three SFT cases and matched normal tissue employing an antibody against a C-terminal epitope of STAT6, which is found in all the NAB2-STAT6 gene fusions thus far identified. C, Immunofluorescence using the same antibody as in B, showing the nuclear localization of the NAB2-STAT6 protein in a representative SFT case. D, Stable RWPE-1 cell line pools expressing low and high levels of a FLAG-epitope tagged NAB2-STAT6 gene fusion (MO_1005 fusion structure) were generated. E, Cell proliferation assays as determined by live-cell imaging were employed on cell lines described in D. F, QRT-PCR for EGR1 target genes IGF2, H19, and RRAD was carried out on cell lines from D.
Figure 3:
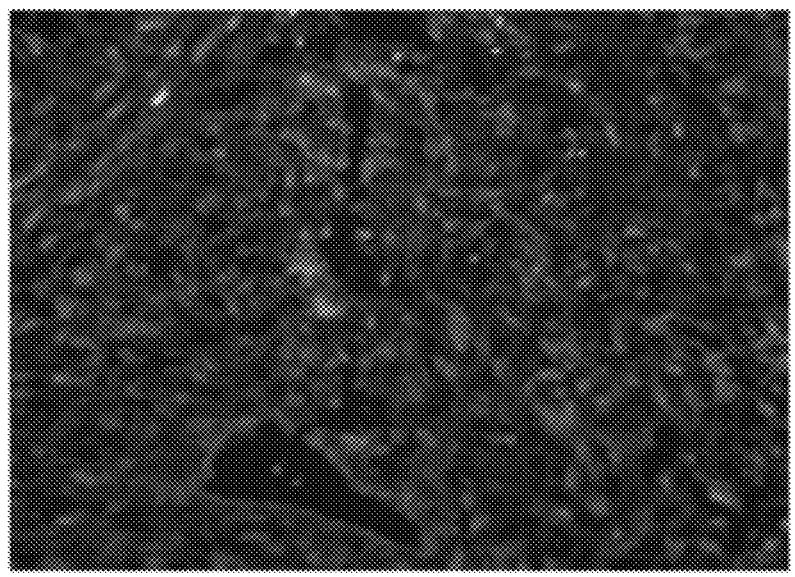
Figure 3:
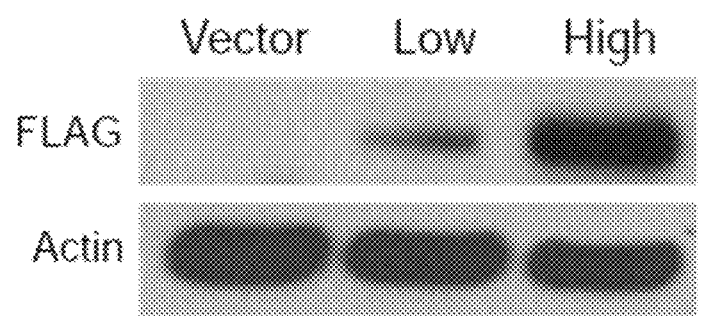
Figure 3:
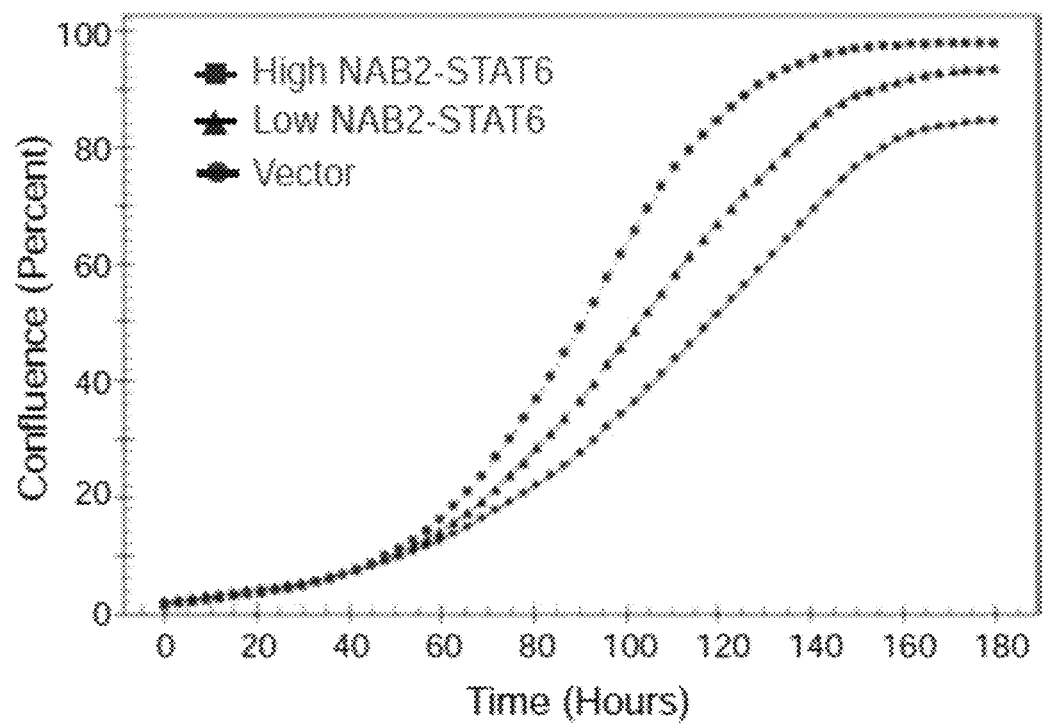
Figure 3:
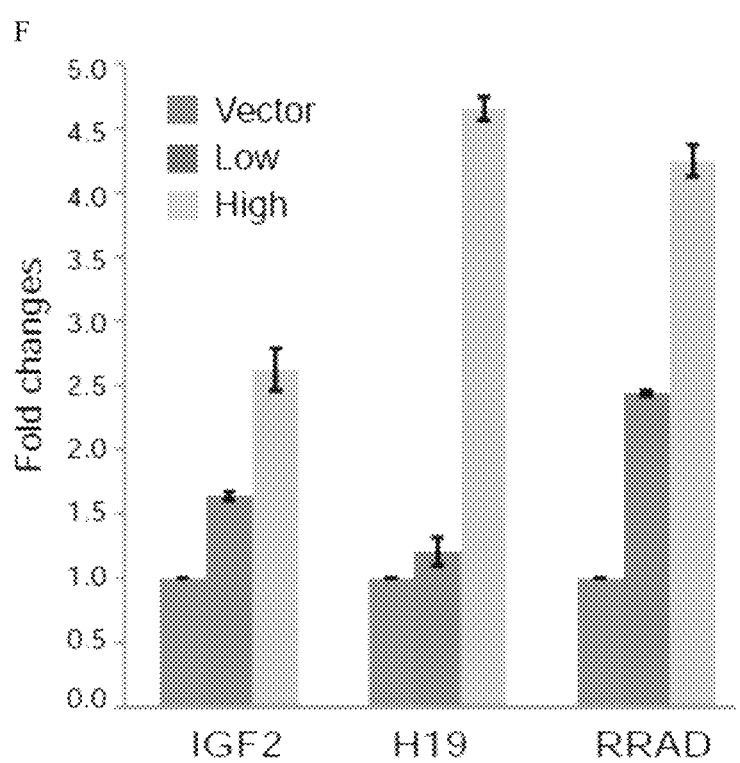

NAB2 is comprised of an N-terminal EGR1 binding domain (EBD), a NAB conserved region 2 (NCD2) and a C-terminal transcriptional repressor domain (RD). STAT6 is comprised of a DNA-binding domain (DBD), SH2 domain, and a C-terminal transcriptional activation domain (TAD). FIG. 3A displays the domain structures of the wild type NAB2 and STAT6 proteins as well as the six predicted NAB2-STAT6 fusion proteins identified by transcriptome sequencing in this study. A common feature of all of the NAB2-STAT6 fusion proteins is variable truncation in the RD motif of NAB2, which is then fused minimally to the TAD motif of STAT6.

Expression of the predicted NAB2-STAT6 fusion protein products were confirmed by immunoblot analysis of 3 cases of SFT (FIG. 3B). Employing an antibody to the C-terminus of STAT6, which is present in all the fusions, indicated expression of the respective fusion products only in the tumor samples and not in the matched normals (in which only wild-type STAT6 was expressed). Similarly, immunofluorescence using this STAT6 antibody indicated strong nuclear localization of NAB2-STAT6 protein (FIG. 3C).

Functional Characterization of NAB2-STAT6 Gene Fusion

The NAB2-STAT6 fusion allele was amplified from the index SFT/HPC case (MO_1005) and cloned into a lentiviral vector with a FLAG-epitope tag. Benign RWPE-1 cells were infected with vector or NAB2-STAT6 virus and pooled stable cell lines generated. High and low NAB2-STAT6 expressing stable cell lines were characterized (FIG. 3D). The high NAB2-STAT6 cell line displayed a markedly increased level of proliferation compared to the vector control, while the low NAB2-STAT6 cell line displayed an intermediate level of proliferation as measured by live-cell imaging (FIG. 3E). As NAB2 is a well-characterized repressor of EGR1 transcriptional activity (Srinivasan et al., J Biol Chem 2006; 281:15129-37; Svaren et al., Mol Cell Biol 1996; 16:3545-53). The expression of established EGR1 target genes was measured in the NAB2-STAT6 stable cell lines (FIG. 3F) (Svaren et al., J Biol Chem 2000; 275:38524-31). In contrast to the known activity of NAB2, the NAB2-STAT6 fusion induced expression of EGR1 target genes.

TABLE 1

| Case | Age | Gender | Location | Malignant | CD34 | RNA-Seq | QRT-PCR | RT-PCR + Seq |
|---|---|---|---|---|---|---|---|---|
| MO-1005* | 44 | F | Meningeal origin, liver met | + | + | + | + | + |
| SFT-1 | 50 | F | ST, pelvis | − | + | | | + |

TABLE 1-continued

| Case | Age | Gender | Location | Malignant | CD34 | RNA-Seq | QRT-PCR | RT-PCR + Seq |
|---|---|---|---|---|---|---|---|---|
| SFT-3 | 58 | F | ST, buttock | + | + | + | + | + |
| SFT-5 | 67 | M | Pleura, recurrence | + | + | | | + |
| SFT-6 | 70 | F | ST, pelvis | + | + | | | + |
| SFT-7 | 57 | M | Pleura | − | + | | | + |
| SFT-10 | 78 | F | ST, thigh | + | + | | | + |
| SFT-13 | 54 | F | ST, periscapular | − | + | | | + |
| SFT-14 | 72 | M | Pleura | + | + | | | + |
| SFT-18 | 67 | F | ST, pelvis | − | + | + | + | + |
| SFT-22 | 40 | M | Meningeal origin, lung met | + | + | | | + |
| SFT-23 | 49 | F | Meningeal origin, orbital recurrence | + | + | | | + |
| SFT-28 | 33 | F | Meningeal origin, kidney met | + | + | + | + | + |
| SFT-31 | 67 | F | Meningeal origin, brain recurrence | + | + | + | + | + |
| SFT-35 | 63 | F | Pleura, recurrence | + | + | | | + |
| SFT-38 | 31 | M | ST, pelvis | + | + | | | + |
| SFT-40 | 67 | M | Pleura, recurrence | + | + | + | + | + |
| SFT-44 | 29 | M | Meningeal origin, pancreatic met | + | + | + | + | + |
| SFT-46 | 59 | F | ST, retroperitoneum | + | + | | | + |
| SFT-47 | 32 | M | Meningeal origin, small bowel met | + | + | | | + |
| SFT-49 | 71 | M | ST, pelvis | − | + | | | + |
| SFT-50 | 27 | M | ST, pelvis | − | + | | | + |

TABLE 2

| Sample | Library Type | Lane | Yield (Mbases) | % Reads Pass Filter | # Reads PF | % of ≥ Q30 Bases (PF) | Mean Quality Score (PF) | Error Rate PhiX |
|---|---|---|---|---|---|---|---|---|
| MO_1005 Normal | Genomic | C01RPABXX_3 | 18,776 | 93.7 | 192,658,962 | 88.6 | 35.1 | 0.36 |
| MO_1005 Tumor | Genomic | C01RPABXX_4 | 14,382 | 95.4 | 145,006,666 | 90.8 | 35.8 | 0.32 |
| MO_1005 Normal | Exome (Roche EZ Exome v2) | C01RPABXX_8 | 15,807 | 95.7 | 158,838,386 | 90.4 | 35.5 | 0.33 |
| MO_1005 Tumor | Exome (Roche EZ Exome v2) | C0282ABXX_1 | 18,609 | 94.6 | 189,130,200 | 89.9 | 35.4 | 0.36 |
| MO_1005 Tumor | Transcriptome | C0282ABXX_4 | 17,032 | 94.5 | 173,308,880 | 88.1 | 34.7 | 0.30 |
| STF-3 Tumor | Transcriptome | C0L92ACXX_5 | 19,534 | 91.9 | 210,562,550 | 90.5 | 35.3 | 0.35 |
| STF-18 Tumor | Transcriptome | C0L92ACXX_6 | 19,385 | 93.0 | 206,405,522 | 90.8 | 35.4 | 0.36 |
| STF-28 Tumor | Transcriptome | C0L92ACXX_7 | 17,909 | 93.2 | 190,346,700 | 91.4 | 35.5 | 0.28 |
| STF-31 Tumor | Transcriptome | C0L92ACXX_8 | 20,214 | 92.6 | 216,140,296 | 90.6 | 35.3 | 0.29 |
| STF-40 Tumor | Transcriptome | C0LAMACXX_1 | 17,597 | 94.3 | 184,732,802 | 91.5 | 35.6 | 0.34 |
| STF-44 Tumor | Transcriptome | C0LARACXX_4 | 10,465 | 93.0 | 111,466,992 | 88.6 | 34.7 | 0.58 |

TABLE 3

| SAMPLE | GENE | LOC (hg19) | REFERENCE | VARIANT | VAR FRAGS TUMOR | TUMOR TOTAL FRAGS | VAR FRAC TUMOR | PROTEIN | BLOSUM | RPKPM |
|---|---|---|---|---|---|---|---|---|---|---|
| MO_1005 | EPRS | chr1:220157596 | C | G | 12 | 77 | 0.16 | p.L1014F | 0 | 45.4 |
| MO_1005 | RBM10 | chrX:47035963 | A | G | 30 | 119 | 0.25 | p.N214S | 1 | 21.9 |
| MO_1005 | FCGR3A | chr1:161518429 | C | A | 63 | 195 | 0.34 | p.W70L, p.W69L, p.w34L | −2 | 12.6 |
| MO_1005 | STX6 | chr1:180971785 | C | A | 61 | 161 | 0.38 | p.S86I | −2 | 10.1 |
| MO_1005 | ASCC3 | chr6:101076947 | T | C | 7 | 36 | 0.19 | p.N1440S | 1 | 7.6 |
| MO_1005 | FRYL | chr4:48559517 | G | T | 6 | 52 | 0.12 | p.Q1360K | 1 | 7.3 |
| MO_1005 | ZNF711 | chrX:84525090 | A | T | 41 | 140 | 0.29 | p.N349I | −3 | 6.2 |
| MO_1005 | RNF103 | chr2:86847539 | C | T | 22 | 62 | 0.35 | p.E94K | 1 | 6.0 |
| MO_1005 | ARHGEF5 | chr7:144060459 | C | T | 23 | 57 | 0.40 | p.Q233* | −4 | 1.1 |
| MO_1005 | GLIPR1L2 | chr12:75816819 | G | C | 6 | 60 | 0.10 | p.K240N | 0 | 0.4 |
| MO_1005 | OR4K5 | chr14:20389481 | C | T | 86 | 188 | 0.46 | p.T239M | −1 | 0.2 |
| MO_1005 | SLFN14 | chr17:33884483 | T | C | 39 | 94 | 0.41 | p.E200G | −2 | 0.1 |
| MO_1005 | CLCA1 | chr1:86964441 | G | A | 34 | 92 | 0.37 | p.S767N | 1 | 0.0 |
| MO_1005 | OR2G2 | chr1:247752034 | C | T | 103 | 240 | 0.43 | p.R125C | −3 | 0.0 |

TABLE 4

| Segment (hg19) | Genes in this region | Span | Number of exons | Copy Number Ratio |
|---|---|---|---|---|
| chr3: 126260603-126260750 | CHST13 | 148 bp | 2 | 1.78 |
| chr3: 62358330-62358478 | FEZF2 | 149 bp | 2 | 1.71 |
| chr16: 72621707-72821891 | ZFHX3 | 165 bp | 2 | 1.64 |
| chr7: 114562539-114562682 | MDFIC | 144 bp | 2 | 1.63 |
| chr6: 72892426-72892819 | RIMS1 | 392 bp | 3 | 1.59 |
| chr7: 149461819-149462177 | ZNF467 | 359 bp | 3 | 1.58 |
| chr6: 30888869-30908815 | VARS2, SFTA2, DPCR | 19,947 bp | 3 | 1.45 |
| chr19: 39096074-39096826 | MAP4K1 | 753 bp | 4 | 1.41 |
| chr6: 158650956-159653511 | FNDC1 | 2554 bp | 6 | 1.33 |
| chr7: 142460789-142494836 | PRSS1, PRSS2 | 34,048 bp | 7 | 1.31 |

TABLE 5

| Segment (hg19) | Genes in this region | Span | Number of exons | Copy Number Ratio |
|---|---|---|---|---|
| chr20: 43726736-43726889 | KCNS1 | 154 bp | 2 | 0.49 |
| chr20: 61511167-61511461 | DIDO1 | 275 bp | 3 | 0.58 |
| chr14: 105617103-105617379 | JAG2 | 277 bp | 3 | 0.59 |
| chr20: 825648-825946 | FAM110A | 269 bp | 3 | 0.61 |
| chr12: 22778235-22778399 | ETNK1 | 165 bp | 2 | 0.62 |
| chr12: 57493145-57548429 | STAT6, LRP1 | 55,285 bp | 26 | 0.66 |
| chr13: 49794585-49795038 | MLNR | 454 bp | 3 | 0.68 |
| chr4: 53305141-53305907 | none | 767 bp | 7 | 0.69 |
| chr19: 45656325-45856920 | NKPD1 | 596 bp | 5 | 0.70 |

TABLE 6

| SAMPLE | 5' Gene | 3' Gene | # Supporting Reads | Type | Note |
|---|---|---|---|---|---|
| MO_1005 | NAB2 | STAT6 | 1104 | Intrachromosomal | |
| SFT-3 | NAB2 | STAT6 | 1271 | Intrachromosomal | Reciprocal |
| SFT-3 | STAT6 | NAB2 | 127 | Intrachromosomal | Reciprocal |
| SFT-3 | OXTR | ATXN10 | 4 | Intrachromosomal | |
| SFT-18 | NAB2 | STAT6 | 1943 | Intrachromosomal | Reciprocal |
| SFT-18 | STAT6 | NAB2 | 237 | Intrachromosomal | Reciprocal |
| SFT-28 | NAB2 | STAT6 | 3131 | Intrachromosomal | |
| SFT-28 | ACOX3 | AX746755 | 40 | Read-Through | |
| SFT-28 | ZDHHC16 | UBTD1 | 6 | Read-Through | |
| SFT-28 | NCOR2 | OAF | 4 | Intrachromosomal | |
| SFT-31 | NAB2 | STAT6 | 3425 | Intrachromosomal | |
| SFT-31 | ZNF337 | C15ORF26 | 12 | Intrachromosomal | |
| SFT-31 | PEPD | FXYD3 | 14 | Intrachromosomal | |
| SFT-40 | NAB2 | STAT6 | 1415 | Intrachromosomal | |
| SFT-44 | NAB2 | STAT6 | 4483 | Intrachromosomal | Reciprocal |
| SFT-44 | STAT6 | NAB2 | 119 | Intrachromosomal | Reciprocal |
| SFT-44 | SLICK | CFH | 4 | Intrachromosomal | |

TABLE 7

| Cloning of MO_1005 NAB2-STAT6 fusion allele | | SEQ ID NO |
|---|---|---|
| NAB2 FL-S1 | CAACGGTCCGACCATGCACAGAGCGCCTTCC | 31 |
| NAB2_STAT6 JUNC-AS | CCTTACCCATCTGTTCAGCTGCGAGAGGTGGCTTCGCAGG | 32 |
| NAB2_STAT6 JUNC-S | AAGCCACCTCTCGCAGCTGAACAGATGGGTAAGGATGGCA | 33 |
| STAT6 FL-AS | CAACGGACCGCAAGTGTCCAGAGCAGGTCTG | 34 |

TABLE 7-continued

| | | |
|---|---|---|
| NAB2-RT1 | CCTCAGCCTCCACTTTCACG | 35 |
| STAT6-RT1 | CAGGGGAATGATAGAAAGGAA | 36 |
| Sequencing primers | | |
| NAB2-P1 | GTACGCATGGTGGTGGAAAGTGTG | 37 |
| NAB2-P2 | GGGATGCTGGGGAGGTCACATC | 38 |
| Quantitative RT-PCR primers | | |
| NAB2STAT6 QFUS-S2 | GCTATGGAGCCGACACATCCTG | 39 |
| NAB2STAT6 QFUS-AS2 | GGAAGTGGTTGGTCCCTTTCCA | 40 |
| NAB2STAT6 SFT31-S | TGCAGCAGACACTGATGGACGAG | 41 |
| NAB2STAT6 SFT31-AS | TCTCCAGCCAGTCACCCAGAAGA | 42 |
| NAB2STAT6 SFT40-S | CCCTCCACTGAAGAAGCTGAAACAA | 43 |
| NAB2STAT6 SFT40-AS | CACTAGCCAAGTTGCAGCAGAAGG | 44 |
| IGF2 QPCR_S1 | ACCTGGCCCTCCTGGAGACG | 45 |
| IGF2 QPCR_AS1 | GGGGAAGTTGTCCGGAAGCACG | 46 |
| RRAD QPCR_S1 | GCGGCGGCGGAAACCCTAAA | 47 |
| RRAD QPCR_AS1 | CGGGACCGTCCACTCGCACA | 48 |
| H19 QPCR_S1 | GTAGGCGCCCAGGCATCGTG | 49 |
| H19 QPCR_AS1 | TCCAACCAGCTGCCACGTCC | 50 |
| Long-range genomic PCR primers | | |
| NAB2STAT6 GEN-S1 | TGTGGGGTCATGTCCAAGGCT | 51 |
| NAB2STAT6 GEN-A51 | CGGTCATCTTGATGGTAGCTGGG | 52 |

TABLE 8

| Sample ID | Tissue_Type | Status |
|---|---|---|
| ADR11 | Adrenal Gland | Cancer |
| ADR13 | Adrenal Gland | Cancer |
| BL13B | Bladder | Cancer |
| BL14A | Bladder | Cancer |
| BL14C | Bladder | Cancer |
| BL16A | Bladder | Cancer |
| BL17B | Bladder | Cancer |
| BL18C | Bladder | Cancer |
| BL18P | Bladder | Cancer |
| BL18Z | Bladder | Cancer |
| BL19B | Bladder | Cancer |
| BL19E | Bladder | Cancer |
| BL1B | Bladder | Cancer |
| BL5B | Bladder | Cancer |
| BL7C | Bladder | Cancer |
| BL8B | Bladder | Cancer |
| BL8D | Bladder | Cancer |
| ARFGEF2-SULF2-T1 | Breast | Cancer |
| ARFGEF2-SULF2-T2 | Breast | Cancer |
| BrBe10001 | Breast | Benign |
| BrBe10003 | Breast | Benign |
| BrCa10001 | Breast | Cancer |
| BrCa10002 | Breast | Cancer |
| BrCa10003 | Breast | Cancer |
| BrCa10004 | Breast | Cancer |
| BrCa10005 | Breast | Cancer |
| BrCa10006 | Breast | Cancer |
| BrCa10007 | Breast | Cancer |
| BrCa10008 | Breast | Cancer |
| BrCa10009 | Breast | Cancer |
| BrCa10010 | Breast | Cancer |
| BrCa10011 | Breast | Cancer |
| BrCa10012 | Breast | Cancer |
| BrCa10013 | Breast | Cancer |
| BrCa10014 | Breast | Cancer |
| BrCa10015 | Breast | Cancer |
| BrCa10016 | Breast | Cancer |
| BrCa10017 | Breast | Cancer |
| BrCa10018 | Breast | Cancer |
| BrCa10020 | Breast | Cancer |
| BrCa10021 | Breast | Cancer |
| BrCa10022 | Breast | Cancer |
| BrCa10023 | Breast | Cancer |
| BrCa10024 | Breast | Cancer |
| BrCa10025 | Breast | Cancer |
| BrCa10026 | Breast | Cancer |
| BrCa10027 | Breast | Cancer |
| BrCa10028 | Breast | Cancer |
| BrCa10029 | Breast | Cancer |
| BrCa10030 | Breast | Cancer |
| BrCa10031 | Breast | Cancer |
| BrCa10032 | Breast | Cancer |
| BrCa10033 | Breast | Cancer |
| BrCa10034 | Breast | Cancer |
| BrCa10035 | Breast | Cancer |
| BrCa10036 | Breast | Cancer |
| BrCa10037 | Breast | Cancer |
| Brst104_LN | Breast | Cancer |
| Brst106_LN | Breast | Cancer |
| Brst33_LN | Breast | Cancer |
| Brst35_T | Breast | Cancer |
| Brst36_89_N | Breast | Benign |

TABLE 8-continued

| Sample ID | Tissue_Type | Status |
|---|---|---|
| Brst37_T | Breast | Cancer |
| Brst38_T | Breast | Cancer |
| Brst39_T | Breast | Cancer |
| Brst40_T | Breast | Cancer |
| Brst42_N | Breast | Benign |
| Brst47_T | Breast | Cancer |
| Brst52_100_T | Breast | Cancer |
| Brst57_T | Breast | Cancer |
| Brst61_LN | Breast | Cancer |
| Brst62_T | Breast | Cancer |
| Brst63_T | Breast | Cancer |
| Brst66_T | Breast | Cancer |
| Brst72_T | Breast | Cancer |
| Brst74_LN | Breast | Cancer |
| Brst79_T | Breast | Cancer |
| Brst82_T | Breast | Cancer |
| Brst84_T | Breast | Cancer |
| Brst93_T | Breast | Cancer |
| Brst94_T | Breast | Cancer |
| Brst95_N | Breast | Benign |
| MCTP0484_T | Breast | Cancer |
| MCTP0485_T | Breast | Cancer |
| MCTP0486_T | Breast | Cancer |
| MCTP0487_T | Breast | Cancer |
| MCTP0488_T | Breast | Cancer |
| MCTP0490_T | Breast | Cancer |
| MCTP0491_T | Breast | Cancer |
| NO41B1 | Colon | Benign |
| NO43B1 | Colon | Benign |
| NO52B1 | Colon | Benign |
| NO53B1 | Colon | Benign |
| NO8B1 | Colon | Benign |
| UCNP11B1 | Colon | Benign |
| UCNP61B1 | Colon | Benign |
| UCNP71B1 | Colon | Benign |
| UCNP75B1 | Colon | Benign |
| UCP6B2 | Colon | Benign |
| UCP77B2 | Colon | Benign |
| GCN-2000256 | Gastric | Benign |
| GCN-2000521 | Gastric | Benign |
| GCN-20020032 | Gastric | Benign |
| GCN-970005 | Gastric | Benign |
| GCN-980028 | Gastric | Benign |
| GCT-2000256 | Gastric | Cancer |
| GCT-2000521 | Gastric | Cancer |
| GCT-20020032 | Gastric | Cancer |
| GCT-200479 | Gastric | Cancer |
| GCT-47149013 | Gastric | Cancer |
| GCT-980025 | Gastric | Cancer |
| GCT-980028 | Gastric | Cancer |
| GCT-76629543 | Gastric | Cancer |
| GCT-970005 | Gastric | Cancer |
| GCT-980211 | Gastric | Cancer |
| GCT-980269 | Gastric | Cancer |
| GCT-990071 | Gastric | Cancer |
| Ambion_normal_lung | Lung | Benign |
| Clontech_normal_lung | Lung | Benign |
| L26 | Lung | Cancer |
| L33 | Lung | Cancer |
| L36 | Lung | Cancer |
| L39 | Lung | Cancer |
| C41-2 | Lymphoma | Cancer |
| C60 | Lymphoma | Cancer |
| D50 | Lymphoma | Cancer |
| E58-1 | Lymphoma | Cancer |
| F78 | Lymphoma | Cancer |
| G17 | Lymphoma | Cancer |
| MeBe10001 | Melanocyte | Benign |
| MEL13 | Melanoma | Cancer |
| MEL41 | Melanoma | Cancer |
| MEL52 | Melanoma | Cancer |
| MEL56 | Melanoma | Cancer |
| MEL58 | Melanoma | Cancer |
| MEL74 | Melanoma | Cancer |
| MEL83 | Melanoma | Cancer |
| MeBe10002 | Melanoma | Benign |
| MCC-1 | Merkel | Cancer |
| MCC-2 | Merkel | Cancer |
| MCC-3 | Merkel | Cancer |
| DS13_T | Pancreas | Cancer |
| DS15_T | Pancreas | Cancer |
| DS18_T | Pancreas | Cancer |
| DS416_T_xeno | Pancreas | Cancer |
| DS420_N | Pancreas | Cancer |
| DS459_T | Pancreas | Cancer |
| DS577_T_xeno | Pancreas | Cancer |
| DS597_T_xeno | Pancreas | Cancer |
| DS825_T | Pancreas | Cancer |
| DS844_T | Pancreas | Cancer |
| DS848_N | Pancreas | Benign |
| DSF82_T_xeno | Pancreas | Cancer |
| Pen-10DA_T | Pancreas | Cancer |
| Pen-9A_T | Pancreas | Cancer |
| Pen4 | Pancreas | Cancer |
| MCTP-0529 | Prostate | Cancer |
| MCTP-0534 | Prostate | Cancer |
| MDA-PCa-153-7 | Prostate | Cancer |
| MDA-PCa-163-A | Prostate | Cancer |
| PrBe10002 | Prostate | Benign |
| PrBe10003 | Prostate | Benign |
| PrBe10013 | Prostate | Benign |
| PrBe10014 | Prostate | Benign |
| PrBe10015 | Prostate | Benign |
| PrBe10016 | Prostate | Benign |
| PrBe10017 | Prostate | Benign |
| PrBe10018 | Prostate | Benign |
| PrCa10001 | Prostate | Cancer |
| PrCa10002 | Prostate | Cancer |
| PrCa10003 | Prostate | Cancer |
| PrCa10004 | Prostate | Cancer |
| PrCa10006 | Prostate | Cancer |
| PrCa10007 | Prostate | Cancer |
| PrCa10013 | Prostate | Cancer |
| PrCa10014 | Prostate | Cancer |
| PrCa10015 | Prostate | Cancer |
| PrCa10016 | Prostate | Cancer |
| PrCa10017 | Prostate | Cancer |
| PrCa10018 | Prostate | Cancer |
| PrCa10019 | Prostate | Cancer |
| PrCa10021 | Prostate | Cancer |
| PrCa10023 | Prostate | Cancer |
| PrCa10024 | Prostate | Cancer |
| PrCa10025 | Prostate | Cancer |
| PrCa10026 | Prostate | Cancer |
| PrCa10027 | Prostate | Cancer |
| PrCa10028 | Prostate | Cancer |
| PrCa10029 | Prostate | Cancer |
| PrCa10030 | Prostate | Cancer |
| PrCa10031 | Prostate | Cancer |
| PrCa10032 | Prostate | Cancer |
| PrCa10033 | Prostate | Cancer |
| PrCa10034 | Prostate | Cancer |
| PrCa10035 | Prostate | Cancer |
| PrCa10036 | Prostate | Cancer |
| PrCa10037 | Prostate | Cancer |
| PrCa10038 | Prostate | Cancer |
| PrMe10009 | Prostate | Cancer |
| PrMe10010 | Prostate | Cancer |
| PrMe10011 | Prostate | Cancer |
| PrMe10012 | Prostate | Cancer |
| TMP-am23 | Prostate | Cancer |
| ULM2927 | Prostate | Cancer |
| ULM4340 | Prostate | Cancer |
| ULM792 | Prostate | Cancer |
| ULMB11239-97 | Prostate | Cancer |
| ULMB2440-97 | Prostate | Cancer |
| aM15 | Prostate | Cancer |
| aM16 | Prostate | Cancer |
| aM17 | Prostate | Cancer |
| aM20 | Prostate | Cancer |
| aM21 | Prostate | Cancer |
| aM22 | Prostate | Cancer |
| aM23 | Prostate | Cancer |
| aM26 | Prostate | Cancer |
| aM28 | Prostate | Cancer |
| aM29 | Prostate | Cancer |

TABLE 8-continued

| Sample ID | Tissue_Type | Status |
|---|---|---|
| aM31 | Prostate | Cancer |
| aM33 | Prostate | Cancer |
| aM36 | Prostate | Cancer |
| aM37 | Prostate | Cancer |
| aM38 | Prostate | Cancer |
| aM39 | Prostate | Cancer |
| aM40 | Prostate | Cancer |
| aM41 | Prostate | Cancer |
| aM44 | Prostate | Cancer |
| aM59 | Prostate | Cancer |
| aM6 | Prostate | Cancer |
| aM7 | Prostate | Cancer |
| aN10-6 | Prostate | Benign |
| aN11-1 | Prostate | Benign |
| aN13-2 | Prostate | Benign |
| aN14-4 | Prostate | Benign |
| aN15-3 | Prostate | Benign |
| aN23 | Prostate | Benign |
| aN25 | Prostate | Benign |
| aN27 | Prostate | Benign |
| aN29 | Prostate | Benign |
| aN31 | Prostate | Benign |
| aN32 | Prostate | Benign |
| aN33 | Prostate | Benign |
| aT12_4 | Prostate | Cancer |
| aT1_3 | Prostate | Cancer |
| aT20 | Prostate | Cancer |
| aT38 | Prostate | Cancer |
| aT42 | Prostate | Cancer |
| aT45 | Prostate | Cancer |
| aT47 | Prostate | Cancer |
| aT49 | Prostate | Cancer |
| aT52 | Prostate | Cancer |
| aT53 | Prostate | Cancer |
| aT54 | Prostate | Cancer |
| aT56 | Prostate | Cancer |
| aT57 | Prostate | Cancer |
| aT58 | Prostate | Cancer |
| aT5_5 | Prostate | Cancer |
| aT61 | Prostate | Cancer |
| aT62 | Prostate | Cancer |
| aT64 | Prostate | Cancer |
| aT65 | Prostate | Cancer |
| aT66 | Prostate | Cancer |
| aT67 | Prostate | Cancer |
| a76_1 | Prostate | Cancer |
| aT76 | Prostate | Cancer |
| aT6_2 | Prostate | Cancer |
| K11T | Renal | Cancer |
| K13T | Renal | Cancer |
| K14T | Renal | Cancer |
| K16T | Renal | Cancer |
| K18T | Renal | Cancer |
| K19T | Renal | Cancer |
| K20T | Renal | Cancer |
| K2T | Renal | Cancer |
| K3T | Renal | Cancer |
| K5T | Renal | Cancer |
| K7T | Renal | Cancer |
| K6T | Renal | Cancer |
| AC1-T | Salivary Gland | Cancer |
| AC3-T | Salivary Gland | Cancer |
| ME2-T | Salivary Gland | Cancer |
| ME3-T | Salivary Gland | Cancer |

TABLE 9

| Gene | Number of Outlier Samples | Gene Expression (RPKM), Bold = Outlier | | | | | | |
|---|---|---|---|---|---|---|---|---|
| | | MO_1005 | SFT3 | SFT18 | SFT28 | SFT31 | SFT40 | SFT44 |
| A8HD14A | 4 | 64.3 | 43.3 | 20.1 | 69.6 | 13.7 | 5.5 | 68.0 |
| ABI2 | 4 | 18.0 | 26.1 | 26.0 | 20.2 | 36.5 | 36.0 | 14.3 |
| ACCN2 | 4 | 70.4 | 90.9 | 1.3 | 36.1 | 0.5 | 19.5 | 25.4 |
| ADAMTSL5 | 4 | 9.9 | 20.6 | 25.7 | 23.5 | 12.6 | 8.2 | 34.7 |
| AF136186 | 3 | 526.8 | 14.5 | 892.2 | 394.8 | 0.2 | 103.9 | 893.2 |
| AFAP1L2 | 2 | 8.9 | 2.1 | 17.0 | 14.8 | 51.2 | 14.1 | 53.6 |
| AHDC1 | 6 | 41.8 | 38.9 | 59.9 | 38.6 | 58.2 | 25.7 | 34.1 |
| AK055602 | 3 | 4.3 | 76.0 | 120.3 | 30.3 | 228.0 | 45.1 | 130.8 |
| AK074994 | 3 | 1.5 | 5.7 | 10.5 | 149.6 | 8.6 | 29.3 | 25.5 |
| AK092048 | 4 | 50.4 | 52.6 | 51.1 | 73.5 | 0.1 | 20.2 | 11.3 |
| AK092715 | 3 | 36.2 | 41.3 | 16.7 | 61.3 | 2.1 | 15.4 | 5.0 |
| AK095458 | 3 | 967.2 | 466.3 | 218.2 | 74.5 | 1494.3 | 340.6 | 380.6 |
| AK123035 | 2 | 37.4 | 23.2 | 60.0 | 12.3 | 10.2 | 20.1 | 65.3 |
| AK308561:1 | 4 | 6.8 | 34.2 | 31.5 | 135.7 | 2.0 | 16.8 | 57.3 |
| AK308561:2 | 4 | 5.4 | 24.4 | 20.3 | 70.4 | 1.0 | 12.6 | 36.5 |
| AL883195A | 3 | 23.4 | 0.7 | 12.6 | 12.1 | 53.2 | 11.5 | 41.6 |
| ALKBH5 | 3 | 79.1 | 110.8 | 145.8 | 77.9 | 76.0 | 149.0 | 94.5 |
| ALX4 | 7 | 155.6 | 142.8 | 101.3 | 97.7 | 98.9 | 79.7 | 122.8 |
| AQP5 | 3 | 85.6 | 182.8 | 3.9 | 39.7 | 0.1 | 5.3 | 239.7 |
| AQP6 | 3 | 34.1 | 46.6 | 0.5 | 20.6 | 0.2 | 3.5 | 19.4 |
| argBPIB | 4 | 18.5 | 26.9 | 25.1 | 21.7 | 32.6 | 35.3 | 14.8 |
| ARMCX2 | 2 | 33.9 | 32.3 | 21.3 | 11.6 | 17.8 | 12.0 | 8.1 |
| ATP2B4 | 5 | 14.2 | 152.7 | 162.4 | 225.4 | 223.5 | 115.6 | 74.1 |
| B4GALNT1 | 2 | 19.0 | 11.3 | 57.4 | 11.3 | 7.9 | 38.2 | 22.6 |
| BAHCC1 | 5 | 80.6 | 60.8 | 81.3 | 77.6 | 31.2 | 0.7 | 74.0 |
| BAI1 | 4 | 9.7 | 24.5 | 10.3 | 41.3 | 27.4 | 3.6 | 29.5 |
| BC006113 | 2 | 1.2 | 0.5 | 2.1 | 22.1 | 0.6 | 3.8 | 70.5 |
| BC010054 | 2 | 101.9 | 1278.0 | 1982.5 | 157.0 | 621.8 | 2056.6 | 755.0 |
| BC034684 | 2 | 1940.9 | 944.6 | 484.0 | 201.8 | 3241.9 | 686.5 | 785.9 |
| BC080605 | 5 | 18.2 | 71.4 | 70.2 | 354.6 | 3.4 | 29.4 | 138.4 |
| BC110369 | 2 | 3.9 | 19.2 | 17.6 | 75.7 | 1.8 | 9.4 | 31.9 |
| BCL2 | 3 | 6.2 | 20.7 | 28.5 | 0.5 | 14.8 | 22.1 | 12.5 |
| BCOR | 4 | 68.6 | 50.2 | 32.8 | 119.8 | 22.4 | 11.7 | 64.6 |
| BGN | 2 | 2330.5 | 155.6 | 110.7 | 1581.6 | 13.2 | 85.5 | 49.9 |
| BHMT | 2 | 96.2 | 100.0 | 2.3 | 0.2 | 0.3 | 1.3 | 10.4 |
| BMP5 | 3 | 44.2 | 45.5 | 20.1 | 32.1 | 0.2 | 0.7 | 44.2 |

TABLE 9-continued

| Gene | Number of Outlier Samples | Gene Expression (RPKM), Bold = Outlier | | | | | |
|---|---|---|---|---|---|---|---|
| | | MO_1005 | SFT3 | SFT18 | SFT28 | SFT31 | SFT40 | SFT44 |
| BOC | 3 | 56.3 | 19.7 | 37.0 | 107.4 | 23.9 | 24.0 | 71.7 |
| Borg4 | 3 | 166.3 | 75.1 | 118.2 | 120.9 | 287.9 | 42.6 | 107.2 |
| C1orf92 | 3 | 16.5 | 48.3 | 46.2 | 27.1 | 12.4 | 17.7 | 8.8 |
| C1QL1 | 5 | 47.8 | 118.0 | 34.7 | 82.7 | 1.5 | 12.3 | 34.6 |
| C1QL4 | 3 | 0.3 | 2.2 | 182.7 | 4.2 | 0.6 | 133.0 | 74.9 |
| C1QTNF4 | 2 | 0.7 | 9.3 | 12.1 | 11.3 | 14.2 | 33.5 | 104.8 |
| C5orf46 | 2 | 65.6 | 0.7 | 0.1 | 39.3 | 0.0 | 0.8 | 0.2 |
| C9orf41 | 3 | 12.9 | 22.5 | 25.7 | 6.4 | 24.2 | 6.5 | 12.6 |
| CA11 | 7 | 176.5 | 127.7 | 95.6 | 138.4 | 168.0 | 47.9 | 80.2 |
| CACNA2D1 | 3 | 21.3 | 28.6 | 29.6 | 12.9 | 0.1 | 13.7 | 6.5 |
| CCD543604 | 6 | 37.0 | 31.9 | 40.1 | 19.9 | 24.9 | 65.6 | 24.1 |
| CCR10 | 3 | 30.4 | 17.6 | 49.6 | 9.2 | 7.5 | 15.0 | 56.1 |
| CDC42EP4 | 2 | 162.0 | 72.9 | 115.0 | 113.9 | 283.1 | 41.7 | 103.8 |
| CDH24 | 5 | 62.7 | 209.7 | 91.2 | 416.6 | 151.3 | 137.5 | 202.7 |
| CDO1 | 2 | 33.1 | 75.1 | 15.8 | 12.2 | 33.7 | 16.6 | 336.4 |
| CELSR2 | 2 | 50.2 | 0.9 | 0.5 | 59.5 | 21.7 | 0.1 | 12.3 |
| CERCAM | 7 | 112.3 | 88.4 | 135.5 | 83.5 | 134.6 | 77.2 | 55.7 |
| CFH | 5 | 678.0 | 547.5 | 242.2 | 166.7 | 87.7 | 2.6 | 367.1 |
| CHAD | 4 | 854.5 | 108.5 | 9.8 | 165.8 | 3.1 | 1.9 | 57139 |
| CHI3L1 | 3 | 1660.9 | 849.7 | 385.0 | 110.9 | 3020.3 | 568.5 | 668.9 |
| CLEC4F | 3 | 14.8 | 1.6 | 3.2 | 58.0 | 76.1 | 16.3 | 48.0 |
| CLSTN3 | 2 | 21.7 | 20.8 | 35.0 | 13.7 | 41.4 | 24.9 | 12.4 |
| CMKLR1 | 3 | 4.1 | 15.9 | 32.9 | 4.1 | 36.9 | 74.4 | 11.3 |
| COL11A2:1 | 4 | 8.3 | 36.6 | 29.5 | 22.2 | 2.9 | 3.2 | 25.1 |
| COL17A1 | 3 | 372.1 | 10.7 | 649.6 | 115.6 | 0.1 | 81.8 | 530.3 |
| COL1A1 | 2 | 1544.3 | 392.2 | 732.4 | 840.2 | 9.6 | 3766.5 | 120.6 |
| COL8A2 | 2 | 55.1 | 28.1 | 18.5 | 28.9 | 12.7 | 23.7 | 110.5 |
| COMP | 4 | 251.8 | 340.4 | 20.9 | 268.3 | 1.0 | 18.0 | 323.4 |
| CPT1C | 2 | 20.5 | 7.8 | 13.5 | 14.6 | 15.3 | 13.8 | 23.7 |
| CPXM1 | 5 | 79.7 | 617.2 | 16.1 | 150.1 | 64.9 | 119.2 | 223.2 |
| CPZ | 5 | 30.7 | 260.8 | 374.7 | 119.5 | 1.0 | 124.8 | 83.0 |
| CR594717 | 2 | 86.6 | 1083.1 | 1683.8 | 134.0 | 527.7 | 1739.7 | 635.2 |
| CR596119 | 3 | 130.0 | 1568.9 | 2528.7 | 219.8 | 780.1 | 2620.9 | 949.1 |
| CR597604 | 2 | 80.1 | 1021.6 | 1558.4 | 120.6 | 491.2 | 1624.3 | 601.0 |
| CR598488 | 2 | 5.8 | 37.6 | 7.1 | 33.8 | 0.3 | 2.8 | 5.2 |
| CR607033 | 2 | 93.7 | 1176.4 | 1823.5 | 144.3 | 571.9 | 1892.7 | 695.0 |
| CR617227 | 2 | 30.6 | 4.5 | 23.4 | 10.2 | 90.0 | 94.4 | 5.9 |
| CRTAC1 | 3 | 1.6 | 17.3 | 58.2 | 2.9 | 6.9 | 143.5 | 28.8 |
| CTXN1 | 2 | 99.6 | 53.8 | 128.5 | 75.5 | 22.3 | 11.8 | 197.2 |
| CXXC5 | 3 | 70.1 | 59.1 | 95.9 | 87.1 | 12.1 | 5.9 | 16.7 |
| CYP11A1 | 4 | 41.4 | 20.8 | 18.3 | 39.1 | 3.0 | 18.9 | 78.0 |
| D87946 | 6 | 79.4 | 51.3 | 42.5 | 52.6 | 65.7 | 19.7 | 37.1 |
| D87947 | 6 | 46.6 | 30.2 | 25.0 | 31.4 | 38.9 | 11.6 | 21.7 |
| DAGLA | 4 | 5.3 | 9.3 | 64.1 | 9.4 | 63.8 | 47.5 | 42.0 |
| DISP1 | 2 | 21.8 | 11.4 | 4.9 | 43.1 | 17.1 | 4.2 | 15.4 |
| DKFZp434D2030 | 2 | 26.8 | 35.6 | 1.4 | 16.1 | 0.2 | 3.0 | 13.8 |
| DKFZp434K2323 | 5 | 81.3 | 263.8 | 123.3 | 680.6 | 179.4 | 172.0 | 274.1 |
| DKFZp686A1849 | 2 | 0.5 | 4.7 | 21.0 | 0.2 | 34.2 | 19.2 | 12.1 |
| DKFZp761D0614 | 5 | 21.0 | 48.6 | 23.4 | 82.8 | 19.3 | 31.7 | 12.5 |
| DKK1 | 2 | 72.7 | 9.6 | 10.2 | 16.7 | 12.6 | 0.5 | 105.7 |
| DLX3 | 3 | 89.4 | 69.1 | 22.0 | 80.3 | 0.8 | 0.5 | 8.6 |
| DLX4 | 4 | 106.6 | 74.0 | 60.7 | 193.8 | 1.4 | 0.9 | 13.1 |
| DMXL2 | 2 | 8.5 | 15.5 | 6.3 | 19.8 | 32.9 | 26.0 | 15.3 |
| DNALI1 | 2 | 32.2 | 21.3 | 29.2 | 50.0 | 32.6 | 8.7 | 42.5 |
| DOK5 | 2 | 17.9 | 7.3 | 13.8 | 20.7 | 4.3 | 9.7 | 44.5 |
| DPYS | 2 | 38.9 | 23.3 | 1.9 | 0.1 | 10.7 | 0.4 | 1.8 |
| DQ595431 | 6 | 33.2 | 22.9 | 25.8 | 19.4 | 27.1 | 22.4 | 25.1 |
| DSE | 2 | 14.5 | 21.4 | 48.8 | 8.6 | 49.4 | 11.7 | 6.3 |
| ECEL1 | 2 | 83.8 | 41.9 | 10.9 | 24.7 | 79.3 | 1.3 | 0.1 |
| EFNA2 | 4 | 48.4 | 106.4 | 1.5 | 96.6 | 0.1 | 0.1 | 178.6 |
| EGFLAM | 2 | 7.1 | 11.1 | 1.1 | 8.3 | 31.9 | 31.1 | 14.5 |
| ELFN1 | 2 | 0.8 | 20.7 | 10.3 | 37.6 | 6.0 | 9.7 | 0.7 |
| EMILN2 | 2 | 9.8 | 23.4 | 80.9 | 17.4 | 40.4 | 36.4 | 191.6 |
| ENC1 | 2 | 4.8 | 2.5 | 3.0 | 1.6 | 239.7 | 89.6 | 1.6 |
| EPHB3 | 3 | 53.9 | 65.1 | 19.0 | 62.9 | 0.8 | 49.1 | 82.1 |
| EPYC | 2 | 0.1 | 0.4 | 97.6 | 534.0 | 6.5 | 3.9 | 7.6 |
| ESM1 | 2 | 4.7 | 6.2 | 25.5 | 20.2 | 0.2 | 6.0 | 2.8 |
| FAIM2 | 2 | 31.5 | 10.7 | 14.9 | 8.7 | 3.8 | 44.8 | 11.5 |
| FAP | 2 | 5.8 | 8.8 | 13.6 | 0.4 | 13.3 | 40.4 | 25.8 |
| FBLN1 | 2 | 65.7 | 65.1 | 1029.7 | 52.0 | 1055.5 | 283.3 | 553.2 |
| FEZF2 | 4 | 0.1 | 98.9 | 25.4 | 0.1 | 0.0 | 37.8 | 34.3 |
| FGF2 | 2 | 13.9 | 30.3 | 22.1 | 7.9 | 8.1 | 9.3 | 11.3 |
| FGFR1 | 6 | 47.1 | 178.9 | 219.9 | 114.7 | 224.1 | 234.1 | 238.2 |
| FKSG40 | 6 | 51.0 | 335.5 | 111.3 | 113.1 | 55.6 | 18.3 | 294.3 |
| FLI00193 | 6 | 83.0 | 149.7 | 151.6 | 143.6 | 66.9 | 32.4 | 68.2 |
| FLI37078 | 2 | 17.5 | 16.1 | 20.2 | 8.2 | 11.6 | 31.2 | 13.7 |

TABLE 9-continued

| Gene | Number of Outlier Samples | Gene Expression (RPKM), Bold = Outlier | | | | | |
|---|---|---|---|---|---|---|---|
| | | MO_1005 | SFT3 | SFT18 | SFT28 | SFT31 | SFT40 | SFT44 |
| FLJ37464 | 3 | 28.6 | 11.8 | 16.2 | 27.4 | 26.5 | 17.1 | 8.2 |
| FOXP4 | 6 | 169.0 | 190.3 | 144.9 | 158.0 | 50.5 | 127.8 | 182.3 |
| FRS2 | 2 | 8.4 | 8.5 | 28.6 | 18.5 | 14.5 | 21.5 | 13.8 |
| FZD7 | 4 | 6.7 | 181.7 | 76.9 | 21.5 | 26.0 | 85.4 | 104.6 |
| GFRAL | 2 | 23.3 | 0.0 | 0.3 | 2.4 | 0.0 | 0.0 | 33.1 |
| Gli2 | 4 | 13.4 | 16.4 | 42.9 | 15.5 | 37.3 | 36.3 | 20.3 |
| GLI2 | 6 | 17.5 | 24.3 | 52.4 | 25.1 | 36.8 | 42.8 | 30.9 |
| GLS | 2 | 39.5 | 20.2 | 15.4 | 43.4 | 6.4 | 10.1 | 9.9 |
| GP1BB | 3 | 28.9 | 35.7 | 52.8 | 60.3 | 13.0 | 29.0 | 122.0 |
| GPC4 | 3 | 103.4 | 57.6 | 5.8 | 0.2 | 14.7 | 9.0 | 203.0 |
| GPM6B | 3 | 28.7 | 2.6 | 212.1 | 168.9 | 5.7 | 32.3 | 170.3 |
| GPR162 | 2 | 10.5 | 6.3 | 9.6 | 28.2 | 14.8 | 7.5 | 25.5 |
| GPR78 | 5 | 18.0 | 150.3 | 217.7 | 70.6 | 0.6 | 71.7 | 48.0 |
| GPR88 | 7 | 52.9 | 57.2 | 205.1 | 24.2 | 198.5 | 99.7 | 151.1 |
| GRIA2 | 4 | 10.7 | 108.8 | 62.5 | 0.1 | 25.5 | 166.1 | 0.1 |
| GSN | 3 | 712.6 | 2319.7 | 2208.5 | 200.3 | 722.5 | 1070.6 | 1826.9 |
| HDAC9 | 2 | 22.1 | 11.6 | 17.4 | 20.3 | 7.2 | 10.6 | 16.1 |
| HECTD2 | 3 | 15.1 | 35.8 | 17.2 | 60.5 | 14.7 | 24.0 | 9.2 |
| hGLi2 | 6 | 18.0 | 25.0 | 53.0 | 26.3 | 36.4 | 43.4 | 32.0 |
| HOXB3 | 5 | 1.2 | 98.7 | 54.0 | 1.8 | 54.9 | 34.3 | 31.0 |
| HOXB6 | 2 | 0.4 | 22.2 | 12.7 | 0.5 | 45.7 | 2.8 | 31.2 |
| HOXB8 | 3 | 0.1 | 41.7 | 16.5 | 0.4 | 26.2 | 1.2 | 43.0 |
| HOXC10 | 7 | 99.1 | 155.5 | 98.7 | 417.7 | 137.4 | 72.4 | 228.0 |
| HOXC11 | 7 | 63.8 | 96.8 | 77.0 | 70.3 | 63.7 | 44.7 | 117.8 |
| HOXC12 | 6 | 30.7 | 40.9 | 41.7 | 27.3 | 26.2 | 0.4 | 94.5 |
| HOXC13 | 6 | 40.2 | 24.6 | 42.7 | 33.5 | 22.7 | 1.3 | 70.1 |
| HOXC4 | 7 | 90.3 | 52.0 | 46.5 | 109.5 | 46.8 | 55.3 | 63.8 |
| HOXC5 | 7 | 32.1 | 26.9 | 20.9 | 48.9 | 23.3 | 23.0 | 22.6 |
| HOXC6 | 7 | 128.1 | 90.2 | 57.4 | 165.0 | 57.7 | 60.7 | 86.4 |
| HOXC8 | 7 | 44.9 | 43.2 | 33.5 | 157.8 | 22.2 | 28.6 | 32.8 |
| HOXC9 | 2 | 95.8 | 57.5 | 45.3 | 98.0 | 23.8 | 31.2 | 62.0 |
| HSD11B1 | 5 | 126.7 | 57.5 | 82.1 | 11.3 | 4.7 | 81.4 | 139.6 |
| IGF1 | 2 | 43.0 | 2.6 | 11.3 | 1.4 | 9.5 | 160.8 | 14.2 |
| IGF2 | 7 | 3169.1 | 4851.2 | 3275.5 | 11939.1 | 12992.3 | 4698.0 | 9851.7 |
| IGF2AS | 7 | 33.7 | 51.1 | 21.4 | 46.7 | 47.0 | 24.2 | 106.7 |
| IL11RA | 6 | 46.8 | 140.0 | 58.0 | 52.2 | 36.8 | 28.0 | 52.0 |
| INS-IGF2 | 7 | 3687.9 | 5616.8 | 3804.4 | 14003.5 | 14716.8 | 5393.3 | 11495.2 |
| IQSEC3 | 4 | 12.2 | 28.2 | 31.9 | 8.5 | 28.7 | 36.3 | 14.0 |
| ISLR | 6 | 980.0 | 1004.0 | 371.3 | 1250.7 | 232.6 | 277.6 | 1225.4 |
| ISYNA1 | 2 | 82.6 | 63.0 | 42.9 | 57.9 | 134.1 | 11.5 | 108.9 |
| KAZALD1 | 6 | 64.6 | 415.4 | 140.6 | 126.8 | 79.9 | 27.2 | 303.2 |
| KCNAB3 | 2 | 20.9 | 19.5 | 7.1 | 37.6 | 4.7 | 7.7 | 13.6 |
| KCNC1 | 3 | 20.2 | 14.1 | 0.1 | 80.6 | 0.0 | 0.4 | 31.8 |
| KCTD1 | 6 | 116.0 | 2.9 | 62.3 | 52.7 | 248.2 | 49.0 | 187.2 |
| KERA | 2 | 0.0 | 0.0 | 151.9 | 267.8 | 6.1 | 10.6 | 3.0 |
| KHDRBS3 | 2 | 3.3 | 2.2 | 5.4 | 2.6 | 62.3 | 52.9 | 10.1 |
| KIAA0182 | 7 | 54.0 | 63.4 | 107.2 | 83.9 | 156.5 | 99.3 | 59.2 |
| KIAA0638 | 2 | 36.7 | 143.1 | 123.5 | 63.5 | 84.2 | 211.0 | 149.1 |
| KIAA0709:1 | 5 | 308.1 | 253.4 | 253.0 | 161.9 | 187.9 | 319.4 | 399.2 |
| KIAA0709:2 | 6 | 270.8 | 232.4 | 235.0 | 54.4 | 207.0 | 324.7 | 274.4 |
| KIAA0827:2 | 2 | 13.1 | 24.6 | 20.5 | 49.5 | 11.2 | 11.8 | 11.9 |
| KIAA0856 | 4 | 33.5 | 44.1 | 16.3 | 64.2 | 53.4 | 62.4 | 40.5 |
| KIAA0897 | 2 | 31.9 | 8.8 | 36.8 | 17.6 | 11.6 | 16.1 | 4.3 |
| KIAA0950 | 2 | 37.4 | 12.6 | 17.7 | 10.2 | 4.5 | 53.4 | 13.7 |
| KIAA0957 | 2 | 24.3 | 22.6 | 5.6 | 12.1 | 3.4 | 6.6 | 11.2 |
| KIAA1171 | 2 | 2.9 | 4.2 | 27.1 | 2.4 | 28.2 | 11.7 | 2.9 |
| KIAA1308 | 2 | 71.4 | 63.5 | 49.5 | 81.6 | 17.6 | 8.8 | 67.7 |
| KIAA1350 | 2 | 4.6 | 2.3 | 80.6 | 87.3 | 40.6 | 6.2 | 12.8 |
| KIAA1444 | 2 | 34.1 | 1.1 | 6.0 | 46.8 | 0.4 | 11.1 | 10.7 |
| KIAA1462 | 2 | 2.3 | 48.9 | 99.6 | 9.3 | 266.2 | 37.1 | 37.8 |
| KIAA1482 | 4 | 61.6 | 24.9 | 48.4 | 78.8 | 6.2 | 36.7 | 52.1 |
| KIAA1520 | 2 | 25.1 | 11.2 | 10.1 | 13.4 | 4.6 | 2.4 | 24.3 |
| KIAA1547 | 5 | 65.5 | 79.5 | 84.8 | 72.6 | 24.9 | 24.2 | 82.7 |
| LAG3 | 5 | 17.1 | 81.8 | 135.9 | 13.6 | 34.7 | 44.9 | 283.9 |
| LHX2 | 2 | 5.0 | 70.7 | 0.7 | 0.2 | 0.0 | 11.1 | 20.7 |
| LMO4 | 2 | 364.5 | 104.7 | 28.1 | 300.8 | 33.5 | 57.6 | 201.4 |
| LOC126520 | 3 | 3.9 | 52.0 | 31.4 | 10.8 | 5.5 | 0.2 | 49.2 |
| LOC284297 | 2 | 180.3 | 58.9 | 26.6 | 292.7 | 25.9 | 5.9 | 40.7 |
| LOC404266 | 3 | 0.1 | 57.9 | 32.3 | 0.0 | 14.4 | 20.5 | 13.4 |
| LOC91461 | 7 | 316.5 | 303.0 | 147.9 | 505.4 | 280.7 | 258.6 | 322.2 |
| LPHN1 | 5 | 15.6 | 33.5 | 27.1 | 35.5 | 32.7 | 18.9 | 42.0 |
| LRCH2 | 2 | 20.3 | 6.1 | 0.4 | 49.0 | 6.8 | 3.8 | 7.1 |
| LRP3 | 4 | 61.9 | 112.3 | 94.3 | 50.0 | 78.5 | 55.0 | 199.3 |
| LSP1 | 4 | 250.9 | 255.6 | 230.2 | 369.4 | 208.5 | 98.4 | 517.5 |
| MAP3K12 | 2 | 37.1 | 30.6 | 25.3 | 42.6 | 50.7 | 27.4 | 16.4 |
| MCOLN3 | 3 | 62.9 | 0.3 | 5.7 | 0.7 | 197.5 | 49.9 | 0.1 |

TABLE 9-continued

| Gene | Number of Outlier Samples | Gene Expression (RPKM), Bold = Outlier | | | | | |
|---|---|---|---|---|---|---|---|
| | | MO_1005 | SFT3 | SFT18 | SFT28 | SFT31 | SFT40 | SFT44 |
| MPDZ | 2 | 25.3 | 32.4 | 63.9 | 22.2 | 22.1 | 23.3 | 18.3 |
| MPDZ_variant_protien | 4 | 31.7 | 37.3 | 71.7 | 31.4 | 22.3 | 25.1 | 21.6 |
| MRC2 | 6 | 286.4 | 244.3 | 250.1 | 114.7 | 215.0 | 329.4 | 341.3 |
| MST123 | 6 | 67.7 | 243.2 | 304.4 | 196.1 | 285.9 | 308.3 | 356.8 |
| MUM1 | 2 | 34.5 | 22.9 | 24.6 | 32.0 | 7.9 | 12.5 | 28.2 |
| MXRA5 | 4 | 28.3 | 405.9 | 276.5 | 83.0 | 41.7 | 41.5 | 88.7 |
| NAB1 | 7 | 75.5 | 113.4 | 100.9 | 130.4 | 64.5 | 86.0 | 76.6 |
| NAB2 | 5 | 92.2 | 81.5 | 89.1 | 67.7 | 136.7 | 91.4 | 117.8 |
| NCAM2 | 2 | 0.7 | 28.2 | 32.9 | 1.7 | 4.5 | 14.6 | 9.7 |
| NEFL | 2 | 0.2 | 0.0 | 14.9 | 0.0 | 104.4 | 72.6 | 0.0 |
| NFIX | 6 | 408.1 | 436.6 | 437.1 | 451.6 | 387.4 | 222.1 | 617.4 |
| NPB:1 | 3 | 25.7 | 7.2 | 5.7 | 157.6 | 0.4 | 6.2 | 122.8 |
| NPH4 | 2 | 40.6 | 0.6 | 1.8 | 9.8 | 58.6 | 4.6 | 0.8 |
| NPW | 7 | 594.9 | 2341.1 | 588.3 | 1751.5 | 382.1 | 21.5 | 1178.0 |
| NR_002775 | 3 | 7.6 | 9.6 | 41.6 | 14.7 | 2.9 | 23.1 | 21.6 |
| NR_002797 | 5 | 198.7 | 271.2 | 215.7 | 362.0 | 150.3 | 146.9 | 538.5 |
| NR_003716 | 7 | 124.5 | 116.8 | 119.2 | 194.9 | 140.0 | 42.0 | 174.1 |
| NR3C1 | 2 | 7.5 | 25.6 | 68.7 | 26.0 | 43.0 | 39.6 | 16.4 |
| NRG2:3 | 2 | 5.9 | 9.3 | 5.2 | 28.0 | 19.6 | 1.8 | 47.4 |
| NRGN | 5 | 191.0 | 480.4 | 279.3 | 579.4 | 699.3 | 104.2 | 2015.6 |
| NTRK1 | 4 | 35.2 | 28.2 | 58.3 | 30.5 | 0.0 | 14.0 | 0.8 |
| NUMBL | 4 | 37.3 | 56.0 | 53.0 | 34.5 | 43.6 | 62.2 | 58.6 |
| NXPH4 | 2 | 45.0 | 0.7 | 2.0 | 10.8 | 65.0 | 5.0 | 0.9 |
| OAF | 2 | 164.2 | 192.9 | 25.0 | 284.7 | 97.7 | 7.3 | 447.7 |
| OLFM2 | 5 | 6.1 | 385.4 | 347.1 | 127.6 | 9.1 | 97.2 | 94.9 |
| PALM | 3 | 111.9 | 98.5 | 117.7 | 89.8 | 59.8 | 72.7 | 152.4 |
| PAM | 2 | 301.7 | 269.4 | 29.8 | 166.6 | 100.8 | 29.3 | 33.8 |
| PCDH10 | 2 | 1.3 | 69.7 | 51.1 | 9.3 | 0.2 | 0.2 | 23.6 |
| PCOLCE | 4 | 112.6 | 1179.3 | 1089.3 | 462.5 | 429.2 | 710.2 | 1392.6 |
| PCSK1 | 3 | 42.5 | 6.8 | 3.7 | 3.3 | 41.1 | 182.1 | 9.4 |
| PDGFD | 3 | 66.6 | 38.3 | 67.4 | 5.6 | 12.5 | 184.0 | 19.9 |
| PDZD4 | 2 | 48.6 | 1.6 | 9.9 | 61.3 | 0.5 | 15.2 | 20.2 |
| PEAR1 | 6 | 82.3 | 149.3 | 151.6 | 142.2 | 67.5 | 32.1 | 66.9 |
| PEGB/IGF2AS | 7 | 34.4 | 52.6 | 22.0 | 48.0 | 48.0 | 24.1 | 109.6 |
| PEPP1 | 3 | 144.2 | 54.5 | 102.8 | 62.7 | 50.6 | 77.3 | 134.8 |
| PAM | 2 | 299.0 | 239.5 | 23.8 | 107.1 | 93.8 | 23.0 | 23.3 |
| PHYHIP | 3 | 4.8 | 16.5 | 154.8 | 5.3 | 68.0 | 49.2 | 2.5 |
| PLEKHA4 | 3 | 134.3 | 56.3 | 109.5 | 62.9 | 62.8 | 84.3 | 118.0 |
| PLEKHG2 | 3 | 9.9 | 29.2 | 14.4 | 31.4 | 32.8 | 11.2 | 18.2 |
| PLK5 | 3 | 2.7 | 40.8 | 25.1 | 8.0 | 4.6 | 0.1 | 37.7 |
| PLSCR4 | 2 | 19.1 | 20.5 | 68.9 | 26.9 | 12.8 | 6.5 | 65.0 |
| PNMAL1 | 2 | 22.6 | 13.9 | 13.9 | 6.3 | 22.2 | 17.2 | 15.5 |
| PP14296 | 5 | 4.1 | 81.2 | 111.1 | 54.9 | 26.3 | 150.7 | 261.8 |
| pp9974 | 7 | 4580.0 | 6957.1 | 4723.8 | 17468.1 | 18147.8 | 6668.1 | 14211.7 |
| PPFIA4 | 2 | 27.6 | 7.5 | 31.5 | 14.5 | 11.4 | 13.6 | 3.7 |
| PRCD | 2 | 1.9 | 43.2 | 19.7 | 13.4 | 21.2 | 3.9 | 31.7 |
| PRKACB | 3 | 131.1 | 15.3 | 113.3 | 32.1 | 173.6 | 38.5 | 2.3 |
| PROS1 | 2 | 71.0 | 15.2 | 7.2 | 63.0 | 8.2 | 7.1 | 12.9 |
| PRRX2 | 5 | 57.9 | 94.6 | 211.9 | 301.9 | 115.2 | 52.2 | 148.1 |
| PRTN3 | 2 | 1.1 | 21.2 | 1.9 | 2.9 | 11.9 | 0.9 | 24.2 |
| PSD | 2 | 16.7 | 18.9 | 24.4 | 8.1 | 9.2 | 16.3 | 23.2 |
| PTCH2 | 4 | 10.6 | 90.9 | 41.2 | 37.9 | 2.4 | 5.9 | 31.0 |
| PTGDS | 2 | 526.8 | 616.5 | 4.1 | 5060.5 | 263.2 | 33.0 | 6228.9 |
| PTPN13 | 2 | 4.7 | 17.8 | 20.4 | 1.4 | 29.7 | 18.2 | 10.9 |
| PTPRV | 2 | 39.1 | 0.9 | 7.9 | 0.3 | 4.8 | 31.0 | 0.1 |
| RALGDS | 2 | 72.5 | 66.2 | 51.4 | 83.5 | 18.3 | 9.1 | 70.9 |
| RARA | 5 | 161.6 | 123.9 | 146.4 | 119.3 | 79.0 | 74.6 | 126.6 |
| RBM9 | 3 | 48.0 | 80.9 | 40.2 | 47.0 | 24.0 | 22.3 | 40.2 |
| RCN3 | 6 | 162.3 | 102.5 | 83.8 | 190.5 | 79.1 | 92.3 | 114.4 |
| ROM1 | 2 | 7.1 | 8.4 | 26.2 | 13.3 | 11.1 | 13.1 | 30.2 |
| SALP | 2 | 3.9 | 2.1 | 5.9 | 3.1 | 61.7 | 53.6 | 10.4 |
| SCLIP | 3 | 113.2 | 29.8 | 16.4 | 89.3 | 58.1 | 20.6 | 146.7 |
| SCN4B | 4 | 51.0 | 559.4 | 29.0 | 41.8 | 1.5 | 3.1 | 837.6 |
| SEMA6C | 5 | 24.2 | 62.3 | 25.5 | 41.2 | 9.1 | 15.4 | 33.7 |
| SEMA7A | 5 | 222.4 | 204.7 | 141.9 | 69.3 | 7.3 | 15.2 | 181.2 |
| semaY | 3 | 18.4 | 49.5 | 20.2 | 30.0 | 8.5 | 12.9 | 21.9 |
| SEPT5 | 3 | 23.0 | 28.0 | 38.0 | 44.5 | 9.6 | 22.0 | 85.4 |
| SERTAD2 | 3 | 27.3 | 32.4 | 30.7 | 16.0 | 22.6 | 20.7 | 22.0 |
| SESN3 | 2 | 2.3 | 4.0 | 6.9 | 1.0 | 24.7 | 26.9 | 1.5 |
| SEZ6L2 | 2 | 42.8 | 22.2 | 83.4 | 52.1 | 7.6 | 62.4 | 86.3 |
| SH3PXD2A | 4 | 29.5 | 63.7 | 98.8 | 36.9 | 23.6 | 183.3 | 57.9 |
| SIPA1L1 | 2 | 15.6 | 5.7 | 6.4 | 13.2 | 31.6 | 6.8 | 27.9 |
| SIX1 | 6 | 61.0 | 43.6 | 21.0 | 68.7 | 0.5 | 38.4 | 75.2 |
| SLC38A10 | 3 | 136.0 | 106.2 | 79.8 | 72.0 | 39.6 | 28.0 | 124.8 |
| SLIT2 | 2 | 42.0 | 0.3 | 1.9 | 3.3 | 7.1 | 57.0 | 14.2 |
| SLITRK3 | 2 | 0.0 | 33.5 | 26.8 | 0.0 | 0.8 | 0.8 | 0.8 |

TABLE 9-continued

| Gene | Number of Outlier Samples | Gene Expression (RPKM), Bold = Outlier | | | | | |
|---|---|---|---|---|---|---|---|
| | | MO_1005 | SFT3 | SFT18 | SFT28 | SFT31 | SFT40 | SFT44 |
| SMG6 | 2 | 26.3 | 39.0 | 47.0 | 29.9 | 31.1 | 24.3 | 51.1 |
| SORC52 | 4 | 42.7 | 5.3 | 85.4 | 0.5 | 51.7 | 83.0 | 1.1 |
| SPHK1 | 2 | 27.0 | 49.9 | 22.4 | 38.2 | 1.6 | 4.8 | 73.8 |
| STAT6 | 2 | 126.4 | 124.6 | 157.8 | 167.6 | 301.6 | 203.4 | 148.0 |
| STIM2 | 4 | 48.7 | 21.1 | 40.8 | 58.8 | 5.4 | 31.4 | 42.6 |
| STMN3 | 3 | 117.8 | 31.0 | 7.1 | 93.0 | 60.6 | 21.4 | 152.9 |
| STRA6 | 5 | 3.7 | 70.7 | 96.9 | 48.5 | 23.5 | 131.5 | 232.6 |
| SYNGAP1 | 5 | 43.5 | 26.4 | 28.8 | 56.0 | 47.6 | 36.6 | 8.1 |
| SYT1 | 3 | 0.6 | 10.7 | 23.4 | 4.3 | 24.4 | 30.0 | 1.1 |
| SYT7 | 6 | 222.4 | 329.1 | 458.9 | 235.8 | 123.3 | 448.8 | 176.6 |
| TAL1 | 4 | 40.7 | 1.6 | 16.0 | 44.8 | 58.3 | 4.8 | 46.7 |
| TBX15 | 3 | 0.3 | 9.6 | 1.9 | 59.8 | 42.8 | 25.3 | 39.8 |
| TBX5 | 2 | 0.0 | 1.1 | 56.3 | 0.1 | 0.6 | 50.6 | 0.1 |
| TCF-48 | 4 | 14.9 | 59.1 | 84.1 | 121.5 | 33.7 | 42.1 | 67.0 |
| TCF7L2 | 3 | 13.8 | 46.2 | 71.7 | 71.4 | 30.3 | 37.4 | 56.6 |
| TCTN1 | 2 | 36.9 | 32.5 | 21.5 | 17.5 | 14.6 | 16.3 | 21.2 |
| THBS4 | 2 | 61.9 | 171.6 | 4.9 | 2.6 | 1.0 | 133.5 | 14.2 |
| TLE2 | 5 | 231.2 | 218.3 | 225.0 | 316.5 | 80.5 | 20.6 | 342.8 |
| TLE3 | 5 | 102.4 | 130.6 | 126.2 | 122.5 | 30.3 | 34.1 | 139.9 |
| TLX1 | 4 | 0.5 | 68.8 | 34.6 | 90.3 | 11.1 | 0.5 | 92.6 |
| TMEM64 | 2 | 16.1 | 24.5 | 5.9 | 1.6 | 38.2 | 7.5 | 1.6 |
| TNFAIP6 | 2 | 1.7 | 9.4 | 37.2 | 0.2 | 0.9 | 48.0 | 1.5 |
| TNFRSF10C | 2 | 11.5 | 7.0 | 20.1 | 2.2 | 15.8 | 4.3 | 20.8 |
| TNNT3 | 6 | 31.4 | 539.7 | 129.7 | 49.5 | 55.8 | 672.9 | 149.1 |
| TRIM17 | 3 | 21.4 | 22.7 | 19.4 | 25.3 | 18.6 | 14.9 | 6.8 |
| TRIM67 | 3 | 74.7 | 0.0 | 0.0 | 48.5 | 0.0 | 0.0 | 89.8 |
| TUBA8 | 2 | 2.8 | 15.9 | 5.0 | 2.6 | 26.8 | 3.4 | 23.4 |
| TXNDC13 | 2 | 66.8 | 20.3 | 27.1 | 6.6 | 18.5 | 64.4 | 20.3 |
| UACA | 4 | 49.1 | 76.9 | 26.1 | 170.8 | 11.8 | 52.1 | 33.0 |
| UBL7 | 2 | 87.0 | 51.5 | 61.6 | 116.3 | 12.9 | 15.9 | 115.3 |
| UBTD2 | 2 | 11.6 | 22.2 | 32.6 | 10.2 | 25.4 | 94.5 | 9.4 |
| UNC5B | 2 | 19.8 | 3.7 | 19.8 | 3.4 | 107.6 | 83.3 | 2.7 |
| UNQ440 | 5 | 41.8 | 16.8 | 24.2 | 46.6 | 35.5 | 24.1 | 11.3 |
| UNQ440/PRO873 | 3 | 27.1 | 11.4 | 15.4 | 25.8 | 25.2 | 16.4 | 8.1 |
| UNQ9369 | 2 | 36.3 | 43.5 | 29.3 | 23.3 | 19.7 | 22.0 | 28.1 |
| USP53 | 2 | 3.6 | 1.8 | 63.8 | 67.5 | 31.8 | 4.9 | 10.0 |
| VASN | 3 | 292.8 | 268.1 | 158.1 | 156.6 | 112.3 | 66.5 | 692.1 |
| VAX2 | 3 | 15.0 | 3.9 | 5.3 | 38.4 | 43.4 | 7.2 | 80.9 |
| VCAM1 | 3 | 67.5 | 85.9 | 194.1 | 3.4 | 67.9 | 202.3 | 114.2 |
| VWCE | 2 | 31.2 | 8.1 | 13.4 | 7.7 | 11.0 | 2.2 | 20.3 |
| WASF1 | 3 | 14.1 | 37.0 | 30.8 | 17.5 | 7.1 | 25.7 | 8.8 |
| WDR19 | 2 | 24.8 | 18.2 | 15.9 | 21.9 | 12.8 | 18.9 | 13.5 |
| WHSC1L1 | 3 | 12.1 | 17.8 | 20.3 | 21.5 | 24.8 | 15.1 | 19.7 |
| WIPF3 | 2 | 0.6 | 0.5 | 32.1 | 0.1 | 38.2 | 3.2 | 9.7 |
| Y1P237 | 3 | 23.7 | 36.5 | 33.2 | 9.5 | 11.4 | 49.3 | 8.1 |
| ZBTB7C | 3 | 28.4 | 36.8 | 68.0 | 14.1 | 24.4 | 75.1 | 50.9 |
| ZIC2 | 2 | 108.4 | 0.1 | 0.0 | 122.0 | 0.4 | 0.1 | 0.9 |
| ZNF436 | 3 | 26.0 | 29.7 | 54.6 | 9.8 | 30.0 | 47.6 | 21.0 |
| ZNF516 | 2 | 8.0 | 18.6 | 22.1 | 6.7 | 31.7 | 15.7 | 13.5 |

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

We claim:

1. A method for detecting the presence of a NAB2-STAT6 gene fusion in a sample, comprising:
   a) contacting a biological sample from a subject with at least a first gene fusion informative reagent selected from the group consisting of:

a nucleic acid probe that hybridizes to the fusion junction in a nucleic acid selected from the group consisting of SEQ NOs: 25 and 27-30;

a pair of probes wherein said first probe hybridizes to NAB2 and said second probe hybridizes to STAT6;

a pair of nucleic acid primers that amplify a nucleic acid selected from the group consisting of SEQ NOs: 25 and 27-30, wherein said primers amplify a fusion junction of the NAB2-STAT6 gene fusion; and a sequencing primer that binds a nucleic acid selected from the group consisting of SEQ ID NO: 25 and 27-30 and generates an extension product that spans the fusion junction of said NAB2-STAT6 gene fusion;

(b) detecting the presence of a said NAB2-STAT6 gene fusion in said sample using said reagent by carrying out a hybridization reaction, amplification reaction or sequencing reaction appropriate to the reagent contacted.

2. The method of claim 1, wherein said reagent is a probe that specifically hybridizes to the fusion junction of a NAB2-STAT6 gene fusion.

3. The method of claim 1, wherein said reagent is a pair of primers that amplify a fusion junction of a NAB2-STAT6 gene fusion.

4. The method of claim 1, wherein the reagent is a sequencing primer that binds to a NAB2-STAT6 fusion and generates an extension product that spans the fusion junction of said NAB2-STAT6 gene fusion.

5. The method of claim 1, wherein said regent comprises a pair of probes wherein said first probe hybridizes to NAB2 and said second probe hybridizes to an STAT6 gene.

6. The method of claim 1, wherein said reagent is labeled.

7. The method of claim 1, further comprising the step of collecting said sample from said subject.

8. The method of claim 1, wherein the sample is selected from the group consisting of tissue, blood, plasma, serum, and cells.

* * * * *